(12) United States Patent
Domány et al.

(10) Patent No.: US 7,435,744 B2
(45) Date of Patent: Oct. 14, 2008

(54) PIPERIDINE DERIVATIVES AS NMDA RECEPTOR ANTAGONISTS

(75) Inventors: Gyorgy Domány, Budapest (HU); Csilla Horváth, Budapest (HU); Gizella Bartáné Szalai, Budapest (HU); József Nagy, Budapest (HU); Sándor Kolok, Budapest (HU); Éva Kovácsné Bozó, Budapest (HU); István Borza, Budapest (HU); István Vágó, Budapest (HU); Attila Bielik, Budapeset (HU); Györgyi Ignáczné Szendrei, Budapest (HU); György Keserü, Budapest (HU); Sándor Farkas, Budapest (HU)

(73) Assignee: Gedeon Richter Vegyeszeti Gyar RT (HU)

( * ) Notice: Subject to any disclaimer, the term of this patent is extended or adjusted under 35 U.S.C. 154(b) by 580 days.

(21) Appl. No.: 10/761,940

(22) Filed: Jan. 21, 2004

(65) Prior Publication Data

US 2004/0157886 A1   Aug. 12, 2004

Related U.S. Application Data

(63) Continuation of application No. PCT/HU02/00071, filed on Jul. 23, 2002.

(30) Foreign Application Priority Data

| Jul. 24, 2001 | (HU) | ................................... | 0103055 |
| Jul. 10, 2002 | (HU) | ................................... | 0202213 |

(51) Int. Cl.
*A61K 31/445* (2006.01)
*C07D 401/12* (2006.01)

(52) U.S. Cl. ..................... 514/321; 514/230.5; 514/322; 514/323; 544/106; 546/198; 546/199; 546/201

(58) Field of Classification Search .............. 514/230.5, 514/321, 322, 323; 544/105; 546/198, 199, 546/201

See application file for complete search history.

(56) References Cited

U.S. PATENT DOCUMENTS

| 2,324,123 | A |  | 7/1943 | Weissberger |
| 3,260,723 | A |  | 7/1966 | Yvon et al. |
| 3,632,767 | A |  | 1/1972 | Gray et al. |
| 5,436,255 | A |  | 7/1995 | Butler |
| 5,889,026 | A |  | 3/1999 | Alanine et al. |
| 6,048,900 | A |  | 4/2000 | Connell et al. |
| 6,124,323 | A |  | 9/2000 | Bigge et al. |
| 6,218,404 | B1 | * | 4/2001 | Bigge et al. ................. 514/317 |
| 6,399,631 | B1 | * | 6/2002 | Elliott et al. ................. 514/314 |

FOREIGN PATENT DOCUMENTS

| AU | A-70939/91 A | 5/1991 |
| CN | 1105990 A | 8/1995 |
| CN | 1171396 A | 1/1998 |
| CN | 1235604 A | 11/1999 |
| DE | 254 999 | 3/1912 |
| EP | 648 744 A1 | 4/1995 |
| EP | 0648744 A1 | 4/1995 |
| EP | 0824098 A1 | 2/1998 |
| FR | 2672286 A | 8/1992 |

(Continued)

OTHER PUBLICATIONS

Mederski et al. "Proline derivatives" CA 144:350972 (2006).*
Burrows et al. "Pharmaceutically active piperidine . . . " CA 135:371644 (2001).*

(Continued)

*Primary Examiner*—Celia Chang
(74) *Attorney, Agent, or Firm*—Rakoczy Molino Mazzochi Siwik LLP

(57) ABSTRACT

The present invention relates to a compound of formula (I):

(I)

wherein: V and U are hydrogen, halogen, $C_1$-$C_4$ alkylamino, or together form a group that contains one or more heteroatoms, and that taken together with one or more:
(a) hydrogen atoms;
(b) carbon atoms;
(c) —CH= groups;
(d) —$CH_2$— groups; or
(e) additional heteroatoms of the same or different type;
or any combination thereof, form a 4-7 membered homocyclic or heterocyclic ring, wherein the homocyclic or heterocyclic ring may combine with the phenyl group to form a bicyclic ring, and wherein the homocyclic or heterocyclic ring or the bicyclic ring may contain one or more oxo, thioxo, amino, mercapto, trifluoromethyl, $C_1$-$C_4$ alkyl, =S or —SH groups;
W: is —CO—, —$CH_2$— or —$CH_2$—($C_1$-$C_4$ alkyl)-;
X: is —CO—;
Y: is —O—, $C_1$-$C_4$ alkylene, $C_1$-$C_4$ alkynylene, cycloalkylene, aminocarbonyl, —NH—, —N($C_1$-$C_4$ alkyl)-, -$C_1$-$C_4$ alkylene-N($C_1$-$C_4$ alkyl)-, —$CH_2$O—, —CH(OH)— or —$OCH_2$—;
Z: is hydrogen, halogen, nitro, amino, $C_1$-$C_4$ alkyl, $C_1$-$C_4$ alkoxy, cyano, trifluoromethyl, hydroxyl or carboxyl;
$R^1$ and $R^2$: are hydrogen, or together form a $C_1$-$C_3$ bridge; and
n and m: independently are 0-3, wherein n and m cannot each be 0;
or an optical antipode, racemate or pharmaceutically-acceptable salt thereof. The carboxylic acid amide derivatives of formula (I) are highly effective and selective antagonists of the NMDA receptor.

27 Claims, No Drawings

FOREIGN PATENT DOCUMENTS

| | | |
|---|---|---|
| NL | 6501323 | 8/1966 |
| WO | WO90/14087 A1 | 11/1990 |
| WO | WO97/23202 A1 | 7/1997 |
| WO | WO97/23214 A1 | 7/1997 |
| WO | WO97/23215 A1 | 7/1997 |
| WO | WO97/23216 A1 | 7/1997 |
| WO | WO 97/23216 A1 | 7/1997 |
| WO | WO97/23458 A1 | 7/1997 |
| WO | WO98/18793 A1 | 5/1998 |
| WO | WO99/21539 A1 | 5/1999 |
| WO | WO90/14088 A1 | 11/1999 |
| WO | WO00/00197 A1 | 1/2000 |
| WO | WO00/25109 A1 | 5/2000 |
| WO | WO01/30330 A2 | 5/2001 |
| WO | WO01/32171 A1 | 5/2001 |
| WO | WO01/32174 A1 | 5/2001 |
| WO | WO01/32177 A1 | 5/2001 |
| WO | WO01/32179 A1 | 5/2001 |
| WO | WO01/32615 A1 | 5/2001 |
| WO | WO01/32634 A1 | 5/2001 |

OTHER PUBLICATIONS

Kolarova et al. "Blockade of NMDA . . . " CA 141:47098 (2003).*
Li et al. "Application development of antagonists. of . . . " CA 142:232125 (2004).*
Torrens et al. "Preparation of phenylaminopiperidinyl-acetamides . . . " CA 142:240321 (2005).*
Sax et al. "Relationships between the structure . . . " CA 145:158900 (2006).*
Silverman "The organic chemistry of drug design and drug action" Acad. Press, p. 72-76 (1993).*
DeVry et al. "Pharmacological characterization . . . " CA 141:116988 (2004).*
Barta, Thomas, E., et al., Synthesis and Activity of Selective MMP Inhibitors with an Aryl Backbone, Bioorg. Med. Chem. Lett., (2000), pp. 2815-2817, vol. 10.
Beckett, A.H., et al., Substituted Oxinodoles-I: The Preparation and Spectral Characteristics of Some Simple Oxindole Derivatives, Tetrahedron, (1968), pp. 6093-6109, vol. 24.
Beveridge, S. and Huppatz, J.L., The Pschorr Cyclization II, Further Reactions with Pyrrole Derivatives, Aust. J. Chem., (1972), pp. 1341-1346, vol. 25.
Bisaga, A., and Popik, P., In Search of a New Pharmacological Treatment for Drug and Alcohol Addition: . . . , Drug and Alcohol Depend., (2000) pp. 1-15, vol. 59.
Boswell, R.F., et al., Synthesis of Some N-Carboxylic Acid Derivatives of 3-Phenoxypyrrolidines, J. Med. Chem., (1974), pp. 1000-1008, vol. 17.
Boyce, S., et al., Selective NMDA NR2B Antagonists Induce Antinocciception Without Motor Dysfunction: Correlation with Restricted Localisation . . . , pp. 611-623, vol. 38.
Buehler, C.A., Harris, J.O., and Arendale, W.F., Reaction of appha- and gamma-Stilbazoles with Selenium Dioxide, J. Amer. Chem. Soc., (1950), pp. 4953-4955, vol. 72.
Chapleo, C.B., et al., Heteroaromatic Analogues of the •2-Adrenoreceptor Partial Agonist Clonidine, J. Med. Chem., (1989), pp. 1627-1630, vol. 32.
Chenard, B.L., and Menniti, F.S., Antagonists Selective for NMDA Receptors Containing the NR2B Subunit, Curr. Pharm. Des., (1999), pp. 381-404, vol. 5.
Chiarino D. and Contri, A.M., 2,1-Benzisothiazoline 2,2-Dioxide and Derivatives, J. Heterocycl. Chem., (1986), pp. 1645-1649, vol. 23.
Clark, R.L., and Pessolano, A.A., Synthesis of Some Substituted Benzimidazolones, J. Amer. Chem. Soc., (1958), pp. 1657-1662, vol. 80.
Crook, K.E., and McElvain, S.M., Piperdine Derivatives The Phenylpiperidylcarbinols, J. Amer. Chem. Soc., (1930), pp. 4006-4011, vol. 52.

Desai, R.D., et al., The Unsaturation and Taulomeric Mobility of Hetercyclic Comps. Part XI. alpha- and beta-Napthoxazole and . . . , J. Chem. Soc., (1938), pp. 321-329, vol. 321.
Di, Xiao, et al., Effect of CP101,606, a Novel NR2B Subunit Antagonist of the N-Methyl-D-Aspartate Receptor, on the Vol. of Isch., Stroke (1997), pp. 2244-2251, vol. 28.
Dickens, F., et al., The Formation and Stability of Spiro-Compounds Part VIII. The Diekmann-Komppa Reaction, J. Chem. Soc., (1922), pp. 1496-1507, vol. 121.
Dickenson, A. and Besson, J.M. (Eds.): The Pharmacology of Pain . . . Excitatory Amino Acid Mechanisms and Their Control, (1997), Springer-Verlag, Berlin.
Dománg et al, New 4-Arylaminopiperidines with Antihypoxic and Anticonvulsive Activity, Drug Research, (1994), pp. 989-991, vol. 44(II), No. 9.
El Kihel, A., et al., Reaction of Aminobenzimidazoles with 4-Hydroxy-6-methyl-2-pyrone and 4-Hydroxycoumarine, Synth. Commun., (1999), pp. 2434-2444, vol. 29.
Faden, A.I., et al., Effects of Competitive and Non-Competitive NMDA Receptor Antagonists in Spinal Cord Injury, Eur. J. Pharmacol., (1990), pp. 165-174, vol. 175.
Hartmann, M., and Panizzon, L., Über die Darstellung des Aminoisatins und einiger Derivate, Helv. Chim-Acta, (1936), pp. 1326-1333, vol. 19.
Helsley, G.C., et al., Piperidylalkylindoles. 1. Hypotensive Activity of 3-[2-(Phenoxypiperidyl)ethyl]indoles, J. Med. Chem., (1978), pp. 309-312, vol. 21.
Herndon, J.L., et al., Ketanserin Analogues: Structure-Affinity Relationships for 5-HT2 and 5-HT1C Serotonin Receptor Binding, J. Med. Chem., (1992), pp. 4903-4910, vol. 35.
Hodgson, H.H., and Marsden, E., Evidence of the isoNitrile and Nitrile Structures of Hantzsch's Aryl syn- and . . . , J. Chem. Soc., (1944), pp. 1515-1519, vol. 395.
Hong Li, Jin, et al., Developmental Changes in Localization of NMDA Receptor Subunits in Primary Cultures . . . , Eur. J. Neuroscience, (1998), pp. 1704-1715, vol. 10.
Hunskaar, S., et al, Formalin Test in Mice, a Useful Technique for Evaluating Mild Analgesics, Journal of Neuroscience Methods, (1985) pp. 69-76, vol. 14.
Iovu, Mircea, et al., Experimental Pharmacodynamic Study of Some New Aminoacetarylides and Phenoxyacetarylides, Chemical Abstracts, (1982), p. 601, Bucharest, vol. 33, No. 7.
Jacobson, P., Ueber Diazosulfide, Liebigs Ann. Chem., (1893), pp. 209-261, vol. 277.
Jain, K.K., Evaluation of Memantine for Neuroprotection in Dementia, Expert Opin. Investig. Drugs, (2000), pp. 1397-1406, vol. 9.
James, A.T., and Turner, E.E., Structure and Antimalarial Activity, Part IV. Benziminazoles and Mercaptodihydroglyoxalines, J. Chem. Soc., (1950), pp. 1515-1519.
Johnson, M.I., and Bunge, R.P., Primary Cell Cultures of Peripheral . . . , In: Protocols for Neural Cell Culture, eds: Fedoroff, S.; Richardson A., (1992), pp. 51-75, Chap. 4.
Kao, J.P.Y., Practical Aspects of Measuring [Ca2+] with Fluorescent Indicators, Meth. Cell. Biol., (1994), pp. 155-181, vol. 40.
Katz, L and Cohen, M.S., Benzoxazole Derivatives. I. 2-Mercaptobenzoxazoles, J. Org. Chem., (1954), pp. 758-766, vol. 19.
Kaufmann, H.P., Arzneimittelsynthetische Studien IX: Benzthiazolylharnstoffe (Mitbearbeitet von P. Schulz), Arch. Pharm., (1935), p. 31-53, vol. 13.
Lipton, Stuart A., Neuronal Injury Associated with HIV-1: Approaches to Treatment, Annu. Rev. Pharmacol. Toxicol., (1998), pp. 159-177, vol. 38.
Lutfy, Kabirullah, et al., Inhibition of Morphine Tolerance by NMDA Receptor Antagonists in the Formalin Test, Brain Res., (1996), pp. 171-181, vol. 731.
Manabe, Y., et al., Enhanced Fos Expression in Rat Lumbar Spinal Cord Cultured with Cerebrospinal Fluid From Patents . . . , Neurol. Res., (1999), pp. 309-312, vol. 21.
Mercer, L.D., et al., I-Ifenprodil: Synthesis and Characterization of Binding to a Polyamine-Sensitive Site . . . , J. Neurochem., (1993), pp. 120-126, vol. 61.

Monge, A., et al., Synthesis of New Oxazolidine, Oxazolidin-2-one and Perhydro-1,4-oxazine Derivatives of . . . , J. Heterocycl. Chem., (1995), pp. 1429-1438, vol. 32.

Mutel, V., et al., In Vitro Binding Properties in Rat Brain of [3H]RO 25-6981, a Potent and Selective Antagonist of NMDA . . . , J. Neurochem., (1998), pp. 2147-2155, vol. 70.

Okiyama, K., et al., Effects of the NMDA Antagonist CP-98-113 on Regional Cerebral Edema and Cardiovascular, . . . , Brain Res., (1998), pp. 291-298, vol. 792.

Parsons, W., Danysz, W. and Quack, G., Glutamate in CNS Disorders as a Target for Drug Development: An Update, Drug News Perspect., (1998), pp. 523-569, vol. 11.

Perez, M., et al., Synthesis, Binding Affinity and Intrinsic Activity of New Anilide Derivatives of Serotonin at Human 5-HT1D . . . , Eur. J. Med. Chem., (1997), 129-134, vol. 32.

Rajappa, S. and Shenoy, S.J., Quinone-imides: Regiospecificity of Nucleophilic Attack on N-alkanesulphonyl-N1-alkanoyl 1, . . . , Tetrahedron, (1986), pp. 5739-5746, vol. 42.

Reinert, M.M. and Bullock, R., Clinical Trials in Head Injury, Neurol. Res., (1999), pp. 330-338, vol. 21.

Rothman, S.M. and Olney, J.W., Excitotoxicity and the NMDA Receptor, TINS, (1987), pp. 299-302, vol. 10.

Sajiki, H., Selective Inhibition of Benzyl Ether Hydrogenolysis with Pd/C Due to the Presence of Ammonia, Pyridine . . . , Tetrahedron Lett., (1995), pp. 3465-3468, vol. 36.

Sam, J., Richmond, C.W., and Valentine, J.L., 3-Aminoalkyl-2-benzoxazolinones, J. Med. Chem., (1967), pp. 408-410, vol. 10.

Sato, Yasunobu, et al., Syntheses and pharmacology of 1-[2-(hydroxyethoxy)ethyl]-4-(p-chlorobenzyl) piperidine hydrocholoride (piclobetol) . . . , Heterocycles (1972), 34266w.

Shridhar, D.R., et al., Potential Diuretics: Part I-Synthesis of Some Substituted 2,4-Dihydro-1-oxo/thioxo[1,2,4]triazolo . . . , Indian J. Chem., (1984), pp. 1279-1283, vol. 23B.

Shridhar, D.R., et al., Synthesis & Anthelmintic Activity of Some New 6- & 7-Isothiocyanato-2H-1,4-benzoxa(thia) . . . , Indian J. Chem., (1985), pp. 1263-1267, vol. 24B.

Singh, A.K., and Kanvah, S., Photophysical Studies of Substituted 1,2-diarylethenes: twisted Intramolecular . . . , J. Chem. Soc. Perkin Trans., (2001), pp. 395-401, vol. 2.

Steece-Collier, K., et al., Antiparkinsonian Actions of CP-101,606, an Antagonist of NR2B Subunit-Containing N-Methyl-D- . . . , Exp. Neurol., (2000), pp. 239-243, vol. 163.

Tchani, G., et al., Evaluation of Inhibitory Calcic Activity of a Series of Diethylbenzylphosphonates, Eur. J. Med. Chem., (1992), pp. 845-850, vol. 27.

Tomita, Masatsugu, and Minami, Shinsaku, The Schmidt Reaction with Benzocycloalkenones, J. Chem. Soc., (1969), pp. 183-188, vol. 196.

Turski, L., et al., Muscle Relaxant and Anticonvulsant Activity of 3-(('')-2-carboxypiperazin-4-yl)-propyl-1-phosphonic . . . , Neurosci. Lett., (1987), pp. 143-148, vol. 73.

Warrener, R.N., et al., A Concise, Regio and Stereoselective Route to Fluorinated Protoberberines via Tandem Addition- . . . , Tetrahedron, (1998), pp. 7485-7496, vol. 54.

Weissman, S.A., et al., Efficient Synthesis of N-Arylpiperazinones via a Selective Intramolecular Mitsunobu Cyclodehydration Tetrahedron Lett., (1998), pp. 7459-7462, vol. 39.

Wheeler, A.S., and Smith, S.C., Direct Conversion of Derivatives of Dichloro-acetic Acid into Derivatives of . . . , J. Amer. Chem. Soc., (1923), pp. 1994-1999, vol. 45.

Woo Bae, J., et al., Chemoselective Reduction of Nitroaromatics to Anilines Using Decaborane in Methanol, Tetrahedron Lett., (2000), pp. 175-177, vol. 41.

Zhou, Zhang-Lin and Keana, J.F.W., A Practical Synthesis of 4-(Substituted-benzyl)piperidines and ('')-3-(Substituted-benzyl) . . . , J. Org. Chem., (1999), pp. 3763-3766, vol. 64.

B.L. Chenard, et al., Separation of (alpha) Adrenergic and N-Methyl-D-Aspartate Antagonist Act. in a Series of Ifenprodil Cpds., J. Med. Chem., 1941, 3085-3090, vol. 34, No. 10.

C. Dominguez, et al., Design and Synthesis of potent and selective 5,6-fused heterocyclic thrombin inhibitors, Bio Org. Med. Chem. Lett., 1999, 925-930, vol. 9.

PCT International Search Report for Int'l Application No. PCT/HU02/00071 (later published as WO 03/010159 A1).

Dominguez et al., Design and Synthesis of Potent and Selective 5,6-Fused Heterocyclic Thrombin Inhibitors, 9 Bioorganic & Medicinal Chemistry Letters 925-930 (1999).

Chenard et al., Separation of Alpha1 Adrenergic and N-Methyl-D-Aspartate Antagonist Activity in a Series of Ifenprodil Compounds, 34 Journal of Medicinal Chemistry 3085-3090 (1991).

* cited by examiner

PIPERIDINE DERIVATIVES AS NMDA RECEPTOR ANTAGONISTS

This application is a continuation patent application of International application no. PCT/HU02/00071, filed Jul. 23, 2002, which claims priority to Hungarian patent application nos. P 0103055 (filed Jul. 24, 2001) and P 0202213 (filed Jul. 10, 2002). The International application and both Hungarian applications are each hereby incorporated by reference in their entirety.

FIELD OF THE INVENTION

The present invention relates to carboxylic acid amide derivatives which are antagonists of NMDA receptors, intermediates and processing for preparing the same.

BACKGROUND OF THE INVENTION

N-methyl-D-aspartate (NMDA) receptors are ligand-gated cation-channels embedded in the cell membranes of neurons. Overactivation of NMDA receptors by glutamate, their natural ligand, can lead to calcium overload of cells. This triggers a cascade of intracellular events that alters the cell function and ultimately may lead to death of neurons [TINS, 10, 299-302 (1987)]. Antagonists of the NMDA receptors may be used for treating many disorders that are accompanied with excess release of glutamate, the main excitatory neurotransmitter in the central nervous system.

The knowledge on the NMDA receptor structure, function and pharmacology has expanded owing to recent achievements of the molecular biology. The NMDA receptors are heteromeric assemblies built up from at least one NR1 subunit and at least one of the four different NR2 subunits (NR2A-D). Both spatial distributions in the CNS and the pharmacological sensitivity of NMDA receptors built up from various NR2 subunits are different. Particularly interesting of these is the NR2B subunit due to its restricted distribution (highest densities in the forebrain and substantia gelatinosa of the spinal cord). Compounds selective for this subtype are available [Curr. Pharm. Des., 5, 381-404 (1999)] and have been proved to be effective in animal models of stroke [Stroke, 28, 2244-2251 (1997)], traumatic brain injury [Brain Res., 792, 291-298 (1998)], Parkinson's disease [Exp. Neurol., 163, 239-243 (2000)], neuropathic and inflammatory pain [Neuropharmacology, 38, 611-623 (1999)]. Moreover, NR2B subtype selective antagonists of NMDA receptors are expected to possess little or no untoward side effects that are typically caused by the non-selective antagonists of NMDA receptors, namely psychotomimetic effects such as dizziness, headache, hallucinations, dysphoria and disturbances of cognitive and motor function.

NR2B subtype selective NMDA antagonism can be achieved with compounds that specifically bind to, and act on, an allosteric modulatory site of the NR2B subunit containing receptors. This binding site can be characterized by displacement (binding) studies with specific radioligands, such as [$^{125}$I]-ifenprodil [J.Neurochem., 61, 120-126 (1993)] or [$^3$H]-Ro 25,6981 [J. Neurochem., 70, 2147-2155 (1998)]. Since ifenprodil was the first, though not sufficiently specific, known ligand of this receptor, it has also been termed ifenprodil binding site.

Close structure analogs of the carboxylic acid amide derivatives of formula (I) are known from the literature. The Florida Center for Heterocyclic Compounds [Department of Chemistry, University of Florida, P.O. Box 117200, Gainesville, Fla., 32611-7200] provides milligram quantities of three compounds of formula (I) for biological testing: N-(4-bromophenyl)-4-(phenylmethyl)-1-piperidineacetamide, 4-[[oxo[4-(phenylmethyl)-1-piperidinyl]acetyl]amino]benzoic acid and 4-[[oxo[4-(phenylmethyl)-1-piperidinyl]acetyl]amino]benzoic acid ethyl ester.

Oxo-ethylamino derivatives are described as intermediates for thrombin inhibitors [Bioorg. Med. Chem. Letters, 9, 925. (1999)]. The publication does not describe NMDA receptor antagonist effect.

N-(4-Benzoylphenyl)-4-(phenylmethyl)-1-piperidineacetamide is mentioned in U.S. Pat. No. 6,048,900 as selective neuropeptide Y receptor antagonist.

N-(2-Formyl-6-methylphenyl)-4-(phenylmethyl-1-piperidineacetamide is described in Australian patent application No. AU 639529 as an intermediate for carbostyril derivative which is useful as antiarrhythmics.

Aminoacetarylides are also known [Rev. Chim. (Bucharest), 33(7), 601. (1982); CA 97:174467a] as local anesthetic and antifibrillatory agents.

Piperidine derivatives and analogues substituted with phenols or phenol equivalents having NR2B selective NMDA antagonist activity are described in international patent application nos. WO 90/14087, WO 90/14088, WO 97/23202, WO 97/23214, WO 97/23215, WO 97/23216, WO 97/23458, WO 99/21539, WO 00/25109, European patent application No. EP 648744 A1 and in U.S. Pat. No. 5,436,255. Compounds containing 2-benzoxazolinone substructure with the same biological activity are described in international patent applications WO 98/18793 and WO 00/00197. Other NR2B selective NMDA antagonists having condensed heterocyclic structures are described in international patent application nos. WO 01/30330, WO 01/32171, WO 01/32174, WO 01/32177, WO 01/32179, 01/32615, WO 01/32634.

However, there continues to be a need for novel NMDA antagonists that target the NR2B receptor.

SUMMARY OF THE INVENTION

Carboxylic acid amide derivatives of formula (I)

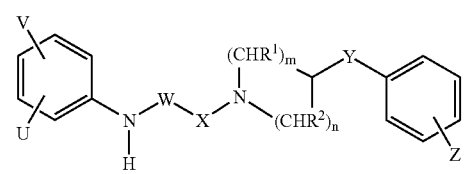

are functional antagonists of NMDA receptors, which target the NMDA receptors primarily via binding to the ifenprodil binding site and are, thus, believed to be NR2B subtype specific antagonists.

DETAILED DESCRIPTION OF THE INVENTION

The present invention relates therefore first to carboxylic acid amide derivatives of formula (I):

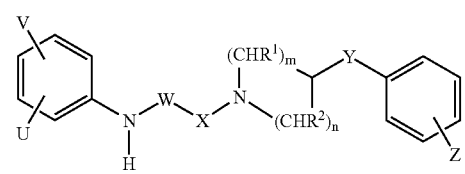

wherein

V and U are hydrogen or halogen atom, hydroxyl, cyano, nitro, amino, $C_1$-$C_4$ alkylamino optionally substituted by a halogen atom or halogen atoms, arylamino optionally substituted by a halogen atom or halogen atoms, aralkylamino optionally substituted by a halogen atom or halogen atoms, $C_1$-$C_4$ alkylsulfonamido optionally substituted by a halogen atom or halogen atoms, $C_1$-$C_4$ alkanoylamido optionally substituted by a halogen atom or halogen atoms, arylsulfonamido, $C_1$-$C_4$ alkylsulfonyloxy, carboxyl, trifluoromethyl, trifluoromethoxy, $C_1$-$C_4$ alkyl-$SO_2$—NH—$CH_2$—, $NH_2$—$(CH_2)_{1-4}$—$SO_2$—NH—, $NH_2$—$(CH_2)_{1-4}$—(CO)—NH—, sulfamoyl [$NH_2$—$SO_2$—], formyl [—CHO], amino-methyl [—$CH_2$—$NH_2$], hydroxymethyl, $C_1$-$C_4$ alkyl, $C_1$-$C_4$ alkoxymethyl, halogenmethyl, tetrazolyl group, or $C_1$-$C_4$ alkoxy, $C_1$-$C_4$ alkoxycarbonyl, $C_1$-$C_6$ alkanoyloxy, phenyl or $C_1$-$C_4$ alkoxy groups, optionally substituted by amino group, or the neighboring V and U groups in given case together with one or more identical or different additional hetero atom and —CH= and/or —$CH_2$— groups can form an optionally substituted 4-7 membered homo- or heterocyclic ring, preferably morpholine, pyrrole, pyrrolidine, oxo- or thioxo-pyrrolidine, pyrazole, pyrazolidine, imidazole, imidazolidine, oxo- or thioxo-imidazole or imidazolidine, 1,4-oxazine, oxazole, oxazolidine, oxo- or thioxo-oxazolidine, or 3-oxo-1,4-oxazine ring, W and X independently are —CO—, —$CH_2$— or —CH(-alkyl)- groups, wherein alkyl is a $C_1$-$C_4$ alkyl group groups—with the restriction, that the meaning of W and X can not be methylene at the same time Y is oxygen, as well as $C_1$-$C_4$ alkylene, $C_1$-$C_4$ alkynylene, cycloalkylene, aminocarbonyl, —NH—, —N(alkyl)-, —$CH_2O$—, —CH(OH)—, —$OCH_2$— group,—wherein alkyl is a$C_1$-$C_4$ alkyl-, Z is hydrogen or halogen, nitro, amino, $C_1$-$C_4$ alkyl, $C_1$-$C_4$ alkoxy, cyano, trifluoromethyl, hydroxyl or carboxy, $R^1$ and $R^2$ independently are hydrogen atom or alkyl, or $R^1$ and $R^2$ together form an optionally substituted $C_1$-$C_3$ bridge and n and m independently are 0-3, with the restriction, that n and m can not be 0 at the same time, and optical antipodes or racemates and/or pharmaceutically acceptable salts thereof formed with acids and bases with the proviso that when Z is hydrogen, Y is —$CH_2$—, both of m and n are 2, both of $R^1$ and $R^2$ are hydrogen atom, W is —CO—, X is —$CH_2$— and V is hydrogen, then the meaning of U is other than a 4-bromo substituent and when Z is hydrogen, Y is —$CH_2$— group, both of m and n are 2, both of $R^1$ and $R^2$ are hydrogen atom, both of W and X are —CO— group and V is hydrogen atom, then the meaning of U is other than a 4-carboxyl or 4-etoxycarbonyl substituent.

Further objects of the present invention are the pharmaceutical compositions containing carboxylic acid amide compounds of formula (I) or optical antipodes or racemates or the salts thereof as active ingredients.

A further object of the invention are the processes for producing of carboxylic acid amide compounds of formula (I), and the pharmaceutical manufacture of medicaments containing these compounds, as well as the process of treatments with these compounds, which means administering to a mammal to be treated—including human—effective amount/amounts of compounds of formula (I) of the present invention or as a medicament.

The carboxylic acid amide derivatives of formula (I) of the present invention are highly effective and selective antagonists of NMDA receptor, and moreover most of the compounds are selective antagonist of NR2B subtype of NMDA receptor.

According to the invention the carboxylic acid amide compounds of formula (I) can be prepared by the following processes:

a) for producing of compounds of formula (I) wherein X is —CO— and $R^1$, $R^2$, Y, Z, U, V, W, n and m are as given above for the formula of (I), a carboxylic acid of formula (II)

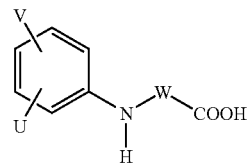

(II)

wherein U, V and W are as given for the formula of (I) or a reactive derivative of it, is reacted with an amine of formula (III)

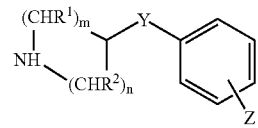

(III)

wherein the meaning of $R^1$, $R^2$, Y, Z, n and m are as given before for the formula of (I), or b) for producing of compounds of formula (I) wherein W is —CO— and $R^1$, $R^2$, Y, Z, U, V, X, n and m are as given before for the formula of (I) a carboxylic acid of formula (IV)

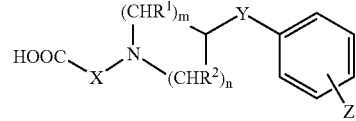

(IV)

wherein X, $R^1$, R 2, Y, Z, n and m are as described above for the formula of (I) or a reactive derivative of it is reacted with an amine of formula (V)

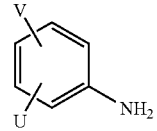

(V)

wherein U and V are as given before for the formula of (I), or c) for producing of compounds of formula (I) having X is —$CH_2$— or —CH(-alkyl)- wherein alkyl is $C_1$-$C_4$ alkyl and $R^1$, $R^2$, Y, Z, U, V, W, n and m are as given before for the formula of (I) a halogene derivative of a compound of formula (VI)

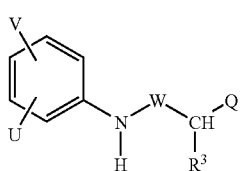

(VI)

wherein Q is halogen, R³ is hydrogen or a $C_1$-$C_4$ alkyl group and U, V and W are as described above for the formula of (I), is reacted with an amine of formula (III)

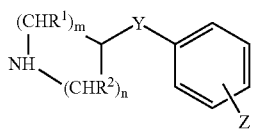

(III)

wherein $R^1$, $R^2$, Y, Z, n and m are as given before for the formula of (I)-, or d) formula (I) wherein W is —$CH_2$— or —CH(-alkyl)- wherein alkyl is a $C_1$-$C_4$ alkyl and $R^1$, $R^2$, Y, Z, U, V, X, n and m are as given before for the formula of (I), a halogene derivative of a compound of formula (VII)

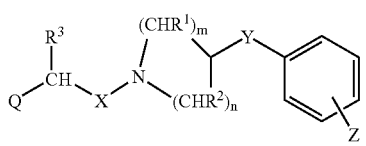

(VII)

wherein Q is halogen, $R^3$ is hydrogen or $C_1$-$C_4$ alkyl and X, $R^1$, $R^2$, Y, Z, n and m are as described above for the formula of (I), is reacted with an amine of formula (V)

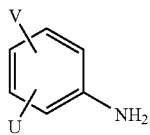

(V)

wherein U and V are as given before for the formula of (I), or e) for producing compound of formula (I), where X are —CO— group and $R^1$, $R^2$, Y, Z, U, V, n and m are as defined for the formula (I), a secondary amine of formula (III)

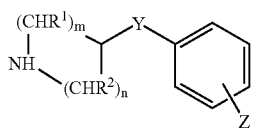

(III)

wherein $R^1$, $R^2$, m, n, Y and Z have the same meaning as given for formula (I), is reacted with ethyl oxalylchloride in the presence of solid-supported base in dichloromethane, the obtained ester compound of formula (VIII)

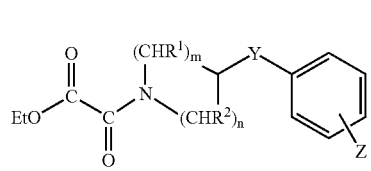

(VIII)

where $R^1$, $R^2$, m, n, Y and Z have the same meaning as given for formula (I), is saponified with a strongly basic ion exchange resin in ethanol and the obtained oxalamid acid of formula (IX)

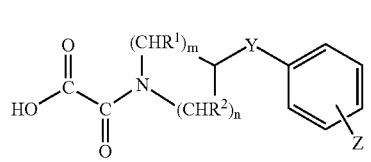

(IX)

where $R^1$, $R^2$, m, n, Y and Z have the same meaning as given for formula (I), is reacted with an amide of formula (V)

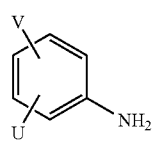

(V)

wherein U and V are as given before for the formula of (I)—in dichloromethan/dimethylformamide mixture in the presence of 1-[3-(dimethylamino)-propyl]-3-ethyl-carbodiimide, or f) for producing compound of formula (I), where X is —$CH_2$— and $R^1$, $R^2$, Y, Z, U, V, n and m are as defined for the formula (I), a secondary amine of formula (III)

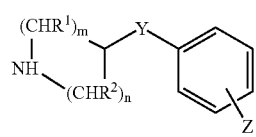

(III)

wherein $R^1$, $R^2$, m, n, Y and Z have the same meaning as given for formula (I), is reacted with methyl bromoacetate in the presence of potassium carbonate in dimethylformamide, the obtained ester compound of formula (X)

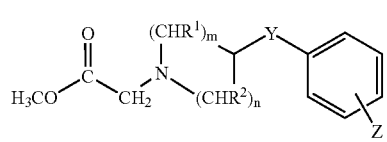

(X)

where $R^1$, $R^2$, m, n, Y and Z have the same meaning as given for formula (I) is saponified with a strongly basic ion exchange resin in ethanol and the obtained substituted glycine of formula (XI)

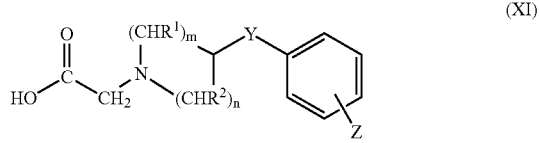

where $R^1$, $R^2$, m, n, Y and Z have the same meaning as given for formula (I) is reacted with an amide of formula (V)

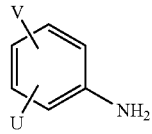

wherein U and V are as given before for the formula of (I), in dichloromethan/dimethylformamide mixture in presence of 1-[3-(dimethylamino)-propyl]-3-ethylcarbodiimide, and the obtained compounds of formula (I), where $R^1$, $R^2$, Y, Z, U, V, X, W, n and m are as defined above, in given case are transformed into another compound of formula (I) by introducing further substituents and/or modifying and/or removing the existing ones, and/or formation of salts with acids and/or liberating the carboxylic acid amide derivative of formula (I) from the obtained acid addition salts by treatment with a base and/or the free carboxylic acid amide derivative of formula (I) can be transformed into a salt by treatment with a base and/or are resolved into their optical antipodes.

The amide bond formation is preferably carried out by preparing an active derivative from a carboxylic acid of formula (II) or (IV) which is reacted with an amine of formula (III) or (V) preferably in the presence of a base.

The transformation of a carboxylic acid into an active derivative can be carried out in situ during the amide bond formation in a proper solvent (for example dimethylformamide, acetonitrile, chlorinated hydrocarbons or hydrocarbons). The active derivatives can be acid chlorides (for example prepared from carboxylic acid with thionyl chloride), mixed anhydrides (for example prepared from carboxylic acid with isobutyl chloroformate in the presence of a base, e.g., triethylamine), active esters (for example prepared from carboxylic acid with hydroxybenztriazol and dicyclohexylcarbodiimide or O-benzotriazol-1-yl-N,N,N',N'-tetramethyluronium hexafluorophosphate (HBTU) in the presence of a base, e.g., triethylamine), acid azides (for example prepared from carboxylic acid hydrazide). The active derivatives can be prepared between room temperature and 0° C. A proper amine of formula (III) or (V) is added as base or as a salt formed with inorganic acid to the so obtained solution or suspension in the presence of a base, for example triethylamine, needed for the liberation of the amine. The condensation reactions are followed by thin layer chromatography. The necessary reaction time is 6-20 hours. The work-up of the reaction mixture can be carried out by different methods.

The amide bond formation is preferably carried out by refluxing in a proper solvent an amine of formula (III) or (V) with a halogen compound of formula (IV) or (VII) in the presence of an organic base (e.g., triethylamine, pyridine, piperidine) or an inorganic base (e.g., sodium carbonate or potassium carbonate) and sodium iodide. The proper solvent can be an aprotic solvent (e.g., toluene, chlorinated hydrocarbons) or a dipolar aprotic solvent (e.g., ketone, acetonitrile or dimethylformamide). The reactions are followed by thin layer chromatography. The necessary reaction time is 20-50 hours. The work-up of the reaction mixture also can be carried out by different methods.

When the reaction mixture is a suspension, the precipitate is filtered off, washed with water and/or with an organic solvent and recrystallized from a proper solvent to give the pure product. If the crystallization does not lead to the pure product, then column chromatography can be used for the purification of it. The column chromatography is carried out on normal phase using Kieselgel 60 as adsorbent and different solvent systems, e.g., toluene/methanol, chloroform/methanol or toluene/acetone, as eluents. If the reaction mixture is a solution at the end of the acylation or alkylation, it is concentrated, and the residue is crystallized or purified by column chromatography as described above. The structure of the products are determined by IR, NMR and mass spectrometry.

The obtained carboxylic acid amide derivatives of formula (I)—independently from the method of preparation—in given case can be transformed into an other compound of formula (I) by introducing further substituents and/or modifying and/or removing the existing ones, and/or formation of salts with acids and/or liberating the carboxylic acid amide derivative of formula (I) from the obtained acid addition salts by treatment with a base and/or the free carboxylic acid amide derivative of formula (I) can be transformed into a salt by treatment with a base.

For example cleaving the methyl and benzyl groups from methoxy and benzyloxy groups, which stands for U, V and Z, leads to phenol derivatives. The removal of the benzyl group can be carried out for example with catalytic hydrogenation or with hydrogen bromide in acetic acid solution, the cleavage of methyl group can be carried out with boron tribromide in dichloromethane solution. The compounds of formula (I) containing free phenolic hydroxy group can be transformed into acyloxy or sulfoxy derivatives with different acylating or sulfonylating agents. The reactions are carried out at room temperature in chlorinated hydrocarbons using acid chloride or acid anhydride as acylating agent in the presence of a base (e.g., triethylamine or sodium carbonate). The carboxylic acid amide derivatives of formula (I) containing a nitro group (I) can be transformed into amines by catalytic hydrogenation and the amines can be further reacted to give acid amides as described for the acylation of phenolic hydroxy groups. Free hydroxy groups can be esterified by acid anhydrides or acid halogenides in the presence of a base.

The carboxylic acids of formula (II) or (IV), the primary or secondary amines of formula (III) or (V) and the halogene compounds of formula (VI) or (VII) are either commercially available or can be synthesized by different known methods. The syntheses of some commercially not available carboxylic acids of formula (II) or (IV) or halogen compounds of (VI) or (VII) are described in the Examples. Following these procedures the other commercially not available carboxylic acids of formula (II) or (IV) or halogen compounds of formula (VI) or (VII) can also be prepared.

EXPERIMENTAL PROTOCOLS

Assessing the Functional NMDA Antagonist Potency of Compounds in Primary Cultures of Rat Cortical Neurons Based on Measuring the Intracellular Calcium Concentration Using a Fluorimeter Plate Reader It is known that during postnatal development the subunit composition of neuronal NMDA receptors is changing. Similar change has been detected in neuronal cell cultures [Eur. J. Neurosci., 10, 1704-1715 (1998)]. According to data in the literature and to our own immunocytochemical examinations neuronal cells cultured for 4-7 days in vitro predominantly express the NR2B subunit, together with NR1 subunit. Therefore, functional test of NMDA antagonism in these cells reflects mainly an action on NR2B subunit containing receptors. Since NMDA receptors are known to be permeable to calcium ions upon excitation, the extent of NMDA receptor activation, and its inhibition by functional antagonists can be characterised by measuring the rise in the intracellular calcium concentration following agonist (NMDA) application onto the cells. Since there is very high sequence homology between rat and human NMDA receptors (99, 95, 97% for NR1, NR2A, and NR2B subunits, respectively), it is believed that there is little, if any, difference in their pharmacological sensitivity. Hence, results obtained with (cloned or native) rat NMDA receptors may be well extrapolated to the human ones.

The intracellular calcium measurements are carried out on primary neocortical cell cultures derived from 17 day old Charles River rat embryos [for the details on the preparation of neocortical cell culture see Johnson, M. I.; Bunge, R. P. (1992): Primary cell cultures of peripheral and central neurons and glia. In: Protocols for Neural Cell Culture, eds: Fedoroff, S.; Richardson A., The Humana Press Inc., 13-38.] After isolation, the cells are plated onto standard 96-well microplates and the cultures are maintained in an atmosphere of 95% air-5% $CO_2$ at 37° C. until testing.

The cultures are used for the intracellular calcium measurements after 4-7 days in vitro. The cells are loaded with a fluorescent $Ca^{2+}$-sensitive dye, Fluo-4/AM (2-2.5 μM) prior to testing. Loading is stopped by washing twice with the solution used also during the measurement (140 mM NaCl, 5 mM KCl, 2 mM $CaCl_2$, 5 mM HEPES [4-(2-hydroxyethyl)-1-piperazineethane-sulfonic acid], 5 mM HEPES-Na, 20 mM glucose, 10 μM glycine, pH=7.4). Then the test compound dissolved in the above solution (90 μl/well) is added. Intracellular calcium measurements are carried out with a plate reader fluorimeter. A rise is induced by application of 40 μM NMDA in Fluo-4-fluorescence that reflects the intracellular calcium concentration. Inhibitory potency of the test compound is assessed by measuring the reduction in the calcium elevation in the presence of different concentrations of the compound. After the measurement, a standard calibration procedure [Meth. Cell. Biol., 40, 155-181 (1994)] is applied to convert the fluorescence data to calcium concentration values.

Inhibitory potency of a compound at a single concentration point is expressed as percent inhibition of the control NMDA response. Sigmoidal concentration-inhibition curves are fitted over the data and $IC_{50}$ values are defined as the concentration that produces half of the maximal inhibition that could be achieved with the compound. Mean $IC_{50}$ values are derived from at least three independent experiments.

Determining Binding of Compounds to NR2B Subunit by [$^3$H]-Ro 25,6981 Binding Assay The method for determining the binding of compounds to NR2B subunit by [$^3$H]-Ro 25,6981 binding assay is essentially similar to that described by Mutel et al. [J. Neurochem., 70, 2147-2155 (1998)] except for incubation temperature and radioligand concentration. Briefly, membranes are isolated from the forebrain of male Wistar rats. They are incubated in the presence and absence of test compound for 2 hours at room temperature. Non-specific binding is determined using 10 μM Ro-25,6981, and is typically less than 7% of the total binding. The applied radioligand ($^3$H-Ro-25,6981) concentration is 4 nM. $IC_{50}$ values (50% inhibitory concentrations) are determined from sigmoidal fits plotted over concentration-displacement curves.

The Biological Activity of the Compounds $IC_{50}$ values for selected examples of compounds of this invention in the functional NMDA antagonism and in the binding tests are listed in Table 1 and compared to those determined for the most potent known reference compounds.

The compounds of this invention exhibit $IC_{50}$ values of less than 50 μM in the functional NMDA antagonism and in the binding tests. Thus the compounds and pharmaceutical compositions of this invention are NR2B subtype specific .NMDA antagonists. Some of the compounds have superior potency compared to the known reference compounds (see Table 1).

NMDA Antagonist/Binding Activity of Compounds on Native Neurons/Neuronal Membranes from Rats

TABLE 1

| ID code of compound | NMDA $IC_{50}$ [μM] | Ro-binding $IC_{50}$ [μM] | Code of reference compound | NMDA $IC_{50}$ [μM] | Ro-binding $IC_{50}$ [μM] |
|---|---|---|---|---|---|
| 70001623 | 0.0007 | 0.0047 | CI-1041 | 0.0066 | 0.004 |
| 70001824 | 0.0014 | 0.0044 | Co-101244 | 0.023 | 0.0033 |
| 70001861 | 0.0024 | 0.0055 | EMD 95885 | 0.035 | 0.0072 |
| 70001620 | 0.0032 | 0.018 | CP 101,606 | 0.041 | 0.0084 |
| 70001825 | 0.006 | 0.0017 | Co-111103 | 0.060 | 0.0084 |
| 70001863 | 0.048 | 0.091 | Ro 25.6981 | 0.159 | 0.0059 |
| 70001844 | 0.113 | 0.214 | ifenprodil | 0.483 | 0.096 |
| 70001712 | 0.164 | 0.029 | | | |
| 70001843 | 0.533 | 0.972 | | | |
| 70001990 | 1.01 | 0.614 | | | |
| 70001894 | 1.33 | 0.121 | | | |
| 70001759 | 4.71 | >30 | | | | wherein for NMDA $IC_{50}$—$IC_{50}$ is determined by the intracellular $Ca^{2+}$-concenartion assay on cortical neurons; and for Ro-binding $IC_{50}$—$IC_{50}$ is determined by the [$^3$H]-Ro 25,6981 binding assay on rat cerebral membranes.

The reference compounds of Table 1 are as follows:
CI-1041—6-{2-[4-(4-fluoro-benzyl)-piperidin-1-yl]-ethanesulfinyl}-3H-benzooxazol-2-one
Co 101244—1-[2-(4-hydroxyphenoxy)ethyl]-4-hydroxy-4-(4-methylbenzyl)piperidine
EMD 95885—6-[3-(4-fluorobenzyl)piperidine-1-yl]propionyl]-2,3-dihydro-benzoxazol-2-on
CP-101,606—(1S,2S)-1-(4-hydroxyphenyl)-2-(4-hydroxy-4-phenylpiperidine-1-yl)-1-propanol
Co-111103—1-[2-(4-hydroxyphenoxy)ethyl]-4-(4-fluorobenzyl)piperidine
Ro 256981—R—(R*,S*)-1-(4-hydroxyphenyl)-2-methyl-3-[4-(phenylmethyl)piperidin-1-yl]-1-propanol.
Ifenprodil—erythro-2-(4-benzylpiperidino)-1-(4-hydroxyphenyl)-1-propanol

Mouse Formalin Test for Measurement of In Vivo Efficacy

Injection of diluted formalin into the hind paw of rats or mouse is known to elicit a biphasic pain related behaviour measured as time spent by licking/biting of the injured paw. The second phase is generally defined as pain related events detected in the 15-60 min. time interval after formalin injection. It is known that NMDA receptors are involved in the second phase of response to formalin injection and this behavioural response is sensitive to blockade of NMDA receptors [Dickenson, A. and Besson J.-M. (Eds.): Chapter 1, pp. 6-7: Animal models of Analgesia; and Chapter 8, pp. 180-183: Mechanism of Central Hypersensitivity: Excitatory Amino Acid Mechanisms and Their Control—In Pharmacology of Pain. Springer-Verlag (Berlin) 1997.] Therefore, we performed the second phase of formalin test to characterise the efficacy of compounds in vivo. Inhibition of the second phase of response is considered to indicate an analgesic effect against chemically-induced persistent pain [Hunskaar, S., et al.: Formalin Test in Mice, a Useful Technique for Evaluating Mild Analgesics, Journal of Neuroscience Methods, 14 (1985) 69-76.] Male albino Charles River NMRI mice (20-25 g) were used. Prior to the experiment any solid food was withdrawn for 16 hours but the animals had free access to 20% glucose solution. The animals were allowed a 1 hour acclimatisation period spent in a glass cylinder (cc. 15 cm in diameter), then moved to an identical cylinder with a mirror placed behind to facilitate observation. The test substances were suspended in 5% tween-80 (10 ml per kg body weight). and administered orally by gavage 15 min before the formalin injection (20 µl of 1% formalin in 0.9% saline injected subcutaneously into the dorsal surface of the right hindpaw). The time spent by licking and biting of the injected paw was measured from 20 to 25 min. after the formalin injection. For the determination of $ED_{50}$ value, various doses (at least five) of the test substances were given to groups of 5 mice and the results expressed as % inhibition time spent by licking relative to a vehicle control group observed on the same day. $ED_{50}$ values (i.e., the dose yielding 50% inhibition) were calculated by Boltzman's sigmoidal curve fitting.

TABLE 2

$ED_{50}$ values of selected compounds

| ID code of compounds | $ED_{50}$ (mg/kg p.o.) |
| --- | --- |
| 45-70001598 | 0.46 |
| 45-70002346 | 0.48 |
| 45-70002233 | 2.4 |
| 45-70002407 | 4.4 |
| 45-70001620 | 6.9 |
| 45-70002863 | 17 |
| CI-1041 | 5.3 mg/kg |
| Co-101244 | >20 mg/kg* |
| EMD 95885 | 5.9 mg/kg |
| CP-101,606 | >20 mg/kg* |
| Co-111103 | >20 mg/kg* |
| Ro-256981 | >20 mg/kg* |

*$ED_{50}$ value was not determined if the inhibition was less than 50% at the dose of 20 mg/kg, p.o.

Disorders which may be beneficially treated with NMDA antagonists include traumatic injury of brain [Neurol. Res., 21, 330-338 (1999)] or spinal cord [Eur. J. Pharmacol., 175, 165-74 (1990)], human immunodeficiency virus (HIV) related neuronal injury [Annu. Rev. Pharmacol. Toxicol., 1998; 38159-77], amyotrophic lateral sclerosis [Neurol. Res., 21, 309-12 (1999)], tolerance and/or dependence to opioid treatment of pain [Brain. Res., 731, 171-181 (1996)], withdrawal syndromes of e.g., alcohol, opioids or cocaine [Drug and Alcohol Depend., 59, 1-15 (2000)], muscular spasm [Neurosci. Lett., 73, 143-148 (1987)], dementia of various origins [Expert Opin. Investig. Drugs, 9, 1397-406 (2000)]. An NMDA antagonist may also be useful to treat cerebral ischemia of any origin (e.g., stroke, heart surgery), chronic neurodegenerative disorders, such as Alzheimer's disease, Parkinson's disease, Huntington's disease, pain (e.g., post-traumatic or postoperative) and chronic pain states, such as neuropathic pain or cancer related pain, epilepsy, anxiety, depression, migraine, psychosis, hypoglycemia, degenerative disorders of the retina (e.g., CMV retinitis), glaucoma, asthma, tinnitus, aminoglycoside antibiotic-induced hearing loss [Drug News Perspect 11, 523-569 (1998) and WO 00/00197 international patent application].

Accordingly, effective amounts of the compounds of the invention may be beneficially used for the treatment of traumatic injury of brain or spinal cord, human immunodeficiency virus (HIV) related neuronal injury, amyotrophic lateral sclerosis, tolerance and/or dependence to opioid treatment of pain, withdrawal syndromes of e.g., alcohol, opioids or cocaine, ischemic CNS disorders, chronic neurodegenerative disorders, such as Alzheimer's disease, Parkinson's disease, Huntington's disease, pain and chronic pain states, such as neuropathic pain or cancer related pain, epilepsy, anxiety, depression, migraine, psychosis, muscular spasm, dementia of various origin, hypoglycemia, degenerative disorders of the retina, glaucoma, asthma, tinnitus, aminoglycoside antibiotic-induced hearing loss.

The compounds of the invention as well as their pharmaceutically acceptable salts can be used as such or suitably in the form of pharmaceutical compositions. These compositions (drugs) can be in solid, liquid or semiliquid form and pharmaceutical adjuvant and auxiliary materials can be added, which are commonly used in practice, such as carriers, excipients, diluents, stabilizers, wetting or emulsifying agents, pH- and osmotic pressure-influencing, flavoring or aromatizing, as well as formulation-promoting or formulation-providing additives.

The dosage required to exert the therapeutical effect can vary within wide limits and will be fitted to the individual requirements in each of the particular cases, depending on the stage of the disease, the condition and the bodyweight of the patient to be treated, as well as the sensitivity of the patient against the active ingredient, route of administration and number of daily treatments. The actual dose of the active ingredient to be used can safely be determined by the attending physician skilled in the art in the knowledge of the patient to be treated.

The pharmaceutical compositions containing the active ingredient according to the present invention usually contain 0.01 to 100 mg of active ingredient in a single dosage unit. It is, of course possible that the amount of the active ingredient in some compositions exceeds the upper or lower limits defined above.

The solid forms of the pharmaceutical compositions can be for example tablets, dragées, capsules, pills or lyophilized powder ampoules useful for the preparation of injections. Liquid compositions are the injectable and infusable compositions, fluid medicines, packing fluids and drops. Semiliquid compositions can be ointments, balsams, creams, shaking mixtures and suppositories.

For the sake of a simple administration it is suitable if the pharmaceutical compositions comprise dosage units containing the amount of the active ingredient to be administered once, or a few multiples or a half, third or fourth part thereof. Such dosage units are e.g., tablets, which can be powdered with grooves promoting the halving or quartering of the tablet in order to exactly administer the required amount of the active ingredient.

Tablets can be coated with an acid-soluble layer in order to assure the release of the active ingredient content after leaving the stomach. Such tablets are enteric-coated. A similar effect can be achieved also by encapsulating the active ingredient.

The pharmaceutical compositions for oral administration can contain, for example, lactose or starch as excipients, sodium carboxymethylcellulose, methylcellulose, polyvinyl pyrrolidine or starch paste as binders or granulating agents. Potato starch or microcrystalline cellulose is added as disintegration agents, but ultraamylopectin or formaldehyde casein can also be used. Talcum, colloidic silicic acid, stearin, calcium or magnesium stearate can be used as antiadhesive and lubricants.

The tablet can be manufactured for example by wet granulation, followed by pressing. The mixed active ingredients and excipients, as well as in given case part of the disintegrants are granulated with an aqueous, alcoholic or aqueous alcoholic solution of the binders in an appropriate equipment, then the granulate is dried. The other disintegrants, lubricants and antiadhesive agents are added to the dried granulate, and the mixture is pressed to a tablet. In given case the tablets are made with halving groove to ease the administration.

The tablets can be made directly from the mixture of the active ingredient and the proper auxiliaries by pressing. In given case, the tablets can be coated by using additives commonly used in the pharmaceutical practice, for example stabilizers, flavoring, coloring agents, such as sugar, cellulose derivatives (e.g., methyl- or ethylcellulose, sodium carboxymethylcellulose, etc), polyvinyl pyrrolidone, calcium phosphate, calcium carbonate, food coloring agents, food laces, aroma agents, iron oxide pigments, etc. In the case of capsules the mixture of the active ingredient and the auxiliaries is filled into capsules.

Liquid oral compositions, for example suspensions, syrups, elixirs can be made by using water, glycols, oils, alcohols, coloring and flavoring agents.

For rectal administration the composition is formulated in suppositories or clysters. The suppository can contain beside the active ingredient a carrier, so called adeps pro suppository. Carriers can be vegetable oils, such as hydrogenated vegetable oils, triglycerides of C12-C18 fatty acids (preferably the carriers under the trade name Witepsol). The active ingredient is homogeneously mixed with the melted adeps pro suppository and the suppositories are moulded.

For parenteral administration the composition is formulated as injection solution. For manufacturing the injection solution the active ingredients are dissolved in distilled water and/or in different organic solvents, such as glycolethers, in given case in the presence of solubilizers, for example polioxyethylensorbitane-monolaurate, -monooleate, or monostearate (Tween 20, Tween 60, Tween 80). The injection solution can also contain different auxiliaries, such as conserving agents, for example ethylendiamine tetraacetate, as well as pH adjusting agents and buffers and in given case local anaesthetic, e.g., lidocain. The injection solution containing the active ingredient of the invention is filtered before it is filled into ampoules, and it is sterilized after filling.

If the active ingredient is hygroscopic, then it can be stabilized by liophylization.

The following examples illustrate the invention without intending to limit the scope of the invention.

EXAMPLE 1

2-[4-(4-Fluoro-benzyl)-piperidin-1-yl]-2-oxo-N-(2-oxo-2,3-dihydro-1H-indol-5-yl)-acetamide (45 70001598)

1a) [4-(4-Fluoro-benzyl)-piperidin-1-yl]-oxo-acetic acid ethyl ester

To a stirred solution of 2.3 g (10 mmol) of 4-(4-fluoro-benzyl)-piperidine hydrochloride [J. Med. Chem., 35, 4903. (1992)] and 4.5 ml (32 mmol) of triethylamine in 80 ml of chloroform 2.5 ml (22 mmol) of ethyl oxalyl chloride in 20 ml of chloroform is added dropwise below 10° C., and the reaction mixture is stirred at room temperature for 10 hours. Then 50 ml of 8% sodium hydrogen carbonate solution is added to the mixture, the organic layer is separated and the water phase is extracted three times with 25 ml of chloroform. The combined organic layers are dried over sodium sulfate, concentrated, the residue is treated with diisopropyl ether and the crystals are filtered to yield 2.1 g (72%) of the title compound. Melting Point: 72-74° C. (diisopropyl ether)

1b) [4-(4-Fluoro-benzyl)-piperidin-1-yl]-oxo-acetic acid

To a stirred solution of 1.91 g (6.5 mmol) of [(4-fluoro-benzyl)-piperidin-1-yl]-oxo-acetic-acid ethyl ester in 15 ml of ethanol is added a solution of 1.18 g (21.1 mmol) of potassium hydroxide in 3 ml of water. The reaction mixture is stirred at room temperature for 6 hours then cooled and acidified with hydrochloric acid. The solid is collected, washed with water to yield 1.68. (97.4%) g of the title compound. Melting Point: 152-154° C. (ethanol-water)

1c) 2-[4-(4-Fluoro-benzyl)-piperidin-1-yl]-2-oxo-N-(2-oxo-2,3-dihydro-1H-indol-5-yl)-acetamide A mixture of 3.2 g (12 mmol) of [4-(4-fluoro-benzyl)-piperidin-1-yl]-oxo-acetic acid, 1.4 ml (10 mmol) of triethylamine, 1.5 g (10 mmol) of 5-amino-1,3-dihydro-indol-2-one [Tetrahedron, 24, 1376. (1957)] 3.8 g (10 mmol) of HBTU [O-benzotriazol-1-yl-N,N,N',N'-tetramethyluronium hexafluorophosphate (Advanced Chem. Tech.)] and 100 ml of dimethylformamide is stirred at room temperature for 24 hours. The reaction mixture is concentrated. Then 150 ml of 8% sodium hydrogencarbonate solution and 150 ml of chloroform is added to the mixture. The organic layer is separated and the water phase is extracted three times with 25 ml of chloroform. The combined organic layers are dried over sodium sulfate, concentrated and the residue is purified by column chromatography using Kieselgel 60 as adsorbent (Merck) and chloroform:methanol=19:1 as eluent to yield 2.67 g (68%) of the title compound. Melting Point: 195-197° C. (diethylether)

EXAMPLE 2

2-[4-(4-Fluoro-benzyl)-piperidin-1-yl]-2-oxo-N-(2-oxo-2,3-dihydro-1H-benzimidazol-5-yl)-acetamide (45 70001623)

A mixture of 2.5 g (9.6 mmol) of [4-(4-fluoro-benzyl)-piperidin-1-yl]-oxo-acetic acid (Example 1b), 1.1 ml (8 mmol) of triethylamine, 1.2 g (8 mmol) of 5-amino-1,3-dihydro-benzimidazol-2-one [J. Amer. Chem. Soc., 80, 1657. (1958)] 3.03 g (8 mmol) of HBTU and 80 ml of dimethylformamide is stirred at room temperature for 24 hours. The reaction mixture is concentrated, then 100 ml of 8% sodium hydrogencarbonate solution is added. The precipitated product is filtered off and recrystallized from methanol to yield 1.51 g (48%) of the title compound. Melting Point: >260° C. (methanol)

EXAMPLE 3

2-[4-(4-Fluoro-benzyl)-piperidin-1-yl]-2-oxo-N-(2-oxo-2,3-dihydro-benzoxazol-6-yl)-acetamide (45 70001620)

The title compound is prepared from [4-(4-fluoro-benzyl)-piperidin-1-yl]-oxo-acetic acid (Example 1b) and 6-amino-3H-benzoxazol-2-one [J. Chem. Soc.,321. (1938)] according to the method described in Example 1c. Melting Point: 224-227° C. (diethylether)

EXAMPLE 4

2-[4-(4-Fluoro-benzyl)-piperidin-1-yl]-2-oxo-N-(2-oxo-2,3-dihydro-benzoxazol-5-yl)-acetamide (45 70001759)

The title compound is prepared from 5-amino-3H-benzoxazol-2-one [J. Med. Chem., 10, 408. (1967)] and [4-(4-fluoro-benzyl)-piperidin-1-yl]-oxo-acetic acid (Example 1b) according to the method described in Example 2. Melting Point: 226-231° C. (water)

EXAMPLE 5

2-(4-Benzyl-piperidin-1-yl]-N-(4-cyano-phenyl)-2-oxo-acetamide (45 70001798)

5a) (4-Benzyl-piperidine-1-yl)-oxo-acetic acid ethyl ester

The title compound is prepared from 4-benzyl-piperidine (Aldrich) and ethyl oxalyl chloride according to the method described in Example 1a. Melting Point: oil 5b) (4-Benzyl-piperidin-1-yl)-oxo-acetic acid The title compound is prepared from (4-benzyl-piperidin-1-yl)-oxo-acetic acid ethyl ester according to the method described in Example 1b. Melting Point: 109-112° C. (ethanol-water)

5c) 2-(4-Benzyl-piperidin-1-yl)-N-(4-cyano-phenyl)-2-oxo-acetamide

The title compound is prepared from 4-amino-benzonitrile (Aldrich) and (4-benzyl-piperidin-1-yl)-oxo-acetic acid according to the method described in Example 2. Melting Point: 166-169° C. (diethylether)

EXAMPLE 6

2-(4-Benzyl-piperidin-1-yl)-2-oxo-N-(2-oxo-2,3-dihydro-1H-indol-5-yl)-acetamide (45 70001823)

The title compound is prepared from (4-benzyl-piperidin-1-yl)-oxo-acetic acid (Example 5b) and 5-amino-1,3-dihydro-indol-2-one according to the method described in Example 2. Melting Point: 115-118° C. (water)

EXAMPLE 7

2-(4-Benzyl-piperidin-1-yl)-2-oxo-N-(2-oxo-2,3-dihydro-1H-benzimidazol-5-yl)-acetamide (45 70001824)

The title compound is prepared from (4-benzyl-piperidin-1-yl)-oxo-acetic acid (Example 5b) and 5-amino-1,3-dihydro-benzimidazol-2-one according to the method described in Example 2. Melting Point: >260° C. (water)

EXAMPLE 8

2-(4-Benzyl-piperidin-1-yl)-2-oxo-N-(2-oxo-2,3-dihydro-benzoxazol-6-yl)-acetamide (45 70001861)

The title compound is prepared from (4-benzyl-piperidin-1-yl)-oxo-acetic acid (Example 5b) and 6-amino-3H-benzoxazol-2-one according to the method described in Example 1c. Melting Point: 190-193° C. (diethylether)

EXAMPLE 9

N-(4-Cyano-phenyl)-2-[4-(4-fluoro-benzyl)-piperidin-1-yl]-2-oxo-acetamide (45 70001946)

The title compound is prepared from 4-amino-benzonitrile and [4-(4-fluoro-benzyl)-piperidin-1-yl]-oxo-acetic acid (Example 1b) according to the method described in Example 1c. Melting Point: 167-169° C. (diethylether)

EXAMPLE 10

2-(4-Benzyl-piperidin-1-yl)-N-(3-nitro-phenyl)-2-oxo-acetamide (45 70001862)

10a) N-(3-Nitro-phenyl)-oxalamic acid

The title compound is prepared from N-(3-nitro-phenyl)-oxalamic acid ethyl ester [J.Chem. Soc., 121, 1501. (1922)] according to the method described in Example 1b. Melting Point: >270° C. (ethanol-water)

10b) 2-(4-Benzyl-piperidin-1-yl)-N-(3-nitro-phenyl)-2-oxo-acetamide

The title compound is prepared from N-(3-nitro-phenyl)-oxalamic acid and 4-benzyl-piperidine according to the method described in Example 1c. Melting Point: 138-140° C. (diethylether)

EXAMPLE 11

N-(3-Amino-phenyl)-2-(4-benzyl-piperidin-1-yl)-2-oxo-acetamide (45 70001945)

A mixture of 1.8 g (4.9 mmol) of 2-(4-benzyl-piperidin-1-yl)-N-(3-nitro-phenyl)-2-oxo-acetamide(Example 10b), 50 ml of dimethylformamide, 0.5 g of 10% Pd/C catalyst is hydrogenated for 2 hours. The catalyst is filtered off, washed with dimethylformamide and the filtrate is concentrated. The residue is treated with diethylether and the precipitated crystals are filtered off to yield 1.41 g (83%) of the title compound. Melting Point: 103-105° C. (diethylether)

EXAMPLE 12

2-(4-Benzyl-piperidin-1-yl)-N-(3-methanesulfonylamino-phenyl)-2-oxo-acetamide (45 70001990)

To a stirred solution of 0.34 g (1 mmol) of N-(3-amino-phenyl)-2-(4-benzyl-piperidin-1-yl)-2-oxo-acetamide (Example 11) and 0.16 ml (2 mmol) of pyridine in 10 ml of dichloromethane 0.16 ml (2 mmol) of methanesulfonyl chloride in 2 ml of dichloromethane is added dropwise below 10° C., and the reaction mixture is stirred at room temperature for 10 hours. Then 50 ml of 8% sodium hydrogencarbonate solution is added to the mixture, the organic layer is separated and the water phase is extracted three times with 10 ml of dichloromethane. The combined organic layers are dried over sodium sulfate, concentrated, the residue is treated with diethylether and the crystals are filtered to yield 0.25 g (30%) of the title compound. Melting Point: 128-130° C. (diethylether)

EXAMPLE 13

2-(4-Benzyl-piperidin-1-yl)-N-(3-hydroxy-phenyl)-2-oxo-acetamide (45 70001991)

The title compound is prepared from (4-benzyl-piperidin-1-yl)-oxo-acetic acid (Example 5b) and 3-aminophenol (Aldrich) according to the method described in Example 2. Melting Point: 158-160° C. (water)

EXAMPLE 14

N-(3-Cyano-phenyl)-2-[4-(4-fluoro-benzyl)-piperidin-1-yl]-2-oxo-acetamide (45 70002057)

The title compound is prepared from [4-(4-fluoro-benzyl)-piperidin-1-yl]-oxo-acetic acid (Example 1b) and 3-aminobenzonitrile (Aldrich) according to the method described in Example 1c. Melting Point: 135-138° C. (diethylether)

EXAMPLE 15

2-[4-(4-Fluoro-benzyl)-piperidin-1-yl]-N-(3-nitro-phenyl)-2-oxo-acetamide (45 70001964)

The title compound is prepared from 4-(4-fluoro-benzyl)-piperidine and N-(3-nitro-phenyl)-oxalamic acid (Example 10a according to the method described in Example 2. Melting Point: 135-138° C. (diethylether)

EXAMPLE 16

N-(3-Amino-phenyl)-2-[4-(4-fluoro-benzyl)-piperidin-1-yl]-2-oxo-acetamide (45 70002019)

The title compound is prepared from 2-[4-(4-fluoro-benzyl)-piperidin-1-yl]-N-(3-nitro-phenyl)-2-oxo-acetamide (Example 15) according to the method described in Example 11. Melting Point: 117-120° C. (diethylether)

EXAMPLE 17

2-[4-(4-Fluoro-benzyl)-piperidin-1-yl]-N-(3-methanesulfonylamino-phenyl)-2-oxo-acetamide (45 70002081)

The title compound is prepared from N-(3-amino-phenyl)-2-[4-(4-fluoro-benzyl)-piperidin-1-yl]-2-oxo-acetamide (Example 16) according to the method described in Example 12. Melting Point: 102-106° C. (diethylether)

EXAMPLE 18

2-(4-Benzyl-piperidin-1-yl)-N-(4-hydroxy-phenyl)-2-oxo-acetamide (45 70002117)

The title compound is prepared from (4-benzyl-piperidin-1-yl)-oxo-acetic acid (Example 5b) and 4-aminophenol (Aldrich) according to the method described in Example 1c. Melting Point: 167-169° C. (diethylether).

EXAMPLE 19

2-(4-Benzyl-piperidin-1-yl)-N-(4-methanesulfonylamino-phenyl)-2-oxo-acetamide (45 70002123)

The title compound is prepared from (4-benzyl-piperidin-1-yl)-oxo-acetic acid (Example 5b) and N-(4-amino-phenyl)-methanesulfonamide [Tetrahedron, 42, 5739. (1986)] according to the method described in Example 2. Melting Point: 221-225° C. (water)

EXAMPLE 20

1-(4-Benzyl-piperidin-1-yl)-N-(1H-indazol-5-yl)-2-oxo-acetamide (45 70001814)

The title compound is prepared from 5-aminoindazol (Aldrich) and (4-benzyl-piperidin-1-yl)-oxo-acetic acid (Example 5b) according to the method described in Example 1c. Melting Point: 204-209° C. (diethylether)

EXAMPLE 21

1-[4-(4-Fluoro-benzyl)-piperidin-1-yl]-N-(1H-indazol-5-yl)-2-oxo-acetamide (45 70001816)

The title compound is prepared from 5-aminoindazol (Aldrich) and [4-(4-fluoro-benzyl)-piperidin-1-yl]-oxo-acetic acid (Example 1b) according to the method described in Example 2. Melting Point: 198-200° C. (diethylether)

EXAMPLE 22

2-[4-(4-Fluoro-benzyl)-piperidin-1-yl]-2-oxo-N-(3-oxo-3,4-dihydro-2H-benzo[1,4]oxazine-7-yl)-acetamide (45 70001818)

The title compound is prepared from 7-amino-4H-benzo[1,4]oxazin-3-one [J. Med. Chem., 32, 1627. (1989)] and [4-(4-fluoro-benzyl)-piperidin-1-yl]-oxo-acetic acid (Example 1b) according to the method described in Example 2. Melting Point: 209-212° C. (diethylether)

EXAMPLE 23

N-(1H-Benzimidazol-5-yl)-2-[4-(4-fluoro-benzyl)-piperidin-1-yl]-2-oxo-acetamide (45 0001820)

The title compound is prepared from (1H-benzimidazol-5yl) amine [Synth. Commun., 29, 2435. (1999)] and [4-(4-fluoro-benzyl)-piperidin-1-yl]-oxo-acetic acid Example 1b) according to the method described in Example 1c. Melting Point: 104-110° C. (diethylether)

EXAMPLE 24

2-(4-Benzyl-piperidin-1-yl)-2-oxo-N-(3-oxo-3,4-dihydro-2H-benzo [1,4]oxazin-7-yl)-acetamide (45 70001844)

The title compound is prepared from 7-amino-4H-benzo[1,4]oxazin-3-one and (4-benzyl-piperidin-1-yl)-oxo-acetic acid (Example 5b) according to the method described in Example 2. Melting Point: 123-126° C. (diethylether)

EXAMPLE 25

2-[4-(4-Fluoro-benzyl)-piperidin-1-yl]-N-(1H-indazol-6-yl)-2-oxo-acetamide (45 70001815)

The title compound is prepared from 6-aminoindazol (Aldrich) and [4-(4-fluoro-benzyl)-piperidin-1-yl]-oxo-acetic acid (Example 1b) according to the method described in Example 2. Melting Point: 162-164° C. (diethylether)

EXAMPLE 26

2-Oxo-N-(2-oxo-2,3-dihydro-1H-indol-5-yl)-2-(4-p-tolyloxy-piperidin-1-yl)-acetamide (45 70002274)

26a) Oxo-(4-p-tolyloxy-piperidin-1-yl)-acetic acid ethyl ester

The title compound is prepared from 4-p-tolyloxy-piperidine [J. Med. Chem., 21, 309. (1978)] and ethyl oxalyl chloride according to the method described in Example 1a. Melting Point: oil.

26b) Oxo-(4-p-tolyloxy-piperidin-1-yl)-acetic acid

The title compound is prepared from oxo-(4-p-tolyloxy-piperidin-1-yl)-acetic acid ethyl ester according to the method described in Example 1b. Melting Point: 109-112° C. (ethanol-water).

26c) 2-Oxo-N-(2-oxo-2,3-dihydro-1H-indol-5-yl)-2-(4-p-tolyloxy-piperidin-1-yl)-acetamide The title compound is prepared from oxo-(4-p-tolyloxy-piperidin-1-yl)-acetic acid and 5-amino-1,3-dihydro-indol-2-one according to the method described in Example 2. The filtered crystals are purified by column chromatography using Kieselgel 60 (Merck) as adsorbent and toluene:methanol=4:1 as eluent. Melting Point: 176-178° C. (diethyl ether)

EXAMPLE 27

2-[4-(4-Fluoro-phenoxy)-piperidin-1-yl]-2-oxo-N-(2-oxo-2,3-dihydro-1H-indol-5-yl)-acetamide (45 70002365)

27a) [4-(4-Fluoro-phenoxy)-piperidin-1-yl]-oxo-acetic acid ethyl ester

The title compound is prepared from 4-(4-fluoro-phenoxy)-piperidine (U.S. Pat. No. 3,260,723) and ethyl oxalyl chloride according to the method described in Example 1a. Melting Point: oil 27b) [4-(4-Fluoro-phenoxy)-piperidin-1-yl]-oxo-acetic acid The title compound is prepared from [4-(4-fluoro-phenoxy)-piperidin-1-yl]-oxo-acetic acid ethyl ester according to the method described in Example 1b. Melting Point: 147-149° C. (ethanol-water)

27c) 2-[4-(4-Fluoro-phenoxy)-piperidin-1-yl]-2-oxo-N-(2-oxo-2,3-dihydro-1H-indol-5acetamide The title compound is prepared from [4-(4-fluoro-phenoxy)-piperidin-1-yl]-oxo-acetic acid and 5-amino-1,3-dihydro-indol-2-one according to the method described in Example 2. The filtered crystals are purified by column chromatography using Kieselgel 60 (Merck) as adsorbent and toluene:methanol=4:1 as eluent. Melting Point: 209-211° C. (diethyl ether)

EXAMPLE 28

2-Oxo-N-(2-oxo-2,3-dihydro-1H-indol-5-yl)-2-(4-phenoxy-piperidin-1-yl)-acetamide (45 70002366)

28a) Oxo-(4-phenoxy-piperidin-1-yl)-acetic acid ethyl ester

The title compound is prepared from 4-phenoxy-piperidine (J. Med. Chem., 17, 1000. (1974)] and ethyl oxalyl chloride according to the method described in Example 1a. Melting Point: oil.

28b) Oxo-(4-phenoxy-piperidin-1-yl)-acetic acid

The title compound is prepared from oxo-(4-phenoxy-piperidin-1-yl)-acetic acid ethyl ester according to the method described in Example 1b. Melting Point: 109-112° C. (ethanol-water).

28c) 2-Oxo-N-(2-oxo-2,3-dihydro-1H-indol-5-yl)-2-(4-phenoxy-piperidin-1-yl)-acetamide The title compound is prepared from oxo-(4-phenoxy-piperidin-1-yl)-acetic acid and 5-amino-1,3-dihydro-indol-2-one according to the method described in Example 2. The filtered crystals are purified by column chromatography using Kieselgel 60 (Merck) as adsorbent and toluene:methanol=4:1 as eluent. Melting Point: 78-81° C. (diethyl ether)

EXAMPLE 29

2-[4-(4-Chloro-phenoxy)-piperidin-1-yl]-2-oxo-N-(2-oxo-2,3-dihydro-1H-indol-5-yl)-acetamide (45 70002367)

29a) 4-(4-Chloro-phenoxy)-piperidin-1-carboxylic acid tert-butyl ester

Under argon, to a stirred solution 10.0 g (49.7 mmol) of 4-hydroxy-piperidin-1-carboxylic acid tert-butyl ester [Bioorg. Med. Chem. Lett. 10, 2815. (2000)] in 80 ml of dimethylformamide 3.0 g (60%, 75 mmol) of sodium hydride is added. The reaction mixture is stirred for 1 hour at 40° C., then 5.3 ml (49.7 mmol) of 1-chloro-4-fluoro-benzene (Aldrich) in 20 ml dimethylformamide is added dropwise at 20° C. The reaction mixture is stirred for 4 hours at 80° C., cooled to 20° C., 1 ml of ethanol is added dropwise, poured into 100 ml of water and extracted with ethyl acetate. The organic layer is dried over sodium sulfate and concentrated. The residue is purified by column chromatography using Kieselgel 60 (Merck) as adsorbent and ethyl acetate as eluent to yield 11.07 g (75.5%) of the title compound. Melting Point: oil 29b) 4-(4-Chloro-phenoxy)-piperidine hydrochloride To a solution of 150 ml of 2.5 M hydrochloric acid in ethyl acetate 11.07 g (37.5 mmol) of 4-(4-chloro-phenoxy)-piperidin-1-carboxylic acid tert-butyl ester is added. The reaction mixture is stirred for 3 hours at 20° C., then concentrated to 50 ml. The precipitated crystals are filtered off, washed with ethyl acetate to yield 7.0 g (75.2%) of the title compound. Melting Point: 194-196° C.

29c) [4-(4-Chloro-phenoxy)-piperidin-1-yl]-oxo-acetic acid ethyl ester

The title compound is prepared from 4-(4-chloro-phenoxy)-piperidine and ethyl oxalyl chloride according to the method described in Example 1a. Melting Point: oil.

29d) [4-(4-Chloro-phenoxy)-piperidin-1-yl]-oxo-acetic acid

The title compound is prepared from [4-(4-fluoro-phenoxy)-piperidin-1-yl]-oxo-acetic acid ethyl ester according to the method described in Example 1b. Melting Point: 144-145° C. (ethanol-water)

29e) 2-[4-(4-Chloro-phenoxy)-piperidin-1-yl]-2-oxo-N-(2-oxo-2,3-dihydro-1H-indol-5yl)-acetamide The title compound is prepared from [4-(4-chloro-phenoxy)-piperidin-1-yl]-oxo-acetic acid and 5-amino-1,3-dihydro-indol-2-one according to the method described in Example 2. The filtered crystals are purified by column chromatography using Kieselgel 60 (Merck) as adsorbent and toluene:methanol=4:1 as eluent. Melting Point: 198-200° C. (diethyl ether)

EXAMPLE 30

2-[4-(4-Chloro-phenoxy)-piperidin-1-yl]-2-oxo-N-(2-oxo-2,3-dihydro-1H-benzimidazol-5-yl)-acetamide (45 70002405)

The title compound is prepared from [4-(4-chloro-phenoxy)-piperidin-1-yl]-oxo-acetic acid (Example 29d) and 5-amino-1,3-dihydro-benzimidazol-2-one according to the method described in Example 2. The filtered crystals are purified by column chromatography using Kieselgel 60 (Merck) as adsorbent and chloroform:methanol=10:1 as eluent. Melting Point: 286-288° C. (isopropanol)

EXAMPLE 31

2-[4-(4-Chloro-phenoxy)-piperidin-1-yl]-2-oxo-N-(2-oxo-2,3-dihydro-benzoxazol-6-yl)-acetamide (45 70002407)

The title compound is prepared from [4-(4-chloro-phenoxy)-piperidin-1-yl]-oxo-acetic acid (Example 29d) and 6-amino-3H-benzoxazol-2-one according to the method described in Example 2. The filtered crystals are purified by column chromatography using Kieselgel 60 (Merck) as adsorbent and toluene:methanol=4:1 as eluent. Melting Point: 242-244° C. (isopropanol)

EXAMPLE 32

2-(4-Benzyl-piperidin-1-yl)-2-oxo-N-(2-thioxo-2,3-dihydro-benzoxazol-6-yl)-acetamide (45 70002446)

To a stirred solution of 0.3 g (1.8 mmol) of 6-amino-3H-benzoxazole-2-thione [J. Org. Chem., 19; 758. (1954)] and 0.6 ml (4.3 mmol) of triethylamine in 20 ml of chloroform 0.5 g (1.8 mmol) of (4-benzyl-piperidine-1-yl)-oxo-acetyl chloride (Example 38c) in 10 ml of chloroform is added dropwise at 0° C. The reaction mixture is stirred at room temperature for 1 hour, then washed with water and the organic layer is concentrated. The residue is purified by column chromatography using Kieselgel 60 (Merck) as adsorbent and toluene:methanol=4:1 as eluent to yield 0.46 g (61.9%) of the title compound. Melting Point: 203° C. (isopropanol)

EXAMPLE 33

2-[4-(4-Chloro-benzyl)-piperidin-1-yl]-2-oxo-N-(2-oxo-2,3-dihydro-benzoxazol-6-yl)-acetamide (45 70002466)

33a) [4-(4-Chloro-benzyl)-piperidin-1-yl]-oxo-acetic acid ethyl ester

The title compound is prepared from 4-(4-chloro-benzyl)-piperidine (C.A.77, 34266 w) and ethyl oxalyl chloride according to the method described in Example 1a. Melting Point: oil 33b) [4-(4-Chloro-benzyl)-piperidin-1-yl]-oxo-acetic acid The title compound is prepared from [4-(4-chloro-benzyl)-piperidin-1-yl]-oxo-acetic acid ethyl ester according to the method described in Example 1b. Melting Point: 147-148° C. (ethanol-water).

33c) 2-[4-(4-Chloro-benzyl)-piperidin-1-yl]-2-oxo-N-(2-oxo-2,3-dihydro-benzoxazol-6-yl)-acetamide The title compound is prepared from [4-(4-chloro-benzyl)-piperidin-1-yl]-oxo-acetic acid and 6-amino-3H-benzoxazol-2-one according to the method described in Example 2. The filtered crystals are purified by column chromatography using Kieselgel 60 (Merck) as adsorbent and toluene:methanol=4:1 as eluent. Melting Point: 215° C. (isopropanol)

EXAMPLE 34

2-[4-(4-Chloro-benzyl)-piperidin-1-yl]-2-oxo-N-(2-oxo-2,3-dihydro-1H-benzimidazol-5-yl)-acetamide (45 70002467)

The title compound is prepared from [4-(4-chloro-benzyl)-piperidin-1-yl]-oxo-acetic acid (Example 33b) and 5-amino-1,3-dihydro-benzimidazol-2-one according to the method described in Example 2. The filtered crystals are purified by column chromatography using Kieselgel 60 (Merck) as adsorbent and toluene:methanol=4:1 as eluent. Melting Point: 299-300° C. (isopropanol)

EXAMPLE 35

2-Oxo-N-(2-oxo-2,3-dihydro-benzoxazol-6-yl)-2-(4-p-tolyloxy-piperidin-1-yl)-acetamide (45 70002480)

The title compound is prepared from oxo-(4-p-tolyloxy-piperidin-1-yl)-acetic acid (Example 26b) and 6-amino-3H-benzoxazol-2-one according to the method described in Example 2. The filtered crystals are purified by column chromatography using Kieselgel 60 (Merck) as adsorbent and toluene:methanol=4:1 as eluent. Melting Point: 203° C. (isopropanol)

EXAMPLE 36

2-Oxo-N-(2-oxo-2,3-dihydro-1H-benzimidazol-6-yl)-2-(4-p-tolyloxy-piperidin-1-yl)-acetamide (45 70002481)

The title compound is prepared from oxo-(4-p-tolyloxy-piperidin-1-yl)-acetic acid (Example 26b) and 5-amino-1,3-dihydro-benzimidazol-2-one according to the method described in Example 2. The filtered crystals are purified by column chromatography using Kieselgel 60 (Merck) as adsorbent and toluene:methanol=4:1 as eluent. Melting Point: 294° C. (isopropanol)

EXAMPLE 37

2-[4-(4-Chloro-benzyl)-piperidin-1-yl]-2-oxo-N-(2-oxo-2,3-dihydro-1H-indol-5-yl)-acetamide (45 70002486)

The title compound is prepared from [4-(4-chloro-benzyl)-piperidin-1-yl]-oxo-acetic acid (Example 33b) and 5-amino-1,3-dihydro-indol-2-one according to the method described in Example 2. The filtered crystals are purified by column chromatography using Kieselgel 60 (Merck) as adsorbent and toluene:methanol=4:1 as eluent. Melting Point: 195° C. (isopropanol-diethyl ether)

EXAMPLE 38

2-(4-Benzyl-piperidin-1-yl)-N-(2,3-dihydro-1H-indol-5-yl)-2-oxo-acetamide (45 70002497)

38a) 5-Nitro-2,3-dihydro-indol-1-carboxylic acid tert-butyl ester

A mixture of 10.0 g (61.0 mmol) of 5-nitro-2,3-dihydro-1H-indole (Aldrich), 100 ml of dichloromethane, 16.5 g (94.8 mmol) of di-tert-butyl dicarbonate, 13.2 ml (94.8 mmol) of trietylamine and 0.2 g (1.6 mmol) of 4-(dimethylamino)-pyridine is stirred at room temperature for 16 hours. The reaction mixture is washed with water, dried over sodium sulfate and concentrated to yield 15.3 g (99.5%) of the title compound. The crude product is used in the next step.

38b) 5-Amino-2,3-dihydro-indol-1-carboxylic acid tert-butyl ester

A mixture of 15.3 g (60.7 mmol) of 5-nitro-2,3-dihydro-indol-1-carboxylic acid tert-butyl ester, 200 ml of methanol, 200 ml of tetrahydrofuran and 1 g of 10% Pd/C catalyst is hydrogenated. After completion of the reaction, the catalyst is filtered off, washed with tetrahydrofuran and the filtrate is concentrated. The residue is treated with a mixture of diisopropyl ether and hexane and the precipitated crystals are filtered off to yield 12.2 g (90.5%) of the title compound. Melting Point: 75-76° C. (isopropyl ether-hexane)

38c) (4-benzyl-piperidin-1-yl)-oxo-acetyl chloride

A mixture of 28.78 g (116.3 mmol) of (4-benzyl-piperidin-1-yl)-oxo-acetic acid_(Example 5b) and 50 ml of thionyl chloride is refluxed for 2 hours. The reaction mixture is concentrated to yield 30.5 g (98.6%) of the title compound as a solid. The crude products is used in the next step.

38d) 5-[2-(4-Benzyl-piperidin-1-yl)-2-oxo-acetylamino]-2,3-dihydro-indol-1-carboxylic acid tert-butyl ester To a stirred solution of 0.5 g (2.25 mmol) of 5-amino-2,3-dihydro-indole-1-carboxylic acid tert-butyl ester and 0.4 ml (2.8 mmol) of triethylamine in 20 ml of chloroform 0.7 g (2.6 mmol) of (4-benzyl-piperidin-1-yl)-oxo-acetyl chloride in 10 ml of chloroform is added dropwise at 0° C. The reaction mixture is stirred at room temperature for 1 hour, then washed with water and the organic layer is concentrated. The residue is purified by column chromatography using Kieselgel 60 (Merck) as adsorbent and toluene:methanol=4:1 as eluent to yield 0.9 g (88.7%) of the title compound as solid. The crude product is used in the next step.

38e) 2-(4-Benzyl-piperidin-1-yl)-N-(2,3-dihydro-1H-indol-5-yl)-2-oxo-acetamide

To a solution of 10 ml of 2.5 M hydrochloric acid in ethyl acetate 0.9 g (2.0 mmol) of 5-[2-(4-benzyl-piperidin-1-yl)-2-oxo-acetylamino]-2,3-dihydro-indol-1-carboxylic acid tert-butyl ester is added. The reaction mixture is stirred for 3 hours at 20° C., then concentrated. The product is transformed into base form with 2 M sodium carbonate solution, extracted with chloroform, the organic layer is concentrated and the residue is dried to yield 0.45 g (64.1%) of the title compound. Melting Point: 152° C.

EXAMPLE 39

N-(2-Amino-3H-benzimidazol-5-yl)-2-(4-benzyl-piperidin-1-yl)-2-oxo-acetamide trifluoroacetate (45 70002545)

39a) (5-Nitro-1H-benzimidazol-2-yl)-carbamic acid tert-butyl ester (6-Nitro-1H-benzimidazol-2-yl)-carbamic acid tert-butyl ester A mixture of 11.86 g (39.4 mmol) of 5-nitro-1(3)H-benzimidazol-2-ylamine nitrate (U.S. Pat. No. 2,324,123), 150 ml of dichloromethane, 11.0 g (50.4 mmol) of di-tert-butyl dicarbonate and 14.0 ml (100.6 mmol) of trietylamine is stirred at room temperature for 16 hours. The reaction mixture is washed with water, dried over sodium sulfate and concentrated. The residue is crystallized with isopropanol to yield 13.3 g (97.2%) of a 1:1 mixture of the title compounds as solid. Melting Point: 151-152° C. (isopropanol)

39b) (5-Amino-1H-benzimidazol-2-yl)-carbamic acid tert-butyl ester(6-Amino-1H-benzimidazol-2-yl)-carbamic acid tert-butyl ester A mixture of 13.3 g (47.8 mmol) of (5-nitro-1H-benzoimidazol-2-yl)-carbamic acid tert-butyl ester and (6-nitro-1H-benzimidazol-2-yl)-carbamic acid tert-butyl ester, 100 ml of methanol, 100 ml of tetrahydrofuran and 1 g of 10% Pd/C catalyst is hydrogenated. After completion of the reaction, the catalyst is filtered off, washed with tetrahydrofuran and the filtrate is concentrated. The residue is purified by column chromatography using Kieselgel 60 (Merck) as adsorbent and chloroform:methanol=10:1 as eluent to yield 4.72 g (40.4%) of (6-amino-1H-benzoimidazol-2-yl)-carbamic acid tert-butyl ester (Rf. 0.5), Melting Point: 159° C. (diethyl ether) and 4.2 g (36.0%) of (5-amino-1H-benzoimidazol-2-yl)-carbamic acid tert-butyl ester (Rf. 0.4) Melting Point: 168° C. (diethyl ether)

39c) {5-[2-(4-Benzyl-piperidin-1-yl)-2-oxo-acetylamino]-1H-benzoimidazol-2-yl}-carbamic acid tert-butyl ester To a stirred solution of 1.0 g (4.06 mmol) of (6-amino-1H-benzimidazol-2-yl)-carbamic acid tert-butyl ester and 0.8 ml (5.7 mmol) of triethylamine in 30 ml of chloroform 1.5 g (5.6 mmol) of (4-benzyl-piperidin-1-yl)-oxo-acetyl chloride (Example 38c) in 20 ml of chloroform is added dropwise at 0° C. The reaction mixture is stirred at room temperature for 1 hour, then washed with water and the organic layer is concentrated. The residue is crystallized with a mixture of chloroform-methanol=10:1 to yield 1.3 g (67.1%) of the title compound. Melting Point: 192° C. (chloroform-methanol=10:1).

39d) N-(2-Amino-3H-benzimidazol-5-yl)-2-(4-benzyl-piperidin-1-yl)-2-oxo-acetamide trifluoroacetate To a solution of 5 ml of 5% trifluoroacetic acid in dichloromethane 0.8 g (1.67 mmol) of {5-[2-(4-benzyl-piperidin-1-yl)-2-oxo-acetylamino]-1H-benzimidazol-2-yl}-carbamic acid tert-butyl ester is added. The reaction mixture is stirred for 48 hours at 20° C. The precipitated crystals are filtered off and washed with dichloromethane to yield 0.8 g (97.1%) of the title compound. Melting Point: 121° C.

EXAMPLE 40

N-(2-Amino-benzthiazol-6-yl)-2-(4-benzyl-piperidin-1-yl)-2-oxo-acetamide (45 70002579)

The title compound is prepared from (4-benzyl-piperidin-1-yl)-oxo-acetic acid (Example 5b) and 2,6-diamino-benzthiazole [Arch. Pharm., 13, 48. (1935)] according to the method described in Example 2. The filtered crystals are purified by column chromatography using Kieselgel 60 (Merck) as adsorbent and toluene:methanol=4:1 as eluent. Melting Point: 203° C. (isopropanol)

EXAMPLE 41

2-(4-Benzyl-piperidin-1-yl)-N-(2,2-dioxo-2,3-dihydro-1H-2λ$^6$-benzo[c]isothiazol-5-yl)-2-oxo-acetamide (45 70002724)

The title compound is prepared from (4-benzyl-piperidin-1-yl)-oxo-acetic acid (Example 5b) and 5-amino-1,3-dihydro-2,1-benzisothiazole-2,2-dioxide [J. Het. Chem., 23, 1645. (1986)] according to the method described in Example 2. The filtered crystals are purified by column chromatography using Kieselgel 60 (Merck) as adsorbent and toluene:methanol=4:1 as eluent. Melting Point: 181-182° C. (isopropanol)

EXAMPLE 42

2-[4-(4-tert-Butyl-benzyl)-piperidin-1-yl]-2-oxo-N-(2-oxo-2,3-dihydro-benzoxazol-6-yl)-acetamide (45 70002797)

42a) [4-(4-tert-Butyl-benzyl)-piperidin-1-yl]-oxo-acetic acid ethyl ester

The title compound is prepared from 4-(4-tert-butyl-benzyl)-piperidine [J. Org. Chem. 64, 3763. (1999)] and ethyl oxalyl chloride according to the method described in Example 1a. Melting Point: oil 42b) [4-(4-tert-Butyl-benzyl)-piperidin-1-yl]-oxo-acetic acid The title compound is prepared from [4-(4-tert-butyl-benzyl)-piperidin-1-yl]-oxo-acetic acid ethyl ester according to the method described in Example 1b. Melting Point: oil.

42c) 2-[4-(4-tert-Butyl-benzyl)-piperidin-1-yl]-2-oxo-N-(2-oxo-2,3-dihydro-benzoxazol-6-yl)-acetamide The title compound is prepared from [4-(4-tert-butyl-benzyl)-piperidin-1-yl]-oxo-acetic acid and 6-amino-3H-benzoxazol-2-one according to the method described in Example 2. The filtered crystals are purified by column chromatography using Kieselgel 60 (Merck) as adsorbent and toluene:methanol=4:1 as eluent. Melting Point: 168° C. (diethylether-hexane-diisopropyl ether).

EXAMPLE 43

2-[4-(4-Cyano-benzyl)-piperidin-1-yl]-2-oxo-N-(2-oxo-2,3-dihydro-benzoxazol-6-yl)-acetamide (45 70002844)

43a) 4-(1-Benzyl-piperidin-4-ylidenemethyl)-benzonitrile

Under argon, to a stirred solution of 5.0 g (26.4 mmol) of N-benzyl-4-piperidone (Aldrich) and 7.0 g (27.6 mmol) of (4-cyano-benzyl)-phosphoric acid diethyl ester [J. Chem. Soc. Perkin Trans 2., 3, 395. (2001)]) in 50 ml of dimethylformamide 1.5 g (60%, 37.5 mmol) of sodium hydride is added at 0° C. The reaction mixture is stirred for 4 hours at 20° C., 1 ml of ethanol is added dropwise, poured into 100 ml of water and extracted with diethylether. The organic layer is dried over sodium sulfate and concentrated. The crude product is used in the next step. Melting Point: oil.

43b) 4-(1-Benzyl-piperidin-4-ylmethyl)-benzonitrile

A mixture of 8.25 g (28.6 mmol) of 4-(1-benzyl-piperidin-4-ylidenemethyl)-benzonitrile, 200 ml of ethanol and 0.5 g of 10% Pd/C catalyst is hydrogenated. After completion of the reaction, the catalyst is filtered off, washed with tetrahydrofuran and the filtrate is concentrated. The residue is purified by column chromatography using Kieselgel 60 (Merck) as adsorbent and toluene:methanol=4:1 as eluent. Melting Point: 95-96° C. (diisopropyl ether).

43c) 4-Piperidin-4-ylmethyl-benzonitrile hydrochloride

To a stirred solution of 0.5 g (1.72 mmol) of 4-(1-benzyl-piperidin-4-ylmethyl)-benzonitrile in 3 ml of dichloroethan 0.2 ml (1.85 mmol) of 1-chloroethyl-chloroformate is added dropwise at 0° C. The reaction mixture is stirred at 0° C. for 1h and refluxed for 8 hours, then concentrated and the residue is refluxed in 10 ml of methanol. The reaction mixture is concentrated and the residue is crystallized with isopropanol to yield 0.384 g (94.4%) of the title compound. Melting Point: 194° C. (isopropanol).

43d) N-(2-Oxo-2,3-dihydro-benzoxazol-6-yl)-oxalamic acid ethyl ester

The title compound is prepared from 6-amino-3H-benzoxazol-2-one and ethyl oxalyl chloride according to the method described in Example 1a. Melting Point: 180-186° C.

43e) N-(2-Oxo-2,3-dihydro-benzoxazol-6-yl)-oxalamic acid

The title compound is prepared from N-(2-oxo-2,3-dihydro-benzoxazol-6-yl)-oxalamic acid ethyl ester according to the method described in Example 1b. Melting Point: 254° C. (ethanol-water)

43f) 2-[4-(4-Cyano-benzyl)-piperidin-1-yl]-2-oxo-N-(2-oxo-2,3-dihydro-benzoxazol-6-yl)-acetamide To a mixture of 0.3g (1.5 mmol) of N-(2-oxo-2,3-dihydro-benzoxazol-6-yl)-oxalamic acid, 0.165 ml (1.5 mmol) of N-methyl-morpholine in 8 ml of dimethylformamid 0.2 ml (1.5 mmol) of isobutyl-chloroformate is added dropwise at 0° C. and the mixture is stirred at 0° C. for 1 hour. Then 0.333 g (1.4 mmol) of 4-piperidin-4-ylmethyl-benzonitrile hydrochloride and 0.165 ml (1.5 mmol) of N-methyl-morpholine are added and the reaction mixture is stirred at 0° C. for 1 hour, at room temperature for 16 hours. The reaction mixture is concentrated and the residue is purified by column chromatography using Kieselgel 60 (Merck) as adsorbent and toluene:methanol=4:1 as eluent to yield 0.045 g (8.0%) of the title compound. Rf.: 0.4. Melting Point: 259-260° C. (isopropanol).

EXAMPLE 44

2-Oxo-N-(2-oxo-2,3-dihydro-benzoxazol-6-yl)-2-[4-(4-trifluoromethyl-benzyl)-piperidin-1-yl]-acetamide (45 70002930)

The title compound is prepared from 4-(4-trifluoromethyl-benzyl)-piperidine [J. Org. Chem., 64, 3763. (1999)] and N-(2-oxo-2,3-dihydro-benzoxazol-6-yl)-oxalamic acid (Example 43e) according to the method described in Example 43f. The residue is purified by column chromatography using Kieselgel 60 (Merck) as adsorbent and toluene:methanol=4:1 as eluent. Melting Point: 217° C. (isopropanol)

EXAMPLE 45

2-[4-(2,4-Difluoro-benzyl)-piperidin-1-yl]-2-oxo-N-(2-oxo-2,3-dihydro-benzoxazol-6-yl)-acetamide (45 70002931)

45a) 4-(2,4-Difluoro-benzylidene)-piperidin-1-carboxylic acid tert-butyl ester

The title compound is prepared from N-(tert-butoxycarbonyl)-4-piperidone and (2,4-difluoro-benzyl)-phosphoric acid diethyl ester [Eur. J. Med. Chim. Ther., 27, 845. (1992)] according to the method described in Example 43a. The residue is purified by column chromatography using Kieselgel 60 (Merck) as adsorbent and hexane:ethyl acetate=4:1 as eluent. Melting Point: oil 45b) 4-(2,4-Difluoro-benzyl)-piperidin-1-carboxylic acid tert-butyl ester The title compound is prepared from 4-(2,4-difluoro-benzylidene)-piperidin-1-carboxylic acid tert-butyl ester according to the method described in Example 43a. The crude product is used in the next step. Melting Point: oil 45c) 4-(2,4-Difluoro-benzyl)-piperidine The title compound is prepared from 4-(2,4-difluoro-benzyl)-piperidin-1-carboxylic acid tert-butyl ester according to the method described in Example 29b. Melting Point: 191° C. (ethyl acetate-diethyl ether)

45d) 2-[4-(2,4-Difluoro-benzyl)-piperidin-1-yl]-2-oxo-N-(2-oxo-2,3-dihydro-benzoxazol-6-yl)-acetamide The title compound is prepared from 4-(2,4-difluoro-benzyl)-piperidine and N-(2-oxo-2,3-dihydro-benzoxazol-6-yl)-oxalamic acid (Example 43e) according to the method described in Example 43f. The residue is purified by column chromatography using Kieselgel 60 (Merck) as adsorbent and toluene:methanol=4:1 as eluent. Melting Point: 231° C. (isopropanol)

EXAMPLE 46

N-(2,2-Dioxo-2,3-dihydro-1H-2λ⁶-benzo[c]isothiazol-5-yl)-2-[4-(4-fluoro-benzyl)-piperidin-1-yl]-2-oxo-acetamide (45 70002966)

The title compound is prepared from [4-(4-fluoro-benzyl)piperidin-1-yl]-oxo-acetic acid (Example 1a) and 5-amino-1,3-dihydro-2,1-benzisothiazole-2,2-dioxide according to the method described in Example 2. The filtered crystals are purified by column chromatography using Kieselgel 60 (Merck) as adsorbent and toluene:methanol=4:1 as eluent. Melting Point: 183-184° C. (isopropanol)

EXAMPLE 47

2-[4-(3,4-Difluoro-benzyl)-piperidin-1-yl]-2-oxo-N-(2-oxo-2,3-dihydro-benzoxazol-6-yl)-acetamide (45 70002967)

The title compound is prepared from 4-(3,4-difluoro-benzyl)-piperidine [J. Org. Chem., 64, 3763. (1999)] and N-(2-oxo-2,3-dihydro-benzoxazol-6-yl)-oxalamic acid (Example 43e) according to the method described in Example 43f. The residue is purified by column chromatography using Kieselgel 60 (Merck) as adsorbent and toluene:methanol=4:1 as eluent. Melting Point: 233° C. (isopropanol)

EXAMPLE 48

2-(4-Benzyl-piperidin-1-yl)-2-oxo-N-(2-trifluoromethyl-1H-benzoimidazol-5-yl)-acetamide (45 70002968)

The title compound is prepared from (4-benzyl-piperidin-1-yl)-oxo-acetic acid (Example 5b) and 2-trifluoromethyl-1(3)H-benzimidazol-5-ylamine (NL 6501323, CA 66; 28771) according to the method described in Example 2. The filtered crystals are purified by column chromatography using Kieselgel 60 (Merck) as adsorbent and toluene:methanol=4:1 as eluent. Melting Point: 142° C. (isopropanol).

EXAMPLE 49

2-[4-(4-Fluoro-benzyl)-piperidin-1-yl]-2-oxo-N-(3-oxo-3,4-dihydro-2H-benzo[1,4]oxazin-6-yl)-acetamide (45 70001819)

The title compound is prepared from 6-amino-4H-benzo[1,4]oxazin-3-one [Indian J. Chem. Sect. B, 24, 1263. (1985)] and [4-(4-fluoro-benzyl)-piperidin-1-yl]-oxo-acetic acid (Example 1b) according to the method described in Example 2. Melting Point: 197-200° C. (diethylether)

EXAMPLE 50

2-(4-Benzyl-piperidin-1-yl)-2-oxo-N-(3-oxo-3,4-dihydro-2H-benzo[1,4]oxazin-6-yl)-acetamide (45 70001845)

The title compound is prepared from 6-amino-4H-benzo[1,4]oxazin-3-one and (4-benzyl-piperidin-1-yl)-oxo-acetic acid (Example 5b) according to the method described in Example 1c. Melting Point: 186-187° C. (diethylether)

EXAMPLE 51

2-(4-Benzyl-piperidin-1-yl)-N-(1H-benzimidazol-5-yl) 2-oxo-acetamide (45 70001846)

The title compound is prepared from 5-amino-benzimidazole and (4-benzyl-piperidin-1-yl)-oxo-acetic acid (Example 5b) according to the method described in Example 1c. Melting Point: 85-87° C. (diethylether)

EXAMPLE 52

2-(4-Benzyl-piperidin-1-yl)-N-(1H-indazol-6-yl)-2-oxo-acetamide (45 70001878)

The title compound is prepared from 6-aminoindazol (Aldrich) and (4-benzyl-piperidin-1-yl)-oxo-acetic acid (Example 5b) according to the method described in Example 1c. Melting Point: 160-164° C. (diethylether).

EXAMPLE 53

2-(4-Benzyloxy-piperidin-1-yl)-2-oxo-N-(3-oxo-3,4-dihydro-2H-benzo[1,4]oxazin-7-yl)-acetamide (45 70002186)

53a) N-(3-oxo-3,4-dihydro-2H-benzo[1,4]oxazin-7-yl)-oxalamic acid ethyl ester

The title compound is prepared from 7-amino-4H-benzo[1,4]oxazine-3-one [J. Med. Chem., 32, 1627. (1989)] and ethyl chlorooxoacetate (Aldrich) according to the method described in Example 1a. Melting Point: 239-240° C. (water)

53b) N-(3-oxo-3,4-dihydro-2H-benzo[1,4]oxazin-7-yl)-oxalamic acid

The title compound is prepared from N-(3-oxo-3,4-dihydro-2H-benzo[1,4]oxazin-7-yl)-oxalamic acid ethyl ester and potassium hydroxide according to the method described in Example 1b. Melting Point: 232.5-235.5° C. (water)

53c) 2-(4-Benzyloxy-piperidin-1-yl)-2-oxo-N-(3-oxo-3,4-dihydro-2H-benzo[1,4]oxazin-7-yl)-acetamide The title compound is prepared from N-(3-oxo-3,4-dihydro-2H-benzo[1,4]oxazin-7-yl)-oxalamic acid and 4-benzyloxy-piperidine [Tetrahedron Lett., 36 3465. (1995)] according to the method described in Example 1c. Melting Point: 143-146° C. (diethylether)

EXAMPLE 54

2-Oxo-N-(3-oxo-3,4-dihydro-2H-benzo[1,4]oxazin-7-yl)-2-(4-phenoxy-piperidin-1-yl)-acetamide (45 70002188)

The title compound is prepared from N-(3-oxo-3,4-dihydro-2H-benzo[1,4]oxazin-7-yl)-oxalamic acid (Example 53b) and 4-phenoxypiperidine according to the method described in Example 2. Melting Point: 196-199° C. (diethylether)

EXAMPLE 55

2-Oxo-N-(3-oxo-3,4-dihydro-2H-benzo[1,4]oxazin-7-yl)-2-(4-phenoxy-methyl-piperidin-1-yl)-acetamide (45 70002244)

The title compound is prepared from N-(3-oxo-3,4-dihydro-2H-benzo[1,4]oxazin-7-yl)-oxalamic acid (Example 53b) and 4-phenoxy-methyl-piperidine [DE 254 999 (1977)] according to the method described in Example 1c. Melting Point: 215-217° C. (diethylether)

EXAMPLE 56

2-Oxo-N-(3-oxo-3,4-dihydro-2H-benzo[1,4]oxazin-7-yl)-2-(4-phenethyl-piperidin-1-yl)-acetamide (45 70002250)

The title compound is prepared from N-(3-oxo-3,4-dihydro-2H-benzo[1,4]oxazin-7-yl)-oxalamic acid (Example 53b) and 4-phenethyl-piperidine [J. Amer. Chem. Soc., 72, 4953. (1950)] according to the method described in Example 1c. Melting Point: 128-132° C. (diethylether)

EXAMPLE 57

2-[4-(Hydroxy-phenyl-methyl)-piperidin-1-yl]-2-oxo-N-(3-oxo-3,4-dihydro-2H-benzo[1,4]oxazin-7-yl)-acetamide (45 70002251)

The title compound is prepared from N-(3-oxo-3,4-dihydro-2H-benzo[1,4]oxazin-7-yl)-oxalamic acid (Example 53b) and phenyl-piperidine-4-yl-methanol [J. Amer. Chem. Soc.,52, 4006. (1930)] according to the method described in Example 1c. Melting Point: 195-197° C. (diethylether)

EXAMPLE 58

2-Oxo-N-(3-oxo-3,4-dihydro-2H-benzo[1,4]oxazin-7-yl)-2-(4-p-tolyloxy-piperidin-1-yl)-acetamide (45 70002333)

The title compound is prepared from N-(3-oxo-3,4-dihydro-2H-benzo[1,4]oxazin-7-yl)-oxalamic acid (Example 53b) and 4-p-tolyloxy-piperidine according to the method described in Example 1c. Melting Point: 226-228° C. (diethylether)

EXAMPLE 59

2-[4-(4-Methylbenzyl)-piperidin-1-yl]-2-oxo-N-(3-oxo-3,4-dihydro-2H-benzo[1,4]oxazin-7-yl)-acetamide (45 70002339)

The title compound is prepared from N-(3-oxo-3,4-dihydro-2H-benzo[1,4]oxazin-7-yl)-oxalamic acid (Example 53b) and 4-(4-methylbenzyl)-piperidine [J Org. Chem., 64,3763. (1999)] according to the method described in Example 1c. Melting Point: 228-231° C. (diethylether)

EXAMPLE 60

2-(4-Benzyl-piperidin-1-yl)-N-(2-mercapto-3H-benzimidazol-5-yl)-2-oxo-acetamide (45 70002567)

60a) N-(2-Mercapto-3H-benzimidazol-5-yl)-oxalamic acid ethyl ester

The title compound is prepared from 6-amino-1H-benzimidazol-2-thiol [J. Chem. Soc., 1515 (1950)] and ethyl chlorooxoacetate (Aldrich) according to the method described in Example 1a Melting Point: 225-226° C. (water)

60b) N-(2-Mercapto-3H-benzimidazol-5-yl)-oxalamic acid

The title compound is prepared from N-(2-mercapto-3H-benzimidazole-5-yl)-oxalamic acid ethyl ester and potassium hydroxide according to the method described in Example 1b Melting Point: 276-280° C. (water)

60c) 2-(4-Benzyl-piperidin-1-yl)-N-(2-mercapto-3H-benzimidazol-5-yl)-2-oxo-acetamide The title compound is prepared from N-(2-mercapto-3H-benzimidazol-5-yl)-oxalamic acid and 4-benzyl-piperidine according to the method described in Example 1c. Melting Point: 277-281° C. (diethylether)

EXAMPLE 61

2-(4-Benzyl-piperidin-1-yl)-2-oxo-N-(2-oxo-2,3-dihydro-benzothiazol-6-yl)-acetamide (45 70002568)

61a) N-(2-Oxo-2,3-dihydro-benzothiazol-6-yl)-oxalamic acid ethyl ester

The title compound is prepared from 6-amino-3H-benzothiazol-2-one [Liebigs Ann. Chem., 277, 244 (1893)] and ethyl chlorooxoacetate (Aldrich) according to the method described in Example 1a Melting Point: 226-231° C. (water)

61b) N-(2-Oxo-2,3-dihydro-benzothiazol-6-yl)-oxalamic acid

The title compound is prepared from N-(2-oxo-2,3-dihydro-benzothiazol-6-yl)-oxalamic acid ethyl ester and potassium hydroxide according to the method described in Example 1b Melting Point: 275-278° C. (water)

61c) 2-(4-Benzyl-piperidin-1-yl)-2-oxo-N-(2-oxo-2,3-dihydro-benzothiazol-6-yl)-acetamide The title compound is prepared from N-(2-oxo-2,3-dihydro-benzothiazole-6-yl)-oxalamic acid and 4-benzylpiperidine according to the method described in Example 1c. Melting Point: 201-203° C. (diethylether)

EXAMPLE 62

2-[4-(4-Fluoro-benzyl)-piperidin-1-yl]-N-(2-mercapto-3H-benzimidazol-5-yl)-2-oxo-acetamide (45 70002569)

The title compound is prepared from N-(2-mercapto-3H-benzimidazol-5-yl)-oxalamic acid (Example 60b) and 4-(4-fluoro-benzyl)-piperidine according to the method described in Example 1c. Melting Point: 286-288° C. (diethylether)

EXAMPLE 63

2-[4-(4-Fluoro-benzyl)-piperidin-1-yl]-2-oxo-N-(2-oxo-2,3-dihydro-benzothiazol-6-yl)-acetamide (45 70002615)

The title compound is prepared from N-(2-oxo-2,3-dihydro-benzothiazol-6-yl)-oxalamic acid (Example 61b) and 4-(4-fluoro-benzyl)-piperidine according to the method described in Example 1c. Melting Point: 223.5-225.5° C. (diethylether)

EXAMPLE 64

2-Oxo-N-(2-oxo-2,3-dihydro-benzothiazol-6-yl)-2-(4-p-tolyloxy-piperidin-1-yl)-acetamide (45 70002706)

The title compound is prepared from N-(2-oxo-2,3-dihydro-benzothiazol-6-yl)-oxalamic acid (Example 61b) and 4-p-tolyloxy-piperidine according to the method described in Example 1c. Melting Point: 215-217° C. (diethylether)

EXAMPLE 65

2-[4-(4-Methyl-benzyl)-piperidin-1-yl]-2-oxo-N-(2-oxo-2,3-dihydro-benzothiazol-6-yl)-acetamide (45 80002247)

The title compound is prepared from N-(2-oxo-2,3-dihydro-benzothiazol-6-yl)-oxalamic acid (Example 61b) and 4-(4-methyl-benzyl)-piperidine according to the method described in Example 1c. Melting Point: 221-222° C. (diethylether)

EXAMPLE 66

2-[4-(4-Chloro-phenoxy)-piperidin-1-yl]-2-oxo-N-(2-oxo-2,3-dihydro-benzothiazol-6-yl)-acetamide (45 80002398)

The title compound is prepared from N-(2-oxo-2,3-dihydro-benzothiazol-6-yl)-oxalamic acid (Example 61b) and 4-(4-chloro-benzyl)-piperidine according to the method described in Example 1c. Melting Point: 245-247° C. (diethylether)

EXAMPLE 67

N-(2-Mercapto-3H-benzimidazol-5-yl)-2-(4-p-tolyloxy-piperidin-1-yl)-2-oxo-acetamide (45 70002739)

The title compound is prepared from N-(2-mercapto-3H-benzimidazol-5-yl)-oxalamic acid (Example 60b) and 4-p-tolyloxy-piperidine according to the method described in Example 1c. Melting Point: 311-314° C. (diethylether)

EXAMPLE 68

2-(4-Benzyl-piperidin-1-yl)-2-oxo-N-(3-thioxo-3,4-dihydro-2H-benzo[1,4]oxazin-7-yl)-acetamide (45 70002614)

68a) 7-amino-4H-benzo[1,4]oxazin-3-thione
A stirred mixture of 1.0 g of 7-nitro-4H-benzo[1,4]oxazin-3-thione [Indian J. Chem. Sect. B, 12, 1279. (1984)] and 4.0 g of sodium dithionite in 30 ml of ethanol and 30 ml of water is refluxed for 2 hours. Then the reaction mixture is concentrated and the residue is submitted to column chromatography using Kieselgel 60 as adsorbent (Merck) and chloroform:methanol=9:1 as eluent to yield 0.33 g (38%) of the title compound. Melting Point: 205-211° C. (diethylether)
68b) 2-(4-Benzyl-piperidin-1-yl)-2-oxo-N-(3-thioxo-3,4-dihydro-2H-benzo[1,4]oxazin-7-yl)-acetamide
The title compound is prepared from 7-amino-4H-benzo[1,4]oxazin-3-thione and (4-benzyl-piperidin-1-yl)-oxoacetic acid (Example 5b) according to the method described in Example 1c. Melting Point: 193-196° C. (diethylether)

EXAMPLE 69

({3-[2-(4-Benzyl-piperidin-1-yl)-2-oxo-acetylamino]-phenylcarbamoyl}-methyl)-carbamic acid tert-butyl ester (45 70001965

The title compound is prepared from N-(3-aminophenyl)-2-(4-benzyl-piperidin-1-yl)-2-oxo-acetamide (Example 11) and N-(tert-butoxycarbonyl)glycine (Aldrich) according to the method described in Example 1c. Melting Point: 81-85° C. (diethylether)

EXAMPLE 70

2-(4-Benzyl-piperidin-1-yl)-N-(4-nitrophenyl)-2-oxo-acetamide (45 70001966

The title compound is prepared from (4-benzyl-piperidin-1-yl)-oxo-acetic acid (Example 5b) and 4-nitroaniline (Aldrich) according to the method described in Example 1c. Melting Point: 162-165° C. (diethylether)

EXAMPLE 71

2-(4-Benzyl-piperidin-1-yl)-2-oxo-N-[3-(1H-tetrazol-5-yl)-phenyl]-acetamide (45 7001984)

71a) 2-(4-Benzyl-piperidin-1-yl)-N-(3-cyanophenyl)-2-oxo-acetamide
The title compound is prepared from (4-benzyl-piperidin-1-yl)-oxo-acetic acid (Example 5b) and 3-aminobenzonitrile (Aldrich) according to the method described in Example 1c. Melting Point: oil.
71b) 2-(4-Benzyl-piperidin-1-yl)-2-oxo-N-[3-(1H-tetrazol-5-yl)-phenyl]-acetamide
A mixture of 0.7 g (2 mmol) of 2-(4-benzyl-piperidin-1-yl)-N-(3-cyanophenyl)-2-oxo-acetamide, 0.82 g (4 mmol) of azidotrimethyltin (Aldrich) and 20 ml of toluene is refluxed for 20 hours. The precipitated crystals are filtered off and treated with 20 ml of N hydrochloric acid to yield 0.42 g (54%) of the title compound. Melting Point: 159-161° C. (water)

EXAMPLE 72

2-[4-(4-Fluoro-benzyl-piperidin-1-yl)-2-oxo-N-[4-(1H-tetrazol-5-yl)-phenyl]-acetamide (45 7001986)

The title compound is prepared from N-(4-cyanophenyl)-2-[4-(4-fluoro-benzyl)-piperidin-1-yl]-2-oxoacetamide (Example 9) and azidomethyltin (Aldrich) according to the method described in Example 71b. Melting Point: 123-125° C. (water)

EXAMPLE 73

N-(4-Amino-phenyl)-2-(4-benzyl-piperidin-1-yl)-2-oxo-acetamide hydrochloride (45 7000 1987)

The title compound is prepared from 2-(4-benzyl-piperidin-1-yl)-N-(4-nitrophenyl)-2-oxo-acetamide (Example 70) according to the method described in Example 11. The residue is treated with 2.5 N hydrochloric acid in ethyl acetate to yield the title compound. Melting Point: >260° C. (ethyl acetate)

EXAMPLE 74

2-(4-Benzyl-piperidin-1-yl)-2-oxo-N-[4-(1H-tetrazol-5-yl)-phenyl]-acetamide (45 7002020)

The title compound is prepared from N-(4-cyanophenyl)-2-(4-benzyl-piperidin-1-yl]-2-oxo-acetamide (Example 5c) and azidomethyltin (Aldrich) according to the method described in Example 86b. Melting Point: 127-129° C. (water)

EXAMPLE 75

N-[3-(2-Amino-acetylamino)-phenyl]-2-(4-benzyl-piperidin-1-yl)-2-oxo-acetamide hydrochloride (45 70002053)

A mixture of 0.5 g (1 mmol) of ({3-[2-(4-benzyl-piperidin-1-yl)-2-oxo-acetyl-amino]-phenylcarbamoyl}-methyl)-carbamic acid tert-butyl ester (Example 69) and 20 ml of 2.5 N hydrochloric acid in ethyl acetate is stirred at room temperature for 1 hour. The precipitated product is filtered off and washed with ethyl acetate to yield 0.41 g (95.1%) of the title compound. Melting Point: 85-90° C. (ethyl acetate)

EXAMPLE 76

2-(4-Benzyl-piperidin-1-yl)-N-(2-hydroxyphenyl)-2-oxo-acetamide (45 70002058)

The title compound is prepared from (4-benzyl-piperidin-1-yl)-oxo-acetic acid (Example 5b) and 2-aminophenol (Aldrich) according to the method described in Example 1c. Melting Point: 121-125-165° C. (hexane)

EXAMPLE 77

[(3-{2-[4-(4-Fluoro-benzyl-piperidin-1-yl)-2-oxo-acetylamino}-phenylcarbamoyl)-methyl]-carbamic acid tert-butyl ester (45 70002082)

The title compound is prepared from N-(3-aminophenyl)-2-[4-fluoro-(4-benzyl)-piperidin-1-yl)-2-oxo-acetamide (Example 16) and N-(tert-butoxycarbonyl)-glycine (Aldrich) according to the method described in Example 2. Melting Point: 79-83° C. (diisopropyl ether)

EXAMPLE 78

N-[3-(2-Amino-acetylamino)-phenyl]-2-[4-(4-fluoro-benzyl-piperidin-1-yl)-2-oxo-acetamide hydrochloride (45 70002118)

The title compound is prepared from [(3-{2-[4-(4-fluoro-benzyl-piperidin-1-yl)-2-oxo-acetylamino}-phenylcarbamoyl)-methyl)-carbamic acid tert-butyl ester (Example 77) according to the method described in Example 75. Melting Point: 120-125° C. (ethyl acetate)

EXAMPLE 79

2-[4-(4-Fluoro-benzyl)-piperidin-1-yl]-2-oxo-N-[3-(1H-tetrazol-5-yl)-phenyl]-acetamide (45 7002119)

The title compound is prepared from N-(3-cyano-phenyl)-2-[4-(4-fluoro-benzyl)-piperidin-1-yl]-2-oxo-acetamide (Example 14) and azidomethyltin (Aldrich) according to the method described in Example 71. Melting Point: 107-112° C. (water)

EXAMPLE 80

N-(2-Cyano-phenyl)-2-[4-(4-fluoro-benzyl)-piperidin-1-yl]-2-oxo-acetamide (45 70002120)

The title compound is prepared from [4-(4-fluoro-benzyl)-piperidin-1-yl]-oxo-acetic acid (Example 1b) and 2-aminobenzonitrile (Aldrich) according to the method described in Example 1c. Melting Point: 101-103° C. (diethylether)

EXAMPLE 81

2-[4-(4-Fluoro-benzyl)-piperidin-1-yl]-N-(indan-5-yl)-2-oxo-acetamide (45 70002198)

The title compound is prepared from [4-(4-fluoro-benzyl)-piperidin-1-yl]-oxo-acetic acid (Example 1b) and 5-aminoindan (Aldrich) according to the method described in Example 1c. Melting Point: 150-152° C. (diethylether)

EXAMPLE 82

N-(3-Benzylamino-phenyl)-2-(4-benzyl-piperidin-1-yl)-2-oxo-acetamide hydrochloride (45 70002201)

To a stirred solution of 0.51 g (1.5 mmol) of N-(3-aminophenyl)-2-(4-benzyl-piperidin-1-yl)-2-oxo-acetamide (Example 11), 0.15 ml (1.5 mmol) of benzaldehyde, 0.18 ml (3 mmol) of acetic acid in 15 ml of dichloroethane 0.48 g (2.25 mmol) of sodium triacetoxyborohydride (Aldrich) is added in small portions below 20° C., and the reaction mixture is stirred at room temperature for 2 hours. Then 30 ml of 8% sodium hydrogencarbonate solution is added to the mixture, the organic layer is separated and the water phase is extracted three times with 30 ml of chloroform. The combined organic layers are dried over sodium sulfate, concentrated and the residue is purified by column chromatography using Kieselgel 60 as adsorbent (Merck) and ethyl acetate:hexane=1:2 as eluent. The product is treated with 2.5 N hydrochloric acid in ethyl acetate solution to yield 0.25 g (36%) of the title compound. Melting Point: 190-207° C. (dec.) (ethyl acetate)

EXAMPLE 83

2-(4-Benzyl-piperidin-1-yl)-N-(indan-5-yl)-2-oxo-acetamide (45 70002224)

The title compound is prepared from (4-benzyl-piperidin-1-yl)-oxo-acetic acid (Example 5b) and 5-aminoindan (Aldrich) according to the method described in Example 1c. Melting Point: 106-109° C. (diethylether)

EXAMPLE 84

2-[4-(4-Fluoro-benzyl)-piperidin-1-yl]-N-(4-hydroxy-phenyl)-2-oxo-acetamide (45 70002225)

The title compound is prepared from [4-(4-fluoro-benzyl)-piperidin-1-yl]-oxo-acetic acid (Example 1b) and 4-aminophenol (Aldrich) according to the method described in Example 1c. Melting Point: 98-100° C. (diethylether)

EXAMPLE 85

2-[4-(4-Fluoro-benzyl)-piperidin-1-yl]-N-(3-hydroxy-phenyl)-2-oxo-acetamide (45 70002226)

The title compound is prepared from [4-(4-fluoro-benzyl)-piperidin-1-yl]-oxo-acetic acid (Example 1b) and 3-aminophenol (Aldrich) according to the method described in Example 1c. Melting Point: 175-179° C. (diethylether)

EXAMPLE 86

2-(4-Benzyl-piperidin-1-yl)-N-(4-bromo-phenyl)-2-oxo-acetamide (45 70002238)

The title compound is prepared from (4-benzyl-piperidin-1-yl)-oxo-acetic acid (Example 5b) and 4-bromo-aniline (Aldrich) according to the method described in Example 1c. Melting Point: 131-132° C. (diethylether)

EXAMPLE 87

2-[4-(4-Fluoro-benzyl)-piperidin-1-yl]-N-(1H-indol-5-yl)-2-oxo-acetamide (45 70002239)

The title compound is prepared from [4-(4-fluoro-benzyl)-piperidin-1-yl]-oxo-acetic acid (Example 1b) and 5-amino-indole (Aldrich) according to the method described in Example 1c. Melting Point: 80-82° C. (ethyl acetate)

EXAMPLE 88

2-[4-(4-Fluoro-benzyl)-piperidin-1-yl]-2-oxo-N-[2-(1H-tetrazol-5-yl)-phenyl]-acetamide (45 70002240)

The title compound is prepared from N-(4-cyano-phenyl)-2-[4-(4-fluoro-benzyl)-piperidin-1-yl]-2-oxo-acetamide (Example 9) and azidomethyltin (Aldrich) according to the method described in Example 71b. Melting Point: 107-109° C. (water)

EXAMPLE 89

2-(4-Benzyl-piperidin-1-yl)-2-oxo-N-phenyl-acetamide (45 70002241)

The title compound is prepared from (4-benzyl-piperidin-1-yl)-oxo-acetic acid (Example 5b) and aniline (Aldrich) according to the method described in Example 1c. Melting Point: 125-128° C. (diethylether)

EXAMPLE 90

2-(4-Benzyl-piperidin-1-yl)-N-(4-methyl-phenyl)-2-oxo-acetamide (45 70002263)

The title compound is prepared from (4-benzyl-piperidin-1-yl)-oxo-acetic acid (Example 5b) and 4-methyl-aniline (Aldrich) according to the method described in Example 1c. Melting Point: 115-117° C. (diethylether)

EXAMPLE 91

N-(3-Benzylamino-phenyl)-2-[4-(4-fluoro-benzyl)-piperidin-1-yl]-2-oxo-acetamide hydrochloride (45 70002265)

To a stirred solution of 0.53 g (1.5 mmol) of N-(3-aminophenyl)-2-[4-(4-fluoro-benzyl)-piperidin-1-yl]-oxo-acetamide (Example 16), 0.15 ml (1.5 mmol) of benzaldehyde, 0.18 ml (3 mmol) of acetic acid in 15 ml of dichloroethane 0.48 g (2.25 mmol) of sodium triacetoxyborohydride is added in small portions below 20° C., and the reaction mixture is stirred at room temperature for 2 hours. Then 30 ml of 8% sodium hydrogencarbonate solution is added to the mixture, the organic layer is separated and the water phase is extracted three times with 30 ml of chloroform. The combined organic layers are dried over sodium sulfate, concentrated and the residue is treated with 2.5 N hydrochloric acid in ethylacetate to yield 0.39 g (54%) of the title compound. Melting Point: 206-213° C. (dec.) (ethyl acetate)

EXAMPLE 92

2-(4-Benzyl-piperidin-1-yl)-N-(4-methoxy-phenyl)-2-oxo-acetamide (45 70002305)

The title compound is prepared from (4-benzyl-piperidin-1-yl)-oxo-acetic acid (Example 5b) and 4-methoxyaniline (Aldrich) according to the method described in Example 1c. Melting Point: 144-146° C. (diethylether)

EXAMPLE 93

2-[4-(4-Fluoro-benzyl)-piperidin-1-yl]-N-(4-nitro-phenyl)-2-oxo-acetamide (45 70002306)

The title compound is prepared from [4-(4-fluoro-benzyl)-piperidine-1-yl]-oxo-acetic acid (Example 1b) and 4-nitro-aniline (Aldrich) according to the method described in Example 1c. Melting Point: 157-159° C. (diethylether)

EXAMPLE 94

N-(4-Bromo-phenyl)-2-[4-(4-fluoro-benzyl)-piperidin-1-yl]-2-oxo-acetamide (45 70002307)

A mixture of 0.64 g (2.4 mmol) of [4-(4-fluoro-benzyl)piperidin-1-yl]-oxo-acetic acid, 0.34 ml (2.4 mmol) of triethylamine, 0.35 g (2 mmol) of 4-bromo-aniline (Aldrich), 0.91 g (2.4 mmol) of HBTU and 10 ml of dimethylformamide is stirred at room temperature for 24 hours. The reaction mixture is concentrated. Then 30 ml of 8% sodium hydrogencarbonate solution and 30 ml of chloroform is added to the mixture. The organic layer is separated and the water phase is extracted three times with 20 ml of chloroform. The combined organic layers are dried over sodium sulfate, concentrated. The residue is treated with diethylether and the crystals are filtered off to yield 0.36 g (43%) of the title compound. Melting Point: 156-158° C. (diethylether)

EXAMPLE 95

2-[4-(4-Fluoro-benzyl)-piperidin-1-yl]-2-oxo-N-(3-trifluoromethyl-phenyl)-acetamide (45 70002308)

The title compound is prepared from [4-(4-fluoro-benzyl)-piperidine-1-yl]-oxo-acetic acid (Example 1b) and 3-(trifluoromethyl)-aniline (Aldrich) according to the method described in Example 94. Melting Point: 113-115° C. (diethylether

EXAMPLE 96

2-[4-(4-Fluoro-benzyl)-piperidin-1-yl]-N-(4-methyl-phenyl)-2-oxo-acetamide (45 70002341)

The title compound is prepared from [4-(4-fluoro-benzyl)-piperidin-1-yl]-oxo-acetic acid (Example 1b) and 4-methyl-aniline (Aldrich) according to the method described in Example 94. Melting Point: 125-126° C. (diethylether

EXAMPLE 97

2-[4-(4-Fluoro-benzyl)-piperidin-1-yl]-N-(4-methoxy-phenyl)-2-oxo-acetamide (45 70002342)

The title compound is prepared from [4-(4-fluoro-benzyl)-piperidin-1-yl]-oxo-acetic acid (Example 1b) and 4-methoxy-aniline (Aldrich) according to the method described in Example 94. Melting Point: 105-107° C. (diethylether

EXAMPLE 98

2-(4-Benzyl-piperidin-1-yl)-2-oxo-N-(3-trifluoromethyl-phenyl)-acetamide (45 70002343)

The title compound is prepared from (4-benzyl-piperidin-1-yl)-oxoacetic acid (Example 5b) and 3-(trifluoromethyl)-aniline (Aldrich) according to the method described in Example 1c. Melting Point: 87-89° C. (hexane)

EXAMPLE 99

N-(4-Benzylamino-phenyl)-2-(4-benzyl-piperidin-1-yl)-2-oxo-acetamide (45 70002344)

The title compound is prepared from N-(4-amino-phenyl)-2-(4-benzyl-piperidin-1-yl)-2-oxo-acetamide hydrochloride (Example 73) and benzaldehyde (Aldrich) according to the method described in Example 91. Melting Point: 126-128° C. (diethylether)

EXAMPLE 100

{4-[2-(4-Benzyl-piperidin-1-yl)-2-oxo-acetylamino]-phenyl}-carbamic acid tert-butyl ester (45 70002345)

The title compound is prepared from N-(4-amino-phenyl)-2-(4-benzyl-piperidin-1-yl)-2-oxo-acetamide hydrochloride (Example 73) and N-(tert-butoxycarbonyl)-glycine (Aldrich) according to the method described in Example 94. Melting Point: 177-179° C. (diisopropylether)

EXAMPLE 101

2-[4-[4-Methyl-benzyl)-piperidin-1-yl]-2-oxo-N-(2-oxo-2,3-dihydro-1H-indol-5-yl)-acetamide (45 70002346)

101a) N-(2-Oxo-2,3-dihydro-1H-indol-5-yl)-oxalamic acid ethyl ester

The title compound is prepared from 1-amino-1,3-dihydro-indol-2-one and ethyl oxalyl chloride according to the method described in Example 1a. Melting Point: 235-237° C. (diethylether)

101b) N-(2-Oxo-2,3-dihydro-1H-indol-5-yl)-oxalamic acid

The title compound is prepared from N-(2-oxo-2,3-dihydro-1H-indol-5-yl)-oxalamic acid_ethyl ester and potassium hydroxide according to the method described in Example 1b. Melting Point: 256° C. (water)

101c) 2-[4-[4-Methyl-benzyl)-piperidin-1-yl]-2-oxo-N-(2-oxo-2,3-dihydro-1H-indol-5yl)-acetamide The title compound is prepared from N-(2-oxo-2,3-dihydro-1H-indol-5-yl)-oxalamic acid_and 4-(4-methyl-benzyl)-piperidine according to the method described in Example 1c. Melting Point: 196-199° C. (diethylether)

EXAMPLE 102

2-(4-Benzyl-piperidin-1-yl)-N-(1H-indol-5-yl)-2-oxo-acetamide (45 70002347)

The title compound is prepared from 5-aminoindole (Aldrich) and (4-benzyl-piperidin-1-yl)-oxo-acetic acid (Example 5b) according to the method described in Example 1c. Melting Point: 68-72° C. (hexane)

EXAMPLE 103

2-[(4-Hydroxy-phenyl-methyl)-piperidin-1-yl]-N-(2-oxo-2,3-dihydro-1H-indol-5-yl)-2-oxo-acetamide 45 70002348

The title compound is prepared from N-(2-oxo-2,3-dihydro-1H-indol-5-yl)-oxalamic acid_(Example 101b) and phenyl-[4]piperidyl-methanol according to the method described in Example 1c. Melting Point: 88-100° C. (dec.) (diethylether)

EXAMPLE 104

N-(4-Amino-phenyl)-2-[4-(4-fluoro-benzyl)-piperidin-1-yl]-2-oxo-acetamide (45 70002349)

The title compound is prepared from 2-[4-(4-fluoro-benzyl)-piperidin-1-yl]-N-(4-nitro-phenyl)-2-oxo-acetamide (Example 93) according to the method described in Example 11. Melting Point: 141-143° C. (diisopropylether-hexane).

EXAMPLE 105

2-[4-[2-Methyl-benzyl)-piperidin-1-yl]-2-oxo-N-(2-oxo-2,3-dihydro-1H-indol-5-yl)-acetamide (45 70002350)

The title compound is prepared from N-(2-oxo-2,3-dihydro-1H-indol-5-yl)-oxalamic acid (Example 101b) and 4-(2-methyl-benzyl)-piperidine [J. Org. Chem., 64, 3763. (1999)] according to the method described in Example 1c. Melting Point: 211-213° C. (diethylether)

EXAMPLE 106

2-Oxo-N-(2-oxo-2,3-dihydro-1H-indol-5-yl)-2-(4-phenoxymethyl-piperidin-1-yl)-acetamide (45 70002351)

The title compound is prepared from N-(2-oxo-2,3-dihydro-1H-indol-5-yl)-oxalamic acid (Example 101b) and 4-phenoxy-methyl-piperidine according to the method described in Example 1c. Melting Point: 200-202° C. (diethylether)

EXAMPLE 107

2-[4-[4-Methoxy-benzyl)-piperidin-1-yl]-2-oxo-N-(2-oxo-2,3-dihydro-1H-indol-5-yl)-acetamide (45 70002391)

The title compound is prepared from N-(2-oxo-2,3-dihydro-1H-indol-5-yl)-oxalamic acid (Example 101b) and 4-(4-methoxy-benzyl)-piperidine [U.S. Pat. No. 3,632,767 (1972)] according to the method described in Example 1c. Melting Point: 215-217° C. (diethylether)

EXAMPLE 108

N-[4-(2-Amino-acetylamino)-phenyl]-2-(4-benzyl-piperidin-1-yl)-2-oxo-acetamide hydrochloride (45 70002392)

The title compound is prepared from {4-[2-(4-benzyl-piperidin-1-yl)-2-oxo-acetylamino]-phenyl}-carbamic acid tert-butyl ester (Example 100) according to the method described in Example 75. Melting Point: 227-233 (dec.)° C. (diethylether)

EXAMPLE 109

2-[4-(4-Fluoro-benzyl)-piperidin-1-yl]-N-(4-methanesulfonylamino-phenyl)-2-oxo-acetamide (45 70002393)

The title compound is prepared from N-(4-amino-phenyl)-2-[4-(4-fluoro-benzyl)-piperidin-1-yl]-2-oxo-acetamide (Example 104) according to the method described in Example 12. Melting Point: 178-182° C. (diethylether)

EXAMPLE 110

N-(4-Benzylamino-phenyl)-2-[4-(4-fluoro-benzyl)-piperidin-1-yl]-2-oxo-acetamide (45 70002394)

The title compound is prepared from N-(4-amino-phenyl)-2-[4-(4-fluoro-benzyl)-piperidin-1-yl]-2-oxo-acetamide (Example 104) and benzaldehyde according to the method described in Example 82. Melting Point: 145-148° C. (diethylether)

EXAMPLE 111

2-[4-(3-Fluoro-benzyl)-piperidin-1-yl]-2-oxo-N-(2-oxo-2,3-dihydro-1H-indol-5-yl)-acetamide (45 70002439)

The title compound is prepared from N-(2-oxo-2,3-dihydro-1H-indol-5-yl)-oxalamic acid (Example 101b) and 4-(3-fluoro-benzyl)-piperidine [J. Org. Chem. 64, 3763. (1999)] according to the method described in Example 1c. Melting Point: 182-184° C. (diethylether)

EXAMPLE 112

2-Oxo-N-(2-oxo-2,3-dihydro-1H-indol-5-yl)-2-(4-phenethyl-piperidin-1-yl)-acetamide (45 70002440)

The title compound is prepared from N-(2-oxo-2,3-dihydro-1H-indol-5-yl)-oxalamic acid (Example 101b) and 4-phenethyl-piperidine according to the method described in Example 1c. Melting Point: 236-240° C. (diethylether)

EXAMPLE 113

2-(4-Benzyl-piperidin-1-yl)-N-(3-hydroxy-methyl-phenyl)-2-oxo-acetamide (45 70002541)

The title compound is prepared from (4-benzyl-piperidin-1-yl)-oxo-acetic acid (Example 5b) and 3-amino-benzyl alcohol [Tetrahedron Lett. 41, 175. (2000)] according to the method described in Example 1c. Melting Point: 143-146° C. (diisopropylether)

EXAMPLE 114

2-[4-(4-Fluoro-benzyl)-piperidin-1-yl]-N-(3-hydroxy-methyl-phenyl))-2-oxo-acetamide (45 70002542)

The title compound is prepared from [4-(4-fluoro-benzyl)-piperidin-1-yl]-oxo-acetic acid (Example 1b) and 3-amino-benzyl alcohol according to the method described in Example 1c. Melting Point: 105-107° C. (diisopropylether)

EXAMPLE 115

N-3-(Chloro-methyl-phenyl)-2-[4-(4-fluoro-benzyl)-piperidin-1-yl]-2-oxo-acetamide (45 70002607)

To a stirred solution of 0.31 g (0.81 mmol) of 2-[4-(4-fluoro-benzyl)-piperidin-1-yl]-N-(3-hydroxy-methyl-phenyl))-2-oxo-acetamide (Example 114) and 1 ml (12 mmol) of pyridine in 10 ml of toluene 0.9 ml (12 mmol) of thionyl chloride in 5 ml of toluene is added dropwise below 10° C., and the reaction mixture is stirred at room temperature for 4 hours. The reaction mixture is concentrated. Then 50 ml of 8% sodium hydrogenecarbonate solution and 20 ml of ethyl acetate is added to the mixture. The organic layer is separated and the water phase is extracted three times with 10 ml of ethyl acetate. The combined organic layers are dried over sodium sulfate, concentrated and the residue is purified by column chromatography using Kieselgel 60 as adsorbent (Merck) and hexane:ethyl acetate=2:1 as eluent to yield 0.05 g (16%) of the title compound. Melting Point: 104-110° C. (diethylether

EXAMPLE 116

2-(4-Benzyl-piperidin-1-yl)-N-3-(chloro-methyl-phenyl)-2-oxo-acetamide (45 70002606)

The title compound is prepared from 2-(4-benzyl-piperidin-1-yl)-N-(3-hydroxy-methyl-phenyl))-2-oxo-acetamide (Example 113) and thionyl chloride according to the method described in Example 115. Melting Point: 92-95° C. (diisopropylether)

EXAMPLE 117

2-(4-Benzyl-piperidin-1-yl)-N-(4-hydroxy-methyl-phenyl))-2-oxo-acetamide (45 70002629)

The title compound is prepared from (4-benzyl-piperidine-1-yl)-oxo-acetic acid (Example 5b) and 4-amino-benzyl alcohol (Fluka) according to the method described in Example 1c. Melting Point: 72-74° C. (hexane)

EXAMPLE 118

2-[4-(4-Fluoro-benzyl)-piperidin-1-yl]-N-(4-hydroxy-methyl-phenyl))-2-oxo-acetamide (45 70002640)

The title compound is prepared from [4-(4-fluoro-benzyl)-piperidin-1-yl]-oxo-acetic acid (Example 1b) and 4-amino-benzyl alcohol (Fluka) according to the method described in Example 2. Melting Point: 80-85° C. (water)

EXAMPLE 119

2-[4-(4-Methyl-benzyl)-piperidin-1-yl]-2-oxo-N-(2-oxo-2,3-dihydro-benzoxazol-6-yl]-acetamide (45 70002764)

119a) [4-(4-Methyl-benzyl)-piperidin-1-yl]-oxo-acetic acid ethyl ester

The title compound is prepared from 4-(4-methyl-benzyl)-piperidin and ethyl oxalyl chloride according to the method described in Example 1a. Melting Point: oil 119b) [4-(4-Methyl-benzyl)-piperidin-1-yl]-oxo-acetic acid The title compound is prepared from [4-(4-methyl-benzyl-piperidin-1-yl)-oxo-acetic acid ethyl ester according to the method described in Example 1b. Melting Point: 133-135° C. (ethanol-water)

119c) 2-[4-(4-methyl-benzyl)-piperidin-1-yl]-2-oxo-N-(2-oxo-2,3-dihydro-benzoxazol-6-acetamide The title compound is prepared from 5-amino-1,3-dihydro-indol-2-one and [4-(4-methyl-benzyl)-piperidin-1-yl)-oxo-acetic acid according to the method described in Example 1c. Melting Point: 216-220° C. (diethylether)

EXAMPLE 120

2-(4-Benzyl-piperidin-1-yl)-N-(4-chloro-methyl-phenyl)-2-oxo-acetamide (45 70002765)

The title compound is prepared from 2-(4-benzyl-piperidin-1-yl)-N-(4-hydroxy-methyl-phenyl)-2-oxo-acetamide (Example 117) and thionyl chloride according to the method described in Example 115. Melting Point: 105-108° C. (diethylether)

EXAMPLE 121

N-(4-Methanesulfonylamino-phenyl)-2-[4-(4-methyl-benzyl)-piperidin-1-yl]-2-oxo-acetamide (45 70002769)

The title compound is prepared from methanesulfonic acid-(4-amino-anilide) and [4-(4-methyl-benzyl)-piperidin-1-yl)-oxo-acetic acid (Example 119b) according to the method described in Example 94. Melting Point: 179-181° C. (diethylether)

EXAMPLE 122

2-[4-[4-Methoxy-benzyl)-piperidin-1-yl]-2-oxo-N-(2-oxo-2,3-dihydro-benzoxazol-6-yl)-acetamide (45 70002777)

The title compound is prepared from N-(2-oxo-2,3-dihydro-benzoxazol-6-yl)-oxalamic acid (Example 43e) and 4-(4-methoxy-benzyl)-piperidine according to the method described in Example 1c. Melting Point: 193-197° C. (diisopropylether)

EXAMPLE 123

N-(4-Methanesulfonylamino-phenyl)-2-[4-[4-methoxy-benzyl)-piperidin-1-yl]-2-oxo-acetamide (45 70002778)

123a) N-(4-Methanesulfonylamino-phenyl)-oxalamic acid ethyl ester

The title compound is prepared from methanesulfonic acid-(4-amino-anilide) according to the method described in Example 1a. Melting Point: 136-139° C. (diisopropylether)

123b) N-(4-Methanesulfonylamino-phenyl)-oxalamic acid

The title compound is prepared from N-(4-methanesulfonylamino-phenyl)-oxalamic acid ethyl ester according to the method described in Example 1b. Melting Point: >260° C. (ethanol-water)

123c) N-(4-Methanesulfonylamino-phenyl)-2-[4-[4-methoxy-benzyl)-piperidin-1-yl]-2-oxo-acetamide The title compound is prepared from N-(4-methanesulfonylamino-phenyl)-oxalamic acid and 4-(4-methoxy-benzyl)-piperidine according to the method described in Example 1c. Melting Point: 206-208° C. (diethylether)

EXAMPLE 124

2-(4-Benzyl-piperidin-1-yl)-N-(2-methanesulfonylamino-phenyl)-[-2-oxo-acetamide (45 70002780)

The title compound is prepared from N-(2-amino-phenyl)-methanesulfonamide [Aust.J. Chem.25, (1972) 1341] and (4-benzyl-piperidin-1-yl)-oxo-acetic-acid (Example 5b) according to the method described in Example 1c. Melting Point: 154-156° C. (diethylether)

EXAMPLE 125

2-[4-(4-Fluoro-benzyl)-piperidin-1-yl]-N-(2-methanesulfonylamino-phenyl)]-2-oxo-acetamide (45 70002781)

The title compound is prepared from N-(2-amino-phenyl)-methanesulfonamide and [4-(4-fluoro-benzyl)-piperidin-1-yl]-oxo-acetic-acid (Example 1b) according to the method described in Example 1c. Melting Point: 166-168° C. (diethylether)

EXAMPLE 126

2-[4-(4-Fluoro-benzyl)-piperidin-1-yl]-2-oxo-N-(4-trifluoromethyl-phenyl)-acetamide (45 70002793)

The title compound is prepared from 4-(trifluoromethyl)-aniline and [4-(4-fluoro-benzyl)-piperidin-1-yl]-oxo-acetic-acid (Example 1b) according to the method described in Example 1c. Melting Point: 109-111° C. (diisopropylether)

EXAMPLE 127

2-[4-[3-Methoxy-benzyl)-piperidin-1-yl]-2-oxo-N-(2-oxo-2,3-dihydro-benzoxazol-6-yl)-acetamide (45 70002838)

The title compound is prepared from N-(2-oxo-2,3-dihydro-benzoxazol-6-yl)-oxalamic acid (Example 43e) and 4-(3-methoxy-benzyl)-piperidine [U.S. Pat. No. 3,632,767 (1972)] according to the method described in Example 2. Melting Point: 110-115° C. (diisopropylether)

EXAMPLE 128

2-[4-[3-Methyl-benzyl)-piperidin-1-yl]-2-oxo-N-(2-oxo-2,3-dihydro-benzoxazol-6-yl)-acetamide (45 70002839)

The title compound is prepared from N-(2-oxo-2,3-dihydro-benzoxazol-6-yl)-oxalamic acid (Example 43e) and 4-(3-methyl-benzyl)-piperidine according to the method described in Example 2. Melting Point: 204-208° C. (diisopropylether)

EXAMPLE 129

N-(1,3-Dioxo-2,3-dihydro-1H-isoindol-5-yl)-2-[4-(4-fluoro-benzyl)-piperidin-1-yl]-2-oxo-acetamide (45 70002840)

The title compound is prepared from 5-amino-isoindole-1,3-dione [Tetrahedron 54, 7485. (1998)] and [4-(4-fluoro-benzyl)-piperidin-1-yl]-oxo-acetic-acid (Example 1b) according to the method described in Example 1c. Melting Point: 226-228° C. (diethylether)

EXAMPLE 130

2-(4-Benzyl-piperidin-1-yl)-N-(1,3-dioxo-2,3-dihydro-1H-isoindol-5-yl)-2-oxo-acetamide (45 70002841)

The title compound is prepared from 5-amino-isoindole-1,3-dione and (4-benzyl-piperidin-1-yl)-oxo-acetic-acid (Example 5b) according to the method described in Example 1c. Melting Point: 239-241° C. (diethylether)

EXAMPLE 131

2-[4-[3-Fluoro-benzyl)-piperidin-1-yl[-2-oxo-N-(2-oxo-2,3-dihydro-benzoxazol-6-yl)-acetamide (45 70002897)

The title compound is prepared from N-(2-oxo-2,3-dihydro-benzoxazol-6-yl)-oxalamic acid (Example 43e) and 4-(3-fluoro-benzyl)-piperidine according to the method described in Example 1c. Melting Point: 215-217° C. (diethylether)

EXAMPLE 132

2-[4-(4-Fluoro-benzyl)-piperidin-1-yl]-2-oxo-N-(4-sulfamoyl-phenyl)-acetamide (45 70002957)

The title compound is prepared from sulfanilamide (Aldrich) and [4-(4-fluoro-benzyl)-piperidin-1-yl]oxo-acetic-acid (Example 1b) according to the method described in Example 1c. Melting Point: 201-203° C. (diethylether)

EXAMPLE 133

2-(4-Benzyl-piperidin-1-yl)-2-oxo-N-(4-sulfamoyl-phenyl)acetamide (45 70002958)

The title compound is prepared from sulfanilamide (Aldrich) and (4-benzyl-piperidin-1-yl)-oxo-acetic-acid (Example 5b) according to the method described in Example 1c. Melting Point: 184-187° C. (diethylether)

EXAMPLE 134

Acetic-acid-4-[(2-(4-benzyl-piperidin-1-yl)-2-oxo-acetylamino]-phenyl ester (45 70003020)

To a stirred solution of 0.68 g (2 mmol) of 2-(4-benzyl-piperidin-1-yl)-N-(4-hydroxy-phenyl)-2-oxo-acetamide (Example 18) and 0.42 ml (3 mmol) of triethylamine in 20 ml of chloroform 0.2 ml (3 mmol) of acetyl chloride in 5 ml of chloroform is added dropwise below 10° C., and the reaction mixture is stirred at room temperature for 3 hours. The solvent is evaporated and the residue is treated with water and the crystals are filtered off to yield 0.7 g (92%) of the title compound. Melting Point: 149-151° C. (water)

EXAMPLE 135

Methanesulfonic acid 4-[(2-(4-benzyl-piperidin-1-yl)-2-oxo-acetylamino]-phenyl ester (45 70003057)

The title compound is prepared from 2-(4-benzyl-piperidin-1-yl)-N-(4-hydroxy-phenyl)-2-oxo-acetamide (Example 18) and methanesulfonyl chloride according to the method described in Example 154. Melting Point: 177-179° C. (water)

EXAMPLE 136

N-(2,3-Dioxo-2,3-dihydro-1H-indol-5-yl)-2-[4-(4-fluoro-benzyl)-piperidin-1-yl]-2-oxo-acetamide (45 70002570)

The title compound is prepared from 5-amino1H-indole-2,3-dion [Helv. Chim-Acta 19, 1327. (1936)] and [4-(4-fluoro-benzyl)-piperidin-1-yl]-oxo-acetic-acid (Example 1b) according to the method described in Example 1c. Melting Point: 205-206° C. (diethylether)

EXAMPLE 137

2-(4-Benzyl-piperidin-1-yl)-N-(2,3-dioxo-2,3-dihydro-1H-indol-5-yl)-2-oxo-acetamide (45 70002616)

The title compound is prepared from 5-amino-1H-indole-2,3-dion [Helv. Chim-Acta 19, 1327. (1936)] and (4-benzyl-piperidin-1-yl)-oxo-acetic-acid (Example 5b) according to the method described in Example 1c. Melting Point: 234-236° C. (diethylether)

EXAMPLE 138

2-[4-(4-Methyl-benzyl)-piperidin-1-yl)-2-oxo-N-(2-oxo-2,3-dihydro-1H-benzimidazol-5-yl)-acetamide (45 80002201)

The title compound is prepared from [4-(4-methyl-benzyl)-piperidin-1-yl]-oxo-acetic acid (Example 119b) and 5-amino-1,3-dihydro-benzimidazole-2-one according to the method described in Example 1c. Melting Point: >280° C. (diethylether)

EXAMPLE 139

2-[4-(4-Methyl-benzyl)-piperidin-1-yl)-2-oxo-N-(2-oxo-1,2,3,4-tetrahidro-quinolin-6-yl-acetamide (45 80002221)

The title compound is prepared from [4-(4-methyl-benzyl)-piperidin-1-yl]-oxo-acetic acid (Example 119b) and 6-amino-3,4-dihydro-1H-quinoline-2-one [J.Chem. Soc., 183. (1969)] according to the method described in Example 2. Melting Point: 209-213° C. (water)

EXAMPLE 140

2-(4-Benzyl-piperidin-1-yl)-N-(4-methylamino-phenyl)-2-oxo-acetamide hydrochloride (45 70003071)

The title compound is prepared from N-methyl-benzene-1,4-diamine [J. Chem. Soc., 395. (1944)] and (4-benzyl-piperidin-1-yl)-oxo-acetic-acid (Example 5b) according to the method described in Example 1c. Melting Point: 227-228° C. (ethyl acetate)

EXAMPLE 141

N-(2,2-Dioxo-2,3-dihydro-1H-2$\lambda^6$-benzo[c]isothiazol-5-yl)-2-[4-(4-methyl-benzyl)-piperidin-1-yl)-2-oxo-acetamide (45 70003031)

The title compound is prepared from [4-(4-methyl-benzyl)-piperidin-1-yl]-oxo-acetic acid (Example 119b) and 5-amino-1,3-dihydro-2,1-benzisothiazole-2,2-dioxide according to the method described in Example 94. Melting Point: 186° C. (isopropanol)

EXAMPLE 142

2-[4-(4-Fluoro-benzyl)-piperidin-1-yl]-N-(2-oxo-2,3-dihydro-1H-benzoxazol-6-yl)-acetamide (45 70001655)

142a) 2-Chloro-N-(2-oxo-2,3-dihydro-benzoxazol-6-yl)-acetamide

To a stirred solution of 1.5 g (10 mmol) of 6-amino-3H-bezonzoxazol-2-one and 3.4 ml (24 mmol) of triethylamine in 90 ml of chloroform 2 ml (24 mmol) of chloroacetyl chloride in 20 ml of chloroform is added dropwise below 10° C., and the reaction mixture is stirred at room temperature for 10 hours. The reaction mixture is concentrated and 100 ml of 8% sodium hydrogencarbonate solution is added to the residue. The precipitated product is filtered off, and washed with water to yield 1.76 g (78%) of the title compound. Melting Point: 228-231° C. (water)

142b) 2-[4-(4-Fluoro-benzyl)-piperidin-1-yl]-N-(2-oxo-2,3-dihydro-1H-benzoxazol-6-yl)-acetamide A mixture of 0.91 g (4 mmol) of 2-chloro-N-(2-oxo-2,3-dihydro-benzoxazol-6-yl)-acetamide, 0.7 g (4 mmol) of potassium iodide, 1.2 ml (8 mmol) of triethylamine, 0.7 g (3 mmol) of 4-(4-fluoro-benzyl)-piperidine hydrochloride and 50 ml of acetonitrile is refluxed for 20 hours. The reaction mixture is concentrated and 30 ml of water and 30 ml of chloroform are added to the residue. The organic layer is separated and the water phase is extracted three times with 10 ml of chloroform. The combined organic layers are dried over sodium sulfate, concentrated and the residue is purified by column chromatography using Kieselgel 60 adsorbent (Merck) and chloroform methanol=97:3 as eluent to yield 0.3 g (26%) of the title compound. Melting Point: 232-234° C. (diethylether)

EXAMPLE 143

2-(4-Benzyl-piperidin-1-yl)-N-(2-oxo-2,3-dihydro-1H-indol-5-yl)-acetamide (45 70001712)

143a) 2-Chloro-N-(2-oxo-2,3-dihydro-1H-indol-5-yl)-acetamide

The title compound is prepared from 5-amino-1,3-dihydro-indol-2-one and chloroacetyl chloride according to the method described in Example 142a. Melting Point: 166-170° C. (water)

143b) 2-(4-Benzyl-piperidin-1-yl)-N-(2-oxo-2,3-dihydro-1H-indol-5-yl)-acetamide

A mixture of 0.9 g (4 mmol) of 2-chloro-N-(2-oxo-2,3-dihydro-1H-indol-5-yl)-acetamide, 0.7 g (4 mmol) of potassium iodide, 0.6 ml (4 mmol) of triethylamine, 0.53 ml (3 mmol) of 4-benzyl-piperidine and 50 ml of acetonitrile is refluxed for 20 hours. The reaction mixture is concentrated and 30 ml of water and 30 ml of chloroform are added to the residue. The organic layer is separated and the water phase is extracted three times with 10 ml of chloroform. The combined organic layers are dried over sodium sulfate, concentrated and the residue is treated with diethylether and the precipitated crystals are filtered off to yield 0.7 g (64%) of the title compound. Melting Point: 176-180° C. (diethylether)

EXAMPLE 144

2-[4-(4-Fluoro-benzyl)-piperidin-1-yl]-N-(2-oxo-2,3-dihydro-1H-indol-5-yl)-acetamide (45 70001758)

The title compound is prepared from 2-chloro-N-(2-oxo-2,3-dihydro-1H-indol-5-yl)acetamide (Example 143a) and 4-(4-fluoro-benzyl)-piperidine hydrochloride according to the method described in Example 142b. Melting Point: 178-180° C. (diethylether)

EXAMPLE 145

2-(4-Benzyl-piperidin-1-yl)-N-(4-cyano-phenyl)-acetamide (45 70001822)

The title compound is prepared from 2-chloro-N-(4-cyano-phenyl)-acetamide [J. Org. Chem., 23, 141. (1958)] and 4-benzyl-piperidine according to the method described in Example 142b. Melting Point: 120-124° C. (diethylether)

EXAMPLE 146

2-(4-Benzyl-piperidin-1-yl)-N-(2-oxo-2,3-dihydro-benzoxazol-6-yl)-acetamide (45 70001825)

The title compound is prepared from 2-chloro-N-(2-oxo-2,3-dihydro-benzoxazol-6-yl)-acetamide (Example 142a) and 4-benzyl-piperidine according to the method described in Example 142b. Melting Point: 210-212° C. (water)

EXAMPLE 147

2-(4-Benzyl-piperidin-1-yl)-N-(1H-indazol-5-yl)-acetamide (45 70001894)

147a) 2-Chloro-N-(1H-indazol-5-yl)-acetamide

The title compound is prepared from 5-aminoindazol (Aldrich) and chloroacetyl chloride according to the method described in Example 142a. Melting Point: 175-178° C. (diethylether)

147b) 2-(4-Benzyl-piperidin-1-yl)-N-(1H-indazol-5-yl)-acetamide

The title compound is prepared from 2-chloro-N-(1H-indazol-5-yl)-acetamide and 4-benzyl-piperidine (Aldrich) according to the method described in Example 142b. Melting Point: 170-174° C. (diethylether)

EXAMPLE 148

2-[4-(4-Fluoro-benzyl)-piperidin-1-yl]-N-(1H-indazol-5-yl)-acetamide (45 70002014)

The title compound is prepared from 2-chloro-N-(1H-indazol-5-yl)-acetamide (Example 147a) and 4-(4-fluoro-benzyl)-piperidine according to the method described in Example 142b. Melting Point: 149-152° C. (diethylether)

EXAMPLE 149

2-[4-(4-Fluoro-benzyl)-piperidin-1-yl]-N-(1H-indazol-6-yl)-acetamide (45 70002012)

149a) 2-Chloro-N-(1H-indazol-6-yl)-acetamide

The title compound is prepared from 6-aminoindazol (Aldrich) and chloroacetyl chloride according to the method described in Example 142a. Melting Point: 155-160° C. (diethylether)

149b) 2-[4-(4-Fluoro-benzyl)-piperidin-1-yl]-N-(1H-indazol-6-yl)-acetamide

The title compound is prepared from 2-chloro-N-(1H-indazol-6-yl)-acetamide and 4-(4-fluoro-benzyl)-piperidine according to the method described in Example 142b. Melting Point: 135-137° C. (diethylether)

EXAMPLE 150

2-(4-Benzyl-piperidin-1-yl)-N-(1H-indazol-6-yl)-acetamide (45 70002013)

The title compound is prepared from 2-chloro-N-(1H-indazol-6-yl)-acetamide (Example 149a) and 4-benzyl-piperidine according to the method described in Example 142b. Melting Point: 165-169° C. (diethylether)

EXAMPLE 151

2-(4-Benzyl-piperidine-1-yl)-N-(1H-benzimidazol-5-yl)-acetamide (45 70002016)

151a) 2-Chloro-N-(1H-benzimidazol-5-yl)-acetamide

The title compound is prepared as an oil from 5-aminobenzimidazol and chloroacetyl chloride according to the method described in Example 142a.

151b) 2-(4-Benzyl-piperidine-1-yl)-N-(1H-benzimidazol-5-yl)-acetamide

The title compound is prepared from 2-chloro-N-(1H-benzimidazol-5-yl)-acetamide and 4-benzyl-piperidine according to the method described in Example 142b. Melting Point: 185-189° C. (diethylether)

EXAMPLE 152

2-[4-(4-Fluoro-benzyl)-piperidin-1-yl]-N-(1H-benzimidazol-5-yl)-acetamide (45 70002140)

The title compound is prepared from 2-chloro-N-(1H-benzimidazol-5-yl)-acetamide (Example 151 a) and 4-(4-fluoro-benzyl)-piperidine according to the method described in Example 142b. Melting Point: 203.5-204.5° C. (diethylether)

EXAMPLE 153

2-(4-Benzyl-piperidin-1-yl)-N-(3-oxo-3,4-dihydro-2H-benzo[1,4]oxazin-7-yl)-acetamide (45 70002189)

153a) 2-Chloro-N-(3-oxo-3,4-dihydro-2H-benzo[1,4]oxazin-7-yl)-acetamide

The title compound is prepared from 7-amino-4H-benzo[1,4]oxazine-3-one and chloroacetyl chloride according to the method described in Example 142a. Melting Point: 210-215° C. (diethylether)

153b) 2-(4-Benzyl-piperidin-1-yl)-N-(3-oxo-3,4-dihydro-2H-benzo[1,4]oxazin-7-yl)-acetamide The title compound is prepared from 2-chloro-N-(3-oxo-3,4-dihydro-2H-benzo[1,4]oxazin-7-yl)-acetamide and 4-benzyl-piperidine according to the method described in Example 142b. Melting Point: 184-188° C. (diethylether)

EXAMPLE 154

2-[4-(4-Fluoro-benzyl)-piperidin-1-yl]-N-(3-oxo-3,4-dihydro-2H-benzo[1,4]oxazin-7-yl)-acetamide (45 70002190)

The title compound is prepared from 2-chloro-N-(3-oxo-3,4-dihydro-2H-benzo[1,4]oxazin-7-yl)-acetamide (Example 153a) and 4-(4-fluoro-benzyl)-piperidine according to the method described in Example 142b. Melting Point: 209-211° C. (diethylether)

EXAMPLE 155

2-(4-Benzyl-piperidin-1-yl)-N-(3-oxo-3,4-dihydro-2H-benzo[1,4]oxazin-6-yl)-acetamide (45 70002191)

155a) 2-Chloro-N-(3-oxo-3.4-dihydro-2H-benzo1.41oxazin-6-yl)-acetamide

The title compound is prepared from 6-amino-4H-benzo[1,4]oxazin-3-one and chloroacetyl chloride according to the method described in Example 142a. Melting Point: 258-261.5° C. (diethylether)

155b) 2-(4-Benzyl-piperidin-1-yl)-N-(3-oxo-3,4-dihydro-2H-benzo[1,4]oxazin-6-yl)-acetamide The title compound is prepared from 2-chloro-N-(3-oxo-3,4-dihydro-2H-benzo[1,4]oxazin-6-yl)-acetamide and 4-benzyl-piperidine according to the method described in Example 142b. Melting Point: 220-222° C. (diethylether)

EXAMPLE 156

2-[4-(4-Fluoro-benzyl)-piperidin-1-yl]-N-(3-oxo-3,4-dihydro-2H-benzo[1,4]oxazin-6-yl)-acetamide (45 70002192)

The title compound is prepared from 2-chloro-N-(3-oxo-3,4-dihydro-2H-benzo[1,4]oxazin-6-yl)-acetamide (Example 155a) and 4-(4-fluoro-benzyl)-piperidine according to the method described in Example 142b. Melting Point: 185-187° C. (diethylether)

EXAMPLE 157

2-(4-Phenoxy-piperidin-1-yl)-N-(3-oxo-3,4-dihydro-2H-benzo[1,4]oxazin-7-yl)-acetamide (45 70002243)

The title compound is prepared from 2-chloro-N-(3-oxo-3,4-dihydro-2H-benzo[1,4]oxazin-7-yl)-acetamide (Example 153a) and 4-phenoxy-piperidine according to the method described in Example 142b. Melting Point: 206-208° C. (diethylether)

EXAMPLE 158

2-(4-Phenoxy-methyl-piperidine-1-yl)-N-(3-oxo-3,4-dihydro-2H-benzo[1,4]oxazin-7-yl)-acetamide (45 70002245)

The title compound is prepared from 2-chloro-N-(3-oxo-3,4-dihydro-2H-benzo[1,4]oxazin-7-yl)-acetamide (Example 153a) and 4-phenoxy-methyl-piperidine according to the method described in Example 142b. Melting Point: 172-175° C. (diethylether)

EXAMPLE 159

2-(4-Benzyloxy-piperidin-1-yl)-N-(3-oxo-3,4-dihydro-2H-benzo[1,4]oxazin-7-yl)-acetamide (45 70002252)

The title compound is prepared from 2-chloro-N-(3-oxo-3,4-dihydro-2H-benzo[1,4]oxazin-7-yl)-acetamide (Example 153a) and 4-benzyloxy-piperidine according to the method described in Example 142b. Melting Point: 238-240° C. (diethylether)

EXAMPLE 160

2-(4-Phenethyl-piperidin-1-yl)-N-(3-oxo-3,4-dihydro-2H-benzo[1,4]oxazine-7-yl)-acetamide (45 70002253)

The title compound is prepared from 2-chloro-N-(3-oxo-3,4-dihydro-2H-benzo[1,4]oxazine-7-yl)-acetamide (Example 153a) and 4-phenethyl-piperidine according to the method described in Example 142b. Melting Point: 200-203° C. (diethylether)

EXAMPLE 161

2-(4-Benzyl-piperidin-1-yl)-N-(2-oxo-2,3-dihydro-1H-benzoxazol-6-yl)-propionamide (45 70002233)

161a) 2-(4-Benzyl-piperidin-1-yl)-propionic acid ethyl ester

A mixture of 10.0 g (57.0 mmol) of 4-benzyl-piperidin, 10.0 g (72.4 mmol) of potassium carbonate, 7.5 ml (57.7 mmol) of ethyl-2-bromopropionate and 100 ml of acetone is refluxed for 1 hour. The reaction mixture is filtered and the filtrate is concentrated. The crude product is used in the next step.

161b) 2-(4-Benzyl-piperidin-1-yl)-propionic acid hydrochloride

To a stirred solution of 15.7 g (57.0 mmol) of 2-(4-benzyl-piperidin-1-yl)-propionic acid ethyl ester in 50 ml of ethanol and 50 ml of water 3.0 g (75.0 mmol) of sodium hydroxide is added. The reaction mixture is stirred for 6 hours at room temperature. The ethanol is distilled off under reduced pressure. The reaction mixture is acidified with 2M hydrochloric acid and the product is extracted with chloroform. The combined organic layers are washed with water, dried over sodium sulfate and concentrated to yield 13.1 (92.9%) of the title compound. Melting Point: oil.

161c) 2-(4-Benzyl-piperidin-1-yl)-N-(2-oxo-2,3-dihydro-1H-benzoxazol-6-yl)-propionamide A mixture of 0.5 g (2.0 mmol) of 2-(4-benzyl-piperidin-1-yl)-propionic acid hydrochloride, 0.3 ml (2.1 mmol) of triethylamine, 0.36 g (2.0 mmol) of 6-amino-3H-benzoxazol-2-one, 0.8 g (2.1 mmol) of HBTU and 10 ml of dimethylformamide is stirred at room temperature for 24 hours. The reaction mixture is concentrated and the residue is purified by column chromatography using Kieselgel 60 (Merck) as adsorbent and toluene:methanol=4:1 as eluent. The product is crystallized with diethylether to yield 0.095 g (11.6%) of the title compound. Melting Point: 116-118° C. (diethylether).

EXAMPLE 162

2-(4-Benzyl-piperidin-1-yl)-N-(2-oxo-2,3-dihydro-1H-indol-5-yl)-propionamide (45 70002368)

The title compound is prepared from 5-amino-1,3-dihydro-indol-2-one and 2-(4-benzyl-piperidin-1-yl)-propionic acid hydrochloride (Example 161b) according to the method described in Example 161c. Melting Point: 153-155° C. (diethylether).

EXAMPLE 163

N-(2-oxo-2,3-dihydro-1H-benzoxazol-6-yl)-2-(4-phenoxy-piperidin-1-yl)-acetamide 4570002406

163a) (4-Phenoxy-piperidin-1-yl)-acetic acid ethyl ester

The title compound is prepared from 4-phenoxy-piperidine and ethyl-bromoacetate according to the method described in Example 161a. Melting Point: oil.

163b) (4-Phenoxy-piperidin-1-yl)-acetic acid hydrochloride

The title compound is prepared from (4-phenoxy-piperidin-1-yl)-acetic acid ethyl ester according to the method described in Example 161b. Melting Point: 190-196° C. (water).

163c) N-(2-oxo-2,3-dihydro-1H-benzoxazol-6-yl)-2-(4-phenoxy-piperidin-1-yl)-acetamide The title compound is prepared from (4-phenoxy-piperidin-1-yl)-acetic acid hydrochloride and 6-amino-3H-benzoxazol-2-one according to the method described in Example 161c. Melting Point: 193-195° C. (diethylether)

EXAMPLE 164

2-(4-Benzyl-piperidin-1-yl)-N-(2-thioxo-2,3-dihydro-1H-benzoxazol-6-yl)-acetamide (45 70002447)

164a) (4-Benzyl-piperidin-1-yl)-acetic acid ethyl ester

The title compound is prepared from 4-benzyl-piperidine and ethyl-bromoacetate according to the method described in Example 161a. Melting Point: oil.

164b) (4-Benzyl-piperidin-1-yl)-acetic acid hydrochloride

The title compound is prepared from (4-benzyl-piperidin-1-yl)-acetic acid ethyl ester according to the method described in Example 161b. Melting Point: 222° C. (water).

164c) 2-(4-Benzyl-piperidin-1-yl)-N-(2-thioxo-2,3-dihydro-1H-benzoxazol-6-yl)-acetamide The title compound is prepared from (4-benzyl-piperidin-1-yl)-acetic acid hydrochloride and 6-amino-3H-benzoxazole-2-thione according to the method described in Example 161c. Melting Point: 183-184° C. (isopropanol)

EXAMPLE 165

N-(4-Cyano-phenyl)-2-[4-(4-fluoro-benzyl)-piperidin-1-yl]-acetamide (45 70001831)

The title compound is prepared from 2-chloro-N-(4-cyano-phenyl)-acetamide and 4-(4-fluoro-benzyl)-piperidine hydrochloride according to the method described in Example 142b. Melting Point: 113-116° C. (diethylether)

EXAMPLE 166

2-(4-Benzyl-piperidin-1-yl)-N-(3-cyano-phenyl)-acetamide (45 70001864)

166a) 2-Chloro-N-(3-cyano-phenyl)-acetamide

The title compound is prepared from 3-amino-benzonitrile (Aldrich) and chloroacetyl chloride according to the method described in Example 142a. Melting Point: 144-146° C. (water)

166b) 2-(4-Benzyl-piperidin-1-yl)-N-(3-cyano-phenyl)-acetamide

The title compound is prepared from 2-chloro-N-(3-cyano-phenyl)-acetamide and 4-benzyl-piperidine according to the method described in Example 142b. Melting Point: 88-90° C. (diethylether)

EXAMPLE 167

N-(3-Cyano-phenyl)-2-[4-(4-fluoro-benzyl)-piperidin-1-yl]-acetamide (45 70001865)

The title compound is prepared from 2-chloro-N-(3-cyano-phenyl)-acetamide (Example 166a) and 4-(4-fluoro-benzyl)-piperidine hydrochloride according to the method described in Example 142b. Melting Point: 101-103° C. (diisopropylether)

EXAMPLE 168

2-(4-Benzyl-piperidin-1-yl)-N-[4-(1H-tetrazol-5-yl)-phenyl]-acetamide hydrochloride (45 70001985)

A mixture of 0.4 g (1.2 mmol) of (2-(4-benzyl-piperidin-1-yl)-N-(4-cyano-phenyl)-acetamide (Example 145), 0.5 g (2.4 mmol) of azidotrimethyltin (Aldrich) and 20 ml of toluene is refluxed for 20 hours. The precipitated crystals are filtered off and treated with 20 ml of N hydrochloric acid to yield 0.26 g (56%) of the title compound. Melting Point: >260° C. (water)

EXAMPLE 169

2-[4-(4-Fluoro-benzyl)-piperidin-1-yl]-N-[4-(1H-terazol-5-yl)-phenyl]-acetamide hydrochloride (45 70002021)

The title compound is prepared from N-(4-cyano-phenyl)-2-[4-(4-fluoro-benzyl)-piperidin-1-yl]-acetamide (Example 165) and azidotrimethyltin according to the method described in Example 168. Melting Point: 251-257° C. (water)

EXAMPLE 170

2-(4-Benzyl-piperidin-1-yl)-N-[3-(1H-tetrazol-5-yl)-phenyl]-acetamide hydrochloride (45 70002022)

The title compound is prepared from 2-(4-benzyl-piperidine-1-yl)-N-(3-cyano-phenyl)-acetamide (Example 166b) and azidotrimethyltin according to the method described in Example 168. Melting Point: 89-93° C. (water)

EXAMPLE 171

2-[4-(4-Fluoro-benzyl)-piperidin-1-yl]-N-[3-(1H-tetrazol-5-yl)-phenyl]-acetamide hydrochloride (45 70002023)

The title compound is prepared from N-(3-cyano-phenyl)-2-[4-(4-fluoro-benzyl)-piperidin-1-yl]-acetamide (Example 167) and azidotrimethyltin according to the method described in Example 168. Melting Point: 102-106° C. (water)

EXAMPLE 172

2-(4-Benzyl-piperidin-1-yl)-N-(3-nitro-phenyl)-acetamide (45 70002121)

The title compound is prepared from 2-chloro-N-(3-nitro-phenyl)-acetamide [Tetrahedron Lett. 39, 7459. (1998)] and 4-benzyl-piperidine according to the method described in Example 142b. Melting Point: 102-104° C. (diethylether)

EXAMPLE 173

2-(4-Benzyl-piperidin-1-yl)-N-(4-nitro-phenyl)-acetamide (45 70002122)

The title compound is prepared from 2-chloro-N-(4-nitro-phenyl)-acetamide [J. Amer. Chem. Soc. 45, 1997. (1923)] and 4-benzyl-piperidine according to the method described in Example 142b. Melting Point: 126-128° C. (diethylether)

EXAMPLE 174

N-(4-Amino-phenyl)-2-(4-benzyl-piperidin-1-yl)-acetamide dihydrochloride (45 70002199)

A mixture of 2.5 g (7 mmol) of 2-(4-benzyl-piperidin-1-yl)-N-(4-nitro-phenyl)-acetamide (Example 173), 140 ml of dimethylformamide, 0.7 g of 10% Pd/C catalyst is hydrogenated for 4 hours. The catalyst is filtered off, washed with dimethylformamide and the filtrate is concentrated. The residue is treated with diethylether and 2.5 N hydrochloric acid in ethyl acetate and the precipitated crystals are filtered off to yield 2.4 g (96%) of the title compound. Melting Point: >260° C. (diethylether-ethyl acetate)

EXAMPLE 175

N-(3-Amino-phenyl)-2-(4-benzyl-piperidin-1-yl)-acetamide dihydrochloride (45 70002200)

The title compound is prepared from 2-(4-benzyl-piperidin-1-yl)-N-(3-nitrophenyl)acetamide (Example 172) according to the method described in Example 174. Melting Point: 80-110° C. (dec.) (diethylether-ethyl acetate)

EXAMPLE 176

2-(4-Benzyl-piperidin-1-yl)-N-(3-methanesulfonylamino-phenyl)-acetamide dihydrochloride (45 70002242)

To a stirred solution of 0.36 g (1 mmol) of N-(3-aminophenyl)-2-(4-benzyl-piperidin-1-yl)-acetamide dihydrochloride (Example 175) and 0.24 ml (3 mmol) of pyridine in 10 ml of dichloromethane 0.16 ml (2 mmol) of methanesulfonyl chloride in 5 ml of dichloromethene is added dropwise below 10° C., and the reaction mixture is stirred at room temperature for 10 hours. Then 20 ml of 8% sodium hydrogencarbonate solution is added to the mixture, the organic layer is separated and the water phase is extracted three times with 10 ml of dichloromethane. The combined organic layers are washed with 20 ml of water and dried over sodium sulfate, concentrated, the residue is treated with diethylether and 2.5 N hydrochloric acid in ethyl acetate and the precipitated crystals are filtered off to yield 0.32 g (73%) of the title compound. Melting Point: 110-114° C. (diethylether-ethyl acetate)

EXAMPLE 177

N-(3-Benzylamino-phenyl)-2-(4-benzyl-piperidin-1-yl)-acetamide (45 70002264)

To a stirred solution of 0.32 g (1 mmol) of N-(3-aminophenyl)-2-(4-benzyl-piperidin-1-yl)-acetamide (Example 175), 0.1 ml (1 mmol) of benzaldehyde, 0.12 ml (2 mmol) of acetic acid in 10 ml of dichloroethane 0.32 g (1.5 mmol) of sodium triacetoxyborohydride is added in small portions below 20° C., and the reaction mixture is stirred at room temperature for 2 hours. Then 20 ml of 8% sodium hydrogencarbonate solution is added to the mixture. The organic layer is separated and the water phase is extracted three times with 10 ml of dichloromethane. The combined organic layers are washed with 20 ml of water and dried over sodium sulfate, concentrated, the residue is treated with diethylether and the precipitated crystals are filtered off to yield 0.26 g (63%) of the title compound. Melting Point: 112-114° C. (ethyl acetate)

EXAMPLE 178

2-[4-(4-Fluoro-benzyl)-piperidin-1-yl]-N-(4-nitrophenyl)-acetamide (45 70002489)

The title compound is prepared from 2-chloro-N-(4-nitrophenyl)-acetamide and 4-(4-fluoro-benzyl)-piperidine hydrochloride according to the method described in Example 142b. Melting Point: 120-123° C. (diethylether)

EXAMPLE 179

2-[4-(4-Fluoro-benzyl)-piperidin-1-yl]-N-(3-nitrophenyl)-acetamide (45 70002490)

The title compound is prepared from 2-chloro-N-(3-nitrophenyl)-acetamide and 4-(4-fluoro-benzyl-piperidine hydrochloride according to the method described in Example 142b. Melting Point: 118-120° C. (diethylether)

EXAMPLE 180

2-(4-Benzyl-piperidin-1-yl)-N-(4-methanesulfonylamino-phenyl)-acetamide (45 70002501)

180a) 2-Chloro-N-(4-methanesulfonylamino-phenyl)-acetamide

The title compound is prepared from methanesulfonic acid-(4-amino-anilide) and chloroacetyl chloride according to the method described in Example 142a. Melting Point: 174-177° C. (water)

180b) 2-(4-Benzyl-piperidin-1-yl)-N-(4-methanesulfonylamino-phenyl)-acetamide

The title compound is prepared from 2-chloro-N-(4-methanesulfonylamino-phenyl)-acetamide and 4-benzyl-piperidine according to the method described in Example 142b. Melting Point: 102-106° C. (hexane)

EXAMPLE 181

N-(4-Amino-phenyl)-2-[4-(4-fluoro-benzyl-piperidin-1-yl)-acetamide dihydrochloride (45 70002502)

The title compound is prepared from 2-[4-(4-fluoro-benzyl)-piperidin-1-yl]-N-(4-nitro-phenyl)-acetamide (Example 178) according to the method described in Example 174. Melting Point: 258° C. (dec.) (diethylether-ethyl acetate)

EXAMPLE 182

2-[4-(4-Fluoro-benzyl)-piperidin-1-yl]-N-(4-methanesulfonylamino-phenyl)-acetamide (45 70002510)

The title compound is prepared from 2-chloro-N-(4-methanesulfonylamino-phenyl)-acetamide (Example 180a) and 4-(4-fluoro-benzyl)-piperidine hydrochloride according to the method described in Example 142b. Melting Point: 169-171° C. (hexane)

EXAMPLE 183

N-(3-Amino-phenyl)-2-[4-(4-fluoro-benzyl)-piperidin-1-yl]-acetamide dihydrochloride (45 70002511)

The title compound is prepared from 2-[4-(4-fluoro-benzyl)-piperidin-1-yl]-N-(3-nitro-phenyl)-acetamide (Example 79) according to the method described in Example 174. Melting Point: 105-110° C. (diethylether-ethyl acetate)

EXAMPLE 184

N-(4-Methanesulfonylamino-phenyl)-2-[4-(methyl-p-tolyl-amino)-piperidin-1-yl]-acetamide (45 70002516)

The title compound is prepared from 2-chloro-N-(4-methanesulfonylamino-phenyl)-acetamide (Example 180) and 4-(methyl-p-tolyl-amino)-piperidine [Arzneimittel Forschung/Drug Research 44(II), 989. (19994)]) according to the method described in Example 142b. Melting Point: 128-130° C. (diethylether)

EXAMPLE 185

N-(4-Acetylamino-phenyl)-2-[4-(4-fluoro-benzyl)-piperidin-1-yl]-acetamide (45 70002517)

To a stirred solution of 0.38 g (1 mmol) of N-(4-aminophenyl)-2-[4-(4-fluoro-benzyl)-piperidin-1-yl]-acetamide dihydrochloride (Example 181) and 0.28 ml (2 mmol) of triethylamine in 10 ml of dichloromethane 0.1 ml (1 mmol) of acetic anhydride in 2 ml of dichloromethane is added dropwise below 10° C., and the reaction mixture is stirred at room temperature for 3 hours. The solvent is evaporated and the residue is treated with water and the crystals are filtered off to yield 0.15 g (39%) of the title compound. Melting Point: 173-180° C. (water)

EXAMPLE 186

N-(4-Benzylamino-phenyl)-2-[4-(4-fluoro-benzyl)-piperidin-1-yl]-acetamide dihydrochloride (45 70002560)

The title compound is prepared from N-(4-aminophenyl)-2-[4-(4-fluoro-benzyl)-piperidin-1-yl]-acetamide dihydrochloride (Example 181) and benzaldehyde according to the method described in Example 177. Melting Point: 84-106° C. (dec.) (diethylether-ethyl acetate)

EXAMPLE 187

N-(4-Benzylamino-phenyl)-2-(4-benzyl-piperidin-1-yl)-acetamide dihydrochloride (45 70002561)

The title compound is prepared from N-(4-amino-phenyl)-2-(4-benzyl-piperidin-1-yl)-acetamide dihydrochloride (Example 174) and benzaldehyde according to the method described in Example 177. Melting Point: 147° C. (dec.) (diethylether-ethyl acetate)

EXAMPLE 188

2-[4-(4-Fluoro-benzyl)-piperidin-1-yl]-acetamide-N-(3-methanesulfonylamino-phenyl)-acetamide hydrochloride (45 70002612)

The title compound is prepared from N-(3-amino-phenyl)-2-[4-(4-fluoro-benzyl)-piperidin-1-yl]-acetamide dihydrochloride (Example 183) and methanesulfonyl chloride according to the method described in Example 176. Melting Point: 85-90° C. (dec.) (diethylether- ethyl acetate)

EXAMPLE 189

N-(3-Benzylamino-phenyl)-2-[4-(4-fluoro-benzyl)-piperidin-1-yl]-acetamide (45 70002613)

The title compound is prepared from N-(3-amino-phenyl)-2-[4-(4-fluoro-benzyl)-piperidin-1-yl]-acetamid dihydrochloride (Example 183) and benzaldehyde according to the method described in Example 177. Melting Point: 98-100° C. (diethylether-hexane)

EXAMPLE 190

2-(4-Benzyl-piperidin-1-yl)-N-(4-methoxy-phenyl)-acetamide (45 70002794)

The title compound is prepared from 2-chloro-N-(4-methoxy-phenyl)-acetamide [J. Heterocycl. Chem., 32, 1429. (1995)] and 4-benzyl-piperidine according to the method described in Example 143b. Melting Point: 81-83° C. (hexane)

EXAMPLE 191

2-[4-(4-Fluoro-benzyl)-piperidin-1-yl]-N-(4-methoxy-phenyl)-acetamide (45 70002796)

The title compound is prepared from 2-chloro-N-(4-methoxyphenyl)-acetamide and 4-benzyl-piperidine according to the method described in Example 143b. Melting Point: 121-124° C. (hexane)

EXAMPLE 192

2-(4-Benzyl-piperidin-1-yl)-N-(4-hydroxy-phenyl)-acetamide (45 70002863)

To a stirred solution of 0.68 g (2 mmol) of 2-(4-benzyl-piperidin-1-yl)-N-(4-methoxy-phenyl)-acetamide (Example 190) and in 30 ml of dichloromethane 0.95 ml (10 mmol) of boron tribromide in 9 ml of dichloromethane is added dropwise at −20° C., and the reaction mixture is stirred at room temperature for 10 hours. The reaction mixture is concentrated. Then 30 ml of 8% sodium hydrogenecarbonate solution and 20 ml of chloroform are added to the mixture. The organic layer is separated and the water phase is extracted three times with 20 ml of chloroform. The combined organic layers are dried over sodium sulfate, concentrated and the residue is purified by column chromatography using Kieselgel 60 as adsorbent (Merck) and chloroform:methanol=9:1 as eluent to yield 0.4 g (62%) of the title compound. Melting Point: 66-70° C. (hexane)

EXAMPLE 193

2-[4-(4-Fluoro-benzyl)-piperidin-1-yl]-N-(4-hydroxy-phenyl)-acetamide (45 70002864)

The title compound is prepared from 2-[4-(4-fluoro-benzyl)-piperidin-1-yl]-N-(4-methoxy-phenyl)-acetamide (Example 191) according to the method described in Example 192. Melting Point: 70-77° C. (hexane)

EXAMPLE 194

2-[4-(4-Fluoro-benzyl)-piperidin-1-yl]-N-(2-oxo-2,3-dihydro-1H-benzoxazol-6-yl)-acetamide hydrochloride (45 70002909)

To a stirred suspension of 1,5 g (3.9 mmol) of 2-[4-(4-fluoro-benzyl)-piperidin-1-yl]-N-(2-oxo-2,3-dihydro-1H-benzoxazol-6-yl)-acetamide (Example 142b) in 40 ml of diethylether is added 4 ml of 2.5 N hydrochloric acid in ethyl acetate. The mixture is stirred for 1 h at room temperature, the crystals are filtered off and washed with diethylether to yield 1.64 g (100%) of the title compound. Melting Point: 210-216° C. (dec.) (diethylether)

EXAMPLE 195

2-(4-Benzyl-piperidin-1-yl)-N-(2-oxo-2,3-dihydro-1H-benzimidazol-5-yl)-acetamide (45 70002237)

195a) 2-Chloro-N-(2-oxo-2,3-dihydro-1H-benzimidazol-5-yl)-acetamide
The title compound is prepared from 5-amino-2-oxo-2,3-dihydro-benzimidazol and chloroacetyl chloride according to the method described in Example 142a. Melting Point: >280° C. (water)
195b) 2-(4-Benzyl-piperidin-1-yl)-N-(2-oxo-2,3-dihydro-1H-benzimidazol-5-yl)-acetamide The title compound is prepared from 4-benzyl-piperidine and 2-chloro-N-(2-oxo-2,3-dihydro-1H-benzimidazol-5-yl)-acetamide according to the method described in Example 142b. Melting Point: 270° C. (diethylether

EXAMPLE 196

2-[4-(4-Fluoro-benzyl)-piperidin-1-yl]-N-(2-oxo-2,3-dihydro-1H-benzoimidazol-yl)-acetamide (45 70002465)

The title compound is prepared from 4-(4-fluorobenzyl)-piperidine and 2-chloro-N-(2-oxo-2,3-dihydro-1H-benzimidazol-5-yl)-acetamide (Example 195a) according to the method described in Example 142b. Melting Point: 273-274° C. (diethylether)

EXAMPLE 197

5-{2-[4-(4-Fluoro-benzyl)-piperidin-1-yl]-2-oxo-ethylamino}-1,3-dihydro-benzoimidazol-2-one (45 70001863)

197a) 2-Chloro-1-[4-(4-fluoro-benzyl)-piperidin-1-yl]-ethanone

The title compound is prepared from 4-(4-fluoro-benzyl)-piperidine and chloroacetyl chloride according to the method described in Example 142a. Melting Point: 85-87° C. (water)
197b) 5-{2-[4-(4-Fluoro-benzyl)-piperidin-1-yl]-2-oxo-ethylamino}-1,3-dihydro-benzimidazol-2-one The title compound is prepared from 2-chloro-1-[4-(4-fluoro-benzyl)-piperidine-1-yl]-ethanone and 5-amino-1,3-dihydro-benzimidazol-2-one according to the method described in Example 142b. Melting Point: 249-251° C. (diethylether)

EXAMPLE 198

6-{2-[4-(4-Fluoro-benzyl)-piperidin-1-yl]-2-oxo-ethylamino}-3H-benzoxazol-2-one (45 70001944)

The title compound is prepared from 2-chloro-1-[4-(4-fluoro-benzyl)-piperidin-1-yl]-ethanone (Example 197a) and 6-amino-3H-benzoxazol-2-one according to the method described in Example 142b. Melting Point: 202-205° C. (diethylether)

EXAMPLE 199

1-[4-(4-Fluoro-benzyl)-piperidin-1-yl]-2-(1H-indazol-5-yl-amino)-ethanone (45 70001843)

The title compound is prepared from 5-aminoindazol (Aldrich) and 2-chloro-1-[4-(4-fluoro-benzyl)-piperidin-1-yl]-ethanone (Example 197a) according to the method described in Example 142b. Melting Point: 113-114° C. (diethylether)

EXAMPLE 200

1-(4-Benzyl-piperidin-1-yl)-2-(1H-indazol-5-yl-amino)-ethanone (45 70001949)

200a) 2-Chloro-1-(4-benzyl-piperidin-1-yl)-ethanone
The title compound is prepared from 4-benzyl-piperidine and chloroacetyl chloride according to the method described in Example 142a. Melting Point: 42-47° C.

200b) 1-(4-benzyl-piperidin-1-yl)-2-(1H-indazol-5-yl-amino)-ethanone

The title compound is prepared from 5-aminoindazol and 2-chloro-1-(4-benzyl-piperidin-1-yl)-ethanone according to the method described in Example 142b. Melting Point: 153-155° C. (diethylether)

EXAMPLE 201

2-[4-(4-Fluoro-benzyl)-piperidin-1-yl]-2-(3-oxo-3,4-dihydro-2H-benzo[1,4]oxazine-7-yl-amino)-ethanone (45 70002015)

The title compound is prepared from 7-amino-4H-benzo[1,4]oxazine-3-one and 2-chloro-1-[4-(4-fluoro-benzyl)-piperidin-1-yl]-ethanone (Example 197a) according to the method described in Example 142b. Melting Point: 156-161° C. (diethylether).

EXAMPLE 202

2-(4-Benzyl-piperidin-1-yl)-2-(3-oxo-3,4-dihydro-2H-benzo[1,4]oxazine-7-yl-amino)-ethanone (45 70002104)

The title compound is prepared from 7-amino-4H-benzo[1,4]oxazine-3-one and 2-chloro-1-(4-benzyl-piperidin-1-yl)-ethanone (Example 200a) according to the method described in Example 142b. Melting Point: 172-175° C. (diethylether).

EXAMPLE 203

1-[4-(4-Fluoro-benzyl)-piperidin-1-yl]-2-(1H-indazol-6-yl-amino)-ethanone (45 70001817)

The title compound is prepared from 6-aminoindazol and 2-chloro-1-[4-(4-fluoro-benzyl)-piperidin-1-yl]-ethanone (Example 197a) according to the method described in Example 142b. Melting Point: 181-183° C. (diethylether)

EXAMPLE 204

1-(4-Benzyl-piperidin-1-yl)-2-(1H-indazol-6-yl-amino)-ethanone (45 70001950)

The title compound is prepared from 6-aminoindazol and 2-chloro-1-(4-benzyl-piperidin-1-yl)-ethanone (Example 200a) according to the method described in Example 142b. Melting Point: 179-182° C. (diethylether)

EXAMPLE 205

1-[4-(4-Fluoro-benzyl)-piperidin-1-yl]-2-(3-oxo-3,4-dihydro-2H-benzo[1,4]oxazin-6-yl-amino)-ethanone (45 70002176)

The title compound is prepared from 6-amino-4H-benzo[1,4]oxazin-3-one and 2-chloro-1-[4-(4-fluoro-benzyl)-piperidin-1-yl]-ethanone (Example 197a) according to the method described in Example 142b. Melting Point: 220-223° C. (diethylether)

EXAMPLE 206

N-(4-{2-[4-(4-Fluoro-benzyl)-piperidin-1-yl]-2-oxo-ethylamino}-phenyl)-metanesulfonamide (45 70002491)

A mixture of 1.08g (4 mmol) of 2-chloro-1-[4-(4-fluoro-benzyl)-piperidin-1-yl]-ethanone (Example 197a), 1.5 g (8 mmol) of methanesulfonic acid-(4-amino-anilide), 0.68 g (4 mmol) of potassium iodide, 1.2 ml (8 mmol) of triethylamine and 40 ml of toluene is refluxed for 3 hours. The reaction mixture is concentrated and 30 ml of water and 30 ml of chloroform are added to the residue The organic layer is separated and the water phase is extracted three times with 10 ml of chloroform. The combined organic layers are dried over sodium sulfate. Concentrated and the residue is purified by column chromatography using Kieselgel 60 adsorbent (Merck) and chloroform:methanol=99:1 as eluent to yield 0.96 g (57%) of the title compound. Melting Point: 177-181° C. (diisopropylether)

EXAMPLE 207

1-(4-Benzyl-piperidin-1-yl)-2-(2-oxo-2,3-dihydro-benzothiazol-6-yl-amino)-ethanone (45 70003033)

The title compound is prepared from 6-amino-3H-benzothiazole-2-one and 2-chloro-1-(4-benzyl-piperidin-1-yl)-ethanone (Example 200a) according to the method described in Example 206. Melting Point: 196-199° C. (diethylether)

EXAMPLE 208

1-(4-p-Tolyloxy-piperidin-1-yl)-2-(2-oxo-2,3-dihydro-benzothiazol-6-yl-amino)-ethanone (45 70003072)

208a) 2-chloro-1-(4-p-tolyloxy-piperidin-1-yl)-ethanone
The title compound is prepared from 4-p-tolyloxy-piperidine and chloroacetyl chloride according to the method described in Example 142a. Melting Point: oil
208b) 1-(4-p-Tolyloxy-piperidin-1-yl)-2-(2-oxo-2,3-dihydro-benzothiazole-6-yl-amino)-ethanone
The title compound is prepared from 6-amino-3H-benzothiazole-2-one and 2-chloro-1-(4-p-tolyloxy-piperidin-1-yl)-ethanone according to the method described in Example 206. Melting Point: 189-191° C. (diethylether)

EXAMPLE 209

2-(4-p-Tolyloxy-piperidin-1-yl)-2-(3-oxo-3,4-dihydro-2H-benzo[1,4]oxazin-7-yl-amino)-ethanone (45 70003118)

The title compound is prepared from 7-amino-4H-benzo[1,4]oxazin-3-one and 2-chloro-1-(4-p-tolyloxy-piperidin-1-yl) ethanone (Example 208a) according to the method described in Example 206. Melting Point: 223-224° C. (diethylether)

EXAMPLE 210

1-[4-(4-Fluoro-benzyl)-piperidin-1-yl]-2-(2-oxo-2,3-dihydro-benzothiazol-6-yl-amino)-ethanone (45 70003032)

The title compound is prepared from 6-amino-3H-benzothiazol-2-one and 2-chloro-1-[4-(4-fluoro-benzyl)-piperidin-1-yl]-ethanone (Example 197a) according to the method described in Example 206. Melting Point: 149-155° C. (diethylether)

EXAMPLE 211

5-{2-[4-(4-Fluoro-benzyl)-piperidin-1-yl]-2-(2-oxo-ethylamino}-1,3-dihydro-indol-2-one (45 70002509)

The title compound is prepared from 5-amino-1,3-dihydro-indol-2-one and 2-chloro-1-[4-(4-fluoro-benzyl)-piperidin-1-yl]-ethanone (Example 197a) according to the method described in Example 206. Melting Point: 161-164° C. (diethylether)

EXAMPLE 212

1-(4-Benzyl-piperidin-1-yl)-2-phenylamino-ethanone (45 70002512)

The title compound is prepared from aniline and 2-chloro-1-(4-benzyl-piperidin-1-yl)-ethanone (Example 200a) according to the method described in Example 206. Melting Point: 107-109° C. (diethylether)

EXAMPLE 213

N-{4-[2-(4-Benzyl-piperidin-1-yl)-2-oxo-ethylamino]-phenyl}-metanesulfonamide (45 70002514)

The title compound is prepared from methanesulfonic acid-(4-amino-anilide) and 2-chloro-1-(4-benzyl-piperidin-1-yl)-ethanone (Example 200a) according to the method described in Example 206. Melting Point: 168-171° C. (diethylether)

EXAMPLE 214

4-{2-[4-(4-Fluoro-benzyl)-piperidin-1-yl]-2-oxo-ethylamino}-benzonitrile (45 70002543)

The title compound is prepared from 4-amino-benzonitrile and 2-chloro-1-[4-(4-fluoro-benzyl)-piperidin-1-yl]-ethanone (Example 197a) according to the method described in Example 206. Melting Point: 204-206° C. (diethylether)

EXAMPLE 215

3-{2-[4-(4-Fluoro-benzyl)-piperidin-1-yl]-2-oxo-ethylamino}-benzonitrile (45 70002544)

The title compound is prepared from 3-amino-benzonitrile (Fluka) and 2-chloro-1-[4-(4-fluoro-benzyl)-piperidin-1-yl]-ethanone (Example 197a) according to the method described in Example 206. Melting Point: 138-142° C. (diethylether)

EXAMPLE 216

1-[4-(4-Fluoro-benzyl)-piperidin-1-yl]-2-[4-(1H-tetrazol-5-yl)-phenylamino]-ethanone hydrochloride (45 70002608)

The title compound is prepared from 4-{2-[4-(4-fluoro-benzyl)-piperidin-1-yl]-2-oxo-ethylamino}-benzonitrile (Example 214) and azidomethyltin (Aldrich) according to the method described in Example 71b. Melting Point: 188-192° C. (diethylether)

EXAMPLE 217

1-[4-(4-Fluoro-benzyl)-piperidin-1-yl]-2-[3-(1H-tetrazol-5-yl)-phenylamino]-ethanone hydrochloride (45 70002609)

The title compound is prepared from 3-{2-[4-(4-fluoro-benzyl)-piperidin-1-yl]-2-oxo-ethylamino}-benzonitrile (Example 215) and azidomethyltin according to the method described in Example 71b. Melting Point: 173-176° C. (diethylether)

EXAMPLE 218

5-[2-[4-Benzyl)-piperidin-1-yl)-2-oxo-ethylamino]-1,3-dihydro-indol-2-one (45 70002642)

The title compound is prepared from 5-amino-1,3-dihydro-indol-2-one and 2-chloro-1-(4-benzyl-piperidin-1-yl)-ethanone (Example 200a) according to the method described in Example 206. Melting Point: 155-160° C. (diethylether)

EXAMPLE 219

1-[4-(4-Fluoro-benzyl)-piperidin-1-yl]-2-(4-methoxy-phenylamino)-ethanone (45 70002767)

The title compound is prepared from 4-methoxy-aniline (Aldrich) and 2-chloro-1-[4-(4-fluoro-benzyl)-piperidin-1-yl]-ethanone (Example 197a) according to the method described in Example 206. Melting Point: 141-143° C. (diisopropylether)

EXAMPLE 220

1-(4-Benzyl-piperidin-1-yl)-2-(4-methoxy-phenylamino)-ethanone (45 70002768)

The title compound is prepared from 4-methoxy-aniline (Aldrich) and 2-chloro-1-(4-benzyl-piperidin-1-yl)-ethanone (Example 200a) according to the method described in Example 206. Melting Point: 117-119° C. (diisopropylether)

EXAMPLE 221

1-(4-Benzyl-piperidin-1-yl)-2-(4-hydroxy-phenylamino)-ethanone (45 70002779)

The title compound is prepared from 1-(4-benzyl-piperidin-1-yl)-2-(4-methoxy-phenylamino)-ethanone (Example 220) and boron tribromide according to the method described in Example 192. Melting Point: 138-140° C. (diethylether)

EXAMPLE 222

1-[4-(4-Fluoro-benzyl)-piperidin-1-yl]-2-(4-hydroxy-phenylamino)-ethanone (45 70002795)

The title compound is prepared from 1-[4-(4-fluoro-benzyl)-piperidin-1-yl]-2-(4-methoxy-phenylamino)-ethanone (Example 219) and boron tribromide according to the method described in Example 192. Melting Point: 155-157° C. (diethylether)

EXAMPLE 223

6-{2-[4-(4-Fluoro-benzyl)-piperidin-1-yl]-2-oxo-ethylamino}-3H-benzoxazol-2-one hydrochloride (45 70002862)

The title compound is prepared from 6-{2-[4-(4-fluoro-benzyl)-piperidin-1-yl]-2-oxoethylamino}-3H-benzoxazol-2-one (Example 198) according to the method described in Example 194. Melting Point: 180-210° C. (dec.) (ethyl acetate)

EXAMPLE 224

5-[2-(4-Benzyl-piperidin-1-yl)-2-oxo-ethylamino]-1,3-dihydro-benzimidazol-2-one (45 70002223)

The title compound is prepared from 5-amino-1,3-dihydro-benzimidazol-2-one and 2-chloro-1-(4-benzyl-piperidin-1-yl)-ethanone (Example 200a) according to the method described in Example 142b. Melting Point: 237-238° C. (diethylether)

EXAMPLE 225

5-[2-(4-Benzyl-piperidin-1-yl)-2-oxo-ethylamino]-1,3-dihydro-benzoimidazol-2-one hydrochloride (45 70002907)

The title compound is prepared from 5-[2-(4-benzyl-piperidin-1-yl)-2-oxo-ethylamino]-1,3-dihydro-bezimidazol-2-one (Example 224) according to the method described in Example 194. Melting Point: 215-230° C. (dec.) (ethyl acetate)

EXAMPLE 226

5-{2-[4-(4-Fluoro-benzyl)-piperidin-1-yl]-2-oxo-ethylamino}-1,3-dihydro-benzimidazol-2-one hydrochloride (45 70002908

The title compound is prepared from 5-{2-[4-(4-fluoro-benzyl)-piperidin-1-yl]-2-oxo-ethylamino}-1,3-dihydro-benzimidazol-2-one (Example 197b) according to the method described in Example 194. Melting Point: 217-229° C. (dec.) (ethyl acetate)

EXAMPLE 227

N-(4-{2-[4-(4-Methyl-benzyl)-piperidin-1-yl]-2-oxo-ethylamino}-phenyl)-methane-sulfonamide (45 70002955)

227a) 2-Chloro-1-[4-(4-methyl-benzyl)-piperidin-1-yl]-ethanone

The title compound is prepared from 4-(4-methyl-benzyl)-piperidine and chloroacetyl chloride according to the method described in Example 142a. Melting Point: oil.

227b) N-(4-{2-[4-(4-Methyl-benzyl)-piperidin-1-yl]-2-oxo-ethylamino}-phenyl)-methane-sulfonamide The title compound is prepared from 2-chloro-1-[4-(4-methyl-benzyl)-piperidin-1-yl]-ethanone and methane-sulfonic acid-(4-aminoanilide) according to the method described in Example 206. Melting Point: 133-135° C. (diisopropylether)

EXAMPLE 228

6-{2-[4-(4-Methyl-benzyl)-piperidin-1-yl]-2-oxo-ethylamino}-3H-benzoxazol-2-one (45 70002956)

The title compound is prepared from 2-chloro-1-[4-(4-methyl-benzyl)-piperidin-1-yl]-ethanone (Example 227a) and 6-amino-3H-benzoxazol-2-one according to the method described in Example 206. Melting Point: 212-215° C. (methanol)

EXAMPLE 229

7-{2-[4-(4-Methyl-benzyl)-piperidin-1-yl]-2-oxo-ethylamino}-4H-benzo[1,4]oxazin-3-one (45 70003022)

The title compound is prepared from 2-chloro-1-[4-(4-methyl-benzyl)-piperidin-1-yl]-ethanone (Example 227a) and 7-amino-4H-benzo[1,4]oxazine-3-one according to the method described in Example 206. Melting Point: 206-208° C. (ethanol)

EXAMPLE 230

N-(4-{2-[4-(4-Chloro-benzyl)-piperidin-1-yl]-2-oxo-ethylamino}-phenyl)-methane-sulfonamide (45 70003051)

230a) 2-Chloro-1-[4-(4-chloro-benzyl)-piperidin-1-yl]-ethanone

The title compound is prepared from 4-(4-chloro-benzyl)-piperidine and chloroacetyl chloride according to the method described in Example 142a. Melting Point: 70° C. (water)

230b) N-(4-{2-[4-(4-Chloro-benzyl)-piperidin-1-yl]-2-oxo-ethylamino}-phenyl)-methane-sulfonamide The title compound is prepared from 2-chloro-1-[4-(4-chloro-benzyl)-piperidin-1-yl]-ethanone and methane-sulfonic acid-(4-aminoanilide) according to the method described in Example 206. Melting Point: 160° C. (isopropanol)

EXAMPLE 231

6-[2-(4-Benzyl-piperidin-1-yl)-2-oxo-ethylamino]-3H-benzoxazol-2-one (45 70002530)

The title compound is prepared from 6-amino-3H-benzoxazol-2-one and 2-chloro-1-(4-benzyl-piperidin-1-yl)-ethanone (Example 200a) according to the method described in Example 142b. Melting Point: 204-206° C. (diethylether)

EXAMPLE 232

6-[2-(4-Benzyl-piperidin-1-yl)-2-oxo-ethylamino]-3,4-dihydro-1H-quinolin-2-one (45 70003105)

The title compound is prepared from 6-amino-3,4-dihydro-1H-quinoline-2-one and 2-chloro-1-(4-benzyl-piperidin-1-yl)-ethanone (Example 200a) according to the method described in Example 206. Melting Point: 184-187° C. (ethanol)

EXAMPLE 233

6-{2[-4-(4-Chloro-phenoxy)-piperidin-1-yl]-2-oxo-ethylamino}-3H-benzoxazol-2-one (45 70003134)

233a) 2-Chloro-1-[4-(4-chloro-phenoxy)-piperidin-1-yl]-ethanone

The title compound is prepared from 4-(4-chloro-phenoxy)-piperidine hydrochloride (Example 30b) and chloroacetyl chloride according to the method described in Example 142a. Melting Point: oil 233b) 6-{2-[4-(4-Chloro-phenoxy)-piperidin-1-yl]-2-oxo-ethylamino}-3H-benzoxazol-2-one The title compound is prepared from 6-amino-3H-benzoxazol-2-one and 2-chloro-1-[4-(4-chloro-phenoxy)-piperidin-1-yl]-ethanone according to the method described in Example 206. Melting Point: 180-183° C. (diethylether)

EXAMPLE 234

6-{2-[4-(4-Chloro-phenoxy)-piperidin-1-yl]-2-oxo-ethylamino}-3,4-dihydro-1H-quinolin-2-one (45 70003135)

The title compound is prepared from 6-amino-3,4-dihydro-quinolin-2-one and 2-chloro-1-[4-(4-chloro-phenoxy)-piperidin-1-yl]-ethanone (Example 233a) according to the method described in Example 206. Melting Point: 248-251° C. (diethylether)

EXAMPLE 235

5-{2-[4-(4-Chloro-phenoxy)-piperidin-1-yl]-2-oxo-ethylamino}-1,3-dihydro-benzoimidazol-2-one (45 70003137)

The title compound is prepared from 5-amino-1,3-dihydro-benzimidazol-2-one and 2-chloro-1-[4-(4-chloro-phenoxy)-piperidin-1-yl]-ethanone (Example 233a) according to the method described in Example 206. Melting Point: 201-205° C. (diethylether)

EXAMPLE 236

N-(4-{2-[4-(4-Chloro-phenoxy)-piperidin-1-yl]-2-oxo-ethylamino}-phenyl-methane-sulfonamide (45 70003138)

The title compound is prepared from N-(4-aminophenyl)-methanesulfonamide and 2-chloro-1-[4-(4-chloro-phenoxy)-piperidin-1-yl]-ethanone (Example 233a) according to the method described in Example 206. Melting Point: 180-187° C. (diethylether)

EXAMPLE 237

6-{2-[4-(4-Fluoro-benzyl)-piperidin-1-yl]-2-oxo-ethylamino}-3,4-dihydro-1H-quinolin-2-one (45 70003136)

The title compound is prepared from 6-amino-3,4-dihydro-quinolin-2-one and 2-chloro-1-[4-(4-fluoro-benzyl)-piperidin-1-yl]-ethanone (Example 197a) according to the method described in Example 206. Melting Point: 197-200° C. (ethyl alcohol)

EXAMPLE 238

6-[2-(4-Benzyl-piperidin-1-yl)-1-methyl-2-oxo-ethylamino]-3H-benzoxazol-2-one (45 70002184)

238a) 1-(4-Benzyl-piperidine-1-yl)-2-bromo-propan-1-one

The title compound is prepared from 4-benzyl-piperidine and 2-bromo-propionyl chloride according to the method described in Example 142a. Melting Point: oil.

238b) 6-[2-(4-Benzyl-piperidin-1-yl)-1-methyl-2-oxo-ethylamino]-3H-benzoxazol-2-one A mixture of 1.03 g (3.33 mmol) of 1-(4-benzyl-piperidine-1-yl)-2-bromo-propan-1-one, 0.5 g (3.33 mmol) of 6-amino-3H-benzoxazol-2-one, 1.0 g (7.2 mmol) of potassium carbonate and 15 ml of dimethylformamide is refluxed for 5 hours. The reaction mixture is filtered and the filtrate is concentrated. The residue is purified by column chromatography using Kieselgel 60 adsorbent (Merck) and hexane:ethyl acetate=4:1 as eluent to yield 0.46 g (36.5%) of the title compound. Melting Point: 91° C. (hexane)

EXAMPLE 239

2-(3-Benzyl-8-aza-biciklo[3.2.1]oct-8-yl)-2-oxo-N-(2-oxo-2,3-dihydro-1H-indole-5-yl)-acetamide (45 70002703)

The title compound is prepared from N-(2-oxo-2,3-dihydro-1H-indole-5-yl)-oxalamic acid (Example 101b) and 3-benzyl-8-aza-bicyclo[3.2.1]octane [WO 20132179] according to the method described in Example 1c. Melting Point: 197.5-200° C. (diethylether)

EXAMPLE 240

2-(4-Benzyl-piperidin-1-yl)-2-oxo-N-(2-oxo-2,3-dihydro-benzoxazol-5-yl)-acetamide (45 70001830)

The title compound is prepared from 5-amino-3H-benzoxazole-2-one and (4-benzyl-piperidin-1-yl)-oxo-acetic acid (Example 5b) according to the method described in Example 2. Melting Point: 187-190° C. (water)

EXAMPLE 241

2-[4-(4-Fluoro-benzyl-piperidin-1-yl)-N-(2-hydroxyphenyl)-2-oxo-acetamide (45 70002101)

The title compound is prepared from [4-(4-fluoro-benzyl)-piperidin-1-yl)-oxo-acetic acid (Example 1b) and 2-aminophenol according to the method described in Example 1c. Melting Point: 152-156° C. (hexane)

EXAMPLE 242

2-[4-(4-Hydroxy-benzyl)-piperidin-1-yl]-2-oxo-N-(2-oxo-2,3-dihydro-benzoxazol-6-yl)-acetamide (45 70003208)

The title compound is prepared from 2-[4-(4-methoxy-benzyl)-piperidin-1-yl]-2-oxo-N-(2-oxo-2,3-dihydro-benzoxazol-6-yl)-acetamide (Example 122) according to the method described in Example 192. Melting Point:235-239° C. (diethylether)

EXAMPLE 243

7-{2-[4-(4-Chloro-phenoxy)-piperidin-1-yl]-2-oxo-ethylamino}-4H-benzo[1,4]oxazin-3-one (45 70003085)

The title compound is prepared from 2-chloro-1-[4-(4-chloro-phenoxy)-piperidin-1-yl]-ethanone (Example 233) and 7-amino-4H-benzo[1,4]oxazin-3-one according to the method described in Example 206. Melting Point:207-210° C. (methanol)

EXAMPLE 244

6-[2-Oxo-2-(4-phenoxy-piperidin-1-yl)-ethylamino]-3H-benzoxazol-2-one (45 70003156)

244a) 2-Chloro-1-(4-phenoxy-piperidin-1-yl)-ethanone

The title compound is prepared from 4-phenoxy-piperidine and chloroacetyl chloride according to the method described in Example 142a. Melting Point: oil 244b) 6-[2-Oxo-2-(4-phenoxy-piperidin-1-yl)-ethylamino]-3H-benzoxazol-2-one The title compound is prepared from 2-chloro-1-(4-phenoxy)-piperidin-1-yl]-ethanone and 6-amino-3H-benzoxazol-2-one according to the method described in Example 206. Melting Point:220-223° C. (diethylether)

EXAMPLE 245

1-[4-(4-Chloro-phenoxy)-piperidin-1-yl]-2-(4-methoxy-phenylamino)-ethanone (45 70003157)

The title compound is prepared from 2-chloro-1-[4-(4-chloro-phenoxy)-piperidin-1-yl]-ethanone (Example 233) and 4-methoxy-aniline according to the method described in Example 206. Melting Point: 127-130° C. (diethylether)

EXAMPLE 246

N-{4-[2-Oxo-2-(4-phenoxy-piperidin-1-yl)-ethylamino]-phenyl}-methanesulfonamide (45 70003206)

246a) (4-Methanesulfonylamino-phenylamino)-acetic acid ethyl ester

To a stirred solution of 5.6 g (30 mmol) of N-(4-aminophenyl)-methanesulfonamide, 6.3 ml (30 mmol) of ethyl glyoxalate solution [~50% in toluene (Fluka)], 3.4 ml (60 mmol) of acetic acid in 150 ml of dichloroethane 9.5 g (45 mmol) of sodium triacetoxyborohydride is added in small portions below 20° C., and the reaction mixture is stirred at room temperature for 10 hours. Then 200 ml of 8% sodium hydrogencarbonate solution is added to the mixture. The organic layer is separated and the water phase is extracted three times with 100 ml of chloroform. The combined organic layers are washed with 100 ml of water and dried over sodium sulfate. Concentrated, the residue is treated with diethylether and the precipitated crystals are filtered off to yield 4.48 g (55%) of the title compound. Melting Point: 135-138° C. (diethylether)

246b) (4-Methanesulfonylamino-phenylamino)-acetic acid hydrochloride

The title compound is prepared from (4-methanesulfonylamino-phenylamino)-acetic acid ethyl ester according to the method described in Example 1b. Melting Point: 218-223° C. (dec.) (water)

246c) N-{4-[2-Oxo-2-(4-phenoxy-piperidin-1-yl)-ethylamino]-phenyl}-methanesulfonamide The title compound is prepared from (4-methanesulfonylamino-phenylamino)-acetic acid hydrochloride and 4-phenoxy-piperidine according to the method described in Example 1c. Melting Point: 179-182° C. (diethylether)

EXAMPLE 247

2-[4-(4-Fluoro-benzyl)-piperidin-1-yl]-N-(2-thioxo-2,3-dihydro-1H-benzimidazol-5-yl)-acetamide (45 80002445)

247a) [4-(4-Fluoro-benzyl-piperidin-1-yl]-acetic acid ethyl ester hydrochloride

A mixture of 4.6g (20 mmol) of 4-(4-fluoro-benzyl)-piperidine hydrochloride, 4.5 ml (40 mmol) of ethyl-bromoacetate, 3.3 g (20 mmol) of potassium iodide and 200 ml of toluene is refluxed for 2 hours. The reaction mixture is concentrated. Then 150 ml of water and 150 ml of chloroform are added to the mixture. The organic layer is separated and the water phase is extracted three times with 50 ml of chloroform. The combined organic layers are washed 100 ml of water dried over sodium sulfate. Concentrated and the residue is treated with 2.5 N hydrochloric acid in ethyl acetate to yield the title compound. The crude product is used in the next step.

247b) [4-(4-Fluoro-benzyl-piperidin-1-yl]acetic acid hydrochloride

The title compound is prepared from [4-(4-fluoro-benzyl-piperidin-1-yl]-acetic acid ethyl ester hydrochloride according to the method described in Example 1b. The crude product is used in the next step.

247c) 2-[4-(4-Fluoro-benzyl)-piperidin-1-yl]-N-(2-thioxo-2,3-dihydro-1H-benzimidazol-5-yl) -acetamide The title compound is prepared from [4-(4-fluoro-benzyl-piperidin-1-yl]-acetic acid hydrochloride and 6-amino1H-benzimidazol-2-thiol according to the method described in Example 1c. Melting Point: 266-268° C. (diethylether)

EXAMPLE 248

Procedure "A"

For producing compound of formula (I), where X are —CO— group and $R^1$, $R^2$, Y, Z, U, V, n and m are as defined for the formula (I).

Step (1): Preparation of the ester compounds of formula (VIII)

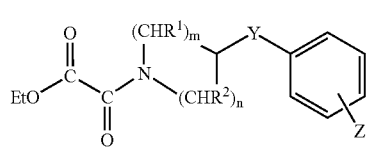

where $R^1$, $R^2$, m, n, Y and Z have the same meaning as given for formula (I). 0.1 mmol of a secondary amines of formula (III)—where $R^1$, $R^2$, m, n, Y and Z have the same meaning as given for formula (I)—are solved in 0.4 ml of $CH_2Cl_2$. Solid-supported base 2.5 (diisopropylaminomethylpolystyrene, 3 mmol/g, Fluka, cat.nr.: 38343) (83 mg) and 11.2 μL of ethyl oxalylchloride are added to the solution. The mixture is vigorously shaken for 2 hours at 40° C. The slurry is filtered off, and the resin is washed 3 times with $CH_2Cl_2$. The filtrate is concentrated in vacuum. (yield: ~100%)

Step (2): Hydrolysis of the above ester compounds to oxalic acid monoamides of formula (IX)

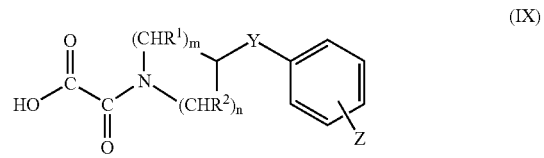

where $R^1$, $R^2$, m, n, Y and Z have the same meaning as given for formula (I).

The above obtained ester compounds of formula (VIII) are solved in 0.8 ml of ethanol and 120 mg of strongly basic ion exchange resin (DOWEX-2X8-100) in OH⁻ form is added. The mixture is vigorously shaken for 16 hours at 60° C., then the solvent is filtered off. The resin is washed 3 times with ethanol. The resin then suspended in 0.8 ml of ethyl acetate, 0.8 ml of 1.5 M HCl/ethyl acetate is added and the mixture is vigorously shaken for 3 hours at room temperature. The resin is filtered off, washed with ethyl acetate and the filtrate is concentrated in vacuum. (yield: ~100%)

Step (3): Coupling—The above obtained oxalic acid monoamides of formula (IX) are solved in 2 ml of $CH_2Cl_2$/DMF 1:1. 0.125 mmol of amine of formula (V)—where V and U areas given for formula (I)—and 0.25 mmol of 1-[3-(dimethylamino)-propyl]-3-ethylcarbodiimide (EDC) are added and the mixture is vigorously shaken for 12 hours. The mixture is diluted with 2 ml of $CH_2Cl_2$, and extracted with 4 mL of water three times. Solid supported 4-benzyloxybenzaldehyde (200 mg, 3 mmol/g, Novabiochem, Cat.nr.: 01-64-0182) is added to the organic solution and the mixture is vigorously shaken for 2 hours at 40° C. The resin is filtered off and the filtrate is concentrated to yield as final product the compounds of formula (I)—where X are —CO— group and $R^1$, $R^2$, Y, Z, U, V, n and m are as defined above.

EXAMPLE 249

Procedure "B"

For producing compound of formula (I)—where X is —$CH_2$— group and $R^1$, $R^2$, Y, Z, U, V, n and m are as defined above.

Step (1): Preparation of the ester compounds of formula (X)

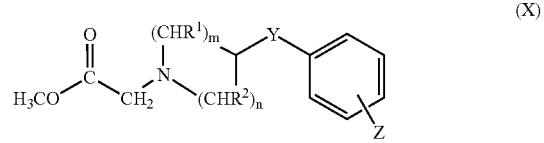

where $R^1$, $R^2$, m, n, Y and Z have the same meaning as given for formula (I).

0.1 mmol of a secondary amines of formula (III)—where $R^1$, $R^2$, m, n, Y and Z have the same meaning as given for formula (I)—and 0.04 g (0.28 mmol) of $K_2CO_3$ are solved in 0.8 ml of DMF. 12μl (0.128 mmol) of methyl bromoacetate is added and the mixture is vigorously shaken for 3 hours. 1.6 ml of diethyl ether is added to the mixture, and the precipitated salts are filtered off. The filtrate is concentrated in vacuum. (yield: ~100%)

Step (2): Hydrolysis of the above ester compounds to substituted glycines of formula (XI)

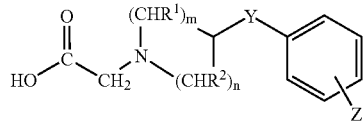

where $R^1$, $R^2$, m, n, Y and Z have the same meaning as given for formula (I).

The above obtained ester compounds of formula (X) is solved in 0.8 ml of ethanol and 120 mg of strongly basic ion exchange resin (DOWEX-2X8-100) in OH⁻ form is added. The mixture is vigorously shaken for 16 hours at 60° C., then the solvent is filtered off. The resin is washed 3 times with ethanol. The resin then suspended in 0.8 ml of ethyl acetate, 0.8 ml of 1.5 M HCl/ethyl acetate is added and the mixture is vigorously shaken for 3 hours at room temperature. The resin is filtered off, washed with ethyl acetate, and the filtrate is concentrated in vacuum. (yield: ~100%)

Step (3): Coupling—The above obtained substituted glycines of formula (XI) is solved in 2 ml of $CH_2Cl_2$/DMF 1:1. 0.125 mmol of amine of formula (V)—where V and U areas given for formula (I)—and 0.25 mmol of EDC are added and the mixture is vigorously shaken for 12 hours. The mixture is diluted with 2 ml of $CH_2Cl_2$, and extracted with 4 ml of water three times. Solid-supported 4-benzyloxybenzaldehyde (200 mg, 3 mmol/g) is added to the organic solution, and the mixture is vigorously shaken for 2 hours at 40° C. The resin is filtered off and the filtrate is concentrated to yield as final product the compounds of formula (I)—where X is —$CH_2$— group and $R^1$, $R^2$, Y, Z, U, V, n and m are as defined above.

EXAMPLE 250

Characterization and Purification Methods

Compounds of the present invention were characterized by high performance liquid chromatography coupled to mass selective detector (LC/MS) using HP 1100 Binary Gradient chromatography system with Microplate Sampler (Agilent, Waldbronn), controlled by ChemStation software. HP diode array detector was used to acquire UV spectra at 225 and 240 nm. All experiments were performed using HP MSD (Agilent, Waldbronn) single quadruple spectrometer equipped with an electrospray ionisation source to determine the structure.

The synthesized products were dissolved in 1 ml DMSO (Aldrich, Germany). 100 μl of each solution was diluted with DMSO to 1000 μl volume. Analytical chromatographic experiments were performed on Discovery RP C-16 Amide, 5 cm×4.6 mm×5 μm column from Supelco (Bellefonte, Pa.) with a flow rate of 1 ml/minute for qualification. The obtained compounds were characterized by their k' value (purity, capacity factor). k' factors are evaluated by the following formula:

$$k'=(t_R-t_0)/t_0$$

k'=capacity factor, $t_R$=retention time and $t_0$=eluent retention time.

The A eluent was water containing 0.1% trifluoroacetic acid (TFA) (Sigma, Germany), the B eluent was 95% acetonitrile (Merck, Germany) containing 0.1% TFA and 5% A eluent. Gradient elution was used, starting with 100% A eluent and processing to 100% B eluent over a period of 5 minutes.

Semipreparative separation of the compounds of the present invention—purity below 85%—was carried out using the same high performance chromatography system. The separation was performed on Discovery RP C-16 Amide, 20 cm×10 mm×5 μm semipreparative column from Supelco (Bellefonte, Pa.) with a flow rate of 3 ml/minutes. The fraction collection was based on mass selective separation. Gradient elution was used, starting with 80% A eluent and processing to 65% B eluent over a period of 35 minutes for those compounds where the capacity factor was more than 2.5. The gradient elution was changed, starting with 100% A eluent and processing to 55% B eluent in 30 minutes for those compounds where the capacity factor was less than 2.5. The collected fractions were qualified by the above detailed analytical method and the solvent was evaporated by Speed Vac (Savant, USA).

The compounds prepared as described above in procedures "A" and "B" are shown in Tables 3, 4, 5 and 6, respectively.

Compounds of formula (I) prepared by procedure "A" described in Example 248 where X is —CO— group, both of —$(CHR^1)_m$— and —$(CHR^2)_n$— are —$CH_2$—$CH_2$— groups, Y, Z, U and V are as given below:

TABLE 3

| No. | V | U | Y | Z | $MW_c$ | $MW_f$ | k' |
|---|---|---|---|---|---|---|---|
| 1. | 4-Ac—NH— | H— | —$CH_2$— | 4-F— | 397.45 | 398.5 | 3.421 |
| 2. | 4-Ac—NH— | H— | —$CH_2$— | 4-Cl— | 413.905 | 414.5 | 3.202 |
| 3. | 4-$CH_3$—$SO_2$—NH— | H— | —O— | 4-$CH_3$— | 431.507 | 432.5 | 3.349 |
| 4. | 4-Ac—NH— | H— | —O— | 4-$CH_3$— | 395.459 | 396.4 | 3.306 |
| 5. | 4-$CH_3$—$SO_2$—NH— | H— | —O— | 4-Cl— | 451.925 | 452.5 | 3.545 |
| 6. | 4-$CH_3$—$SO_2$—NH— | H— | —$CH_2$— | 4-Cl— | 449.953 | 450.4 | 3.67 |
| 7. | 4-Ac—NH— | H— | —O— | 4-Cl— | 415.877 | 416.5 | 3.518 |
| 8. | 4-$CH_3$—$SO_2$—NH— | H— | $CH_3$—N< | 4-Cl— | 464.968 | 465.5 | 2.304 |
| 9. | 4-Ac—NH— | H— | $CH_3$—N< | 4-Cl— | 428.92 | 429.5 | 2.259 |
| 10. | 4-$CH_3$—$SO_2$—NH— | H— | —$CH_2$—$CH_2$— | 4-F— | 447.525 | 448.5 | 3.57 |
| 11. | 4-Ac—NH— | H— | —$CH_2$—$CH_2$— | 4-F— | 411.477 | 412.5 | 3.555 |
| 12. | 4-$CH_3$—$SO_2$—NH— | H— | $CH_3$—N< | 4-$CH_3$— | 444.55 | 445.5 | 1.155 |
| 13. | 4-$CH_3$—$SO_2$—NH— | H— | —$CH_2$—N($CH_3$)— | H— | 444.55 | 445.4 | 1.776 |
| 14. | 4-Ac—NH— | H— | $CH_3$—N< | 4-Br— | 473.371 | 474.4 | 2.33 |
| 15. | 4-Ac—NH— | H— | $CH_3$—N< | 4-$CH_3$— | 408.502 | 409.5 | 2.169 |

Compounds of formula (I) prepared by procedure "A" described in Example 248 where X is —CO— group, both of —(CHR$^1$)$_m$— and —(CHR$^2$)$_n$— are —CH$_2$—CH$_2$— groups, U and V form together a bivalente group and Y and Z are as given below:

TABLE 4

| No. | V + U | Y | Z | MW$_c$ | MW$_f$ | k' |
|---|---|---|---|---|---|---|
| 1. | 3-4-N=N—NH— | —CH$_2$— | 4-F— | 381.411 | 382.1 | 3.387 |
| 2. | 3-4-NH—CO—NH— | —CH$_2$— | 4-CH$_3$— | 392.459 | 393.1 | 3.386 |
| 3. | 3-4-O—CH$_2$—CO—NH— | —CH$_2$— | 4-Cl— | 427.888 | 428.5 | 3.691 |
| 4. | 3-4-N=N—NH— | —CH$_2$— | 4-Cl— | 397.866 | 398.5 | 3.592 |
| 5. | 3-4-CH$_2$—CH$_2$—CO—NH— | —CH$_2$— | 4-Cl— | 425.916 | 426.6 | 3.679 |
| 6. | 3-4-CH=N—NH— | —O— | 4-CH$_3$— | 378.432 | 379.5 | 3.385 |
| 7. | 3-4-CH=CH—NH— | —O— | 4-CH$_3$— | 377.444 | 378.5 | 3.55 |
| 8. | 3-4-CH$_2$—CH$_2$—CO—NH— | —O— | 4-CH$_3$— | 407.47 | 408.5 | 3.366 |
| 9. | 3-4-CH=CH—NH— | —CH$_2$— | 4-F— | 379.435 | 380.1 | 3.645 |
| 10. | 3-4-NH—CO—O— | —CH$_2$— | 4-CH$_3$— | 393.443 | 394.5 | 3.588 |
| 11. | 3-4-CH=N—NH— | —CH$_2$— | 4-CH$_3$— | 376.46 | 377.5 | 3.631 |
| 12. | 3-4-CH=CH—NH— | —CH$_2$— | 4-CH$_3$— | 375.472 | 376.5 | 3.78 |
| 13. | 3-4-N=N—NH— | —CH$_2$— | 4-CH$_3$— | 377.448 | 378.5 | 3.533 |
| 14. | 3-4-CH$_2$—CH$_2$—CO—NH— | —CH$_2$— | 4-CH$_3$— | 405.498 | 406.5 | 3.612 |
| 15. | 3-4-NH—CO—O— | —O— | 4-Cl— | 415.833 | 416.4 | 3.48 |
| 16. | 3-4-O—CH$_2$—CO—NH— | —O— | 4-Cl— | 429.86 | 430.5 | 3.516 |
| 17. | 3-4-CH$_2$—CH$_2$—CO—NH— | —CH$_2$— | 4-F— | 409.461 | 410.6 | 3.47 |
| 18. | 3-4-CH=N—NH— | —CH$_2$— | 4-Cl— | 396.878 | 397.4 | 3.697 |
| 19. | 3-4-CH=CH—NH— | —CH$_2$— | 4-Cl— | 395.89 | 396.5 | 3.839 |
| 20. | 3-4-CH=N—NH— | —O— | 4-Cl— | 398.85 | 399.5 | 3.523 |
| 21. | 3-4-CH=CH—NH— | —O— | 4-Cl— | 397.862 | 398.3 | 3.679 |
| 22. | 3-4-N=N—NH— | —O— | 4-Cl— | 399.838 | 400.6 | 3.422 |
| 23. | 3-4-CH$_2$—CH$_2$—CO—NH— | —O— | 4-Cl— | 427.888 | 428.5 | 3.504 |
| 24. | 3-4-N=N—NH— | —O— | 4-CH$_3$— | 379.42 | 380.1 | 3.281 |
| 25. | 3-4-NH—CO—O— | CH$_3$—N< | 4-Cl— | 428.876 | 429.5 | 2.37 |
| 26. | 3-4-NH—CO—NH— | CH$_3$—N< | 4-Cl— | 427.892 | 428.6 | 2.179 |
| 27. | 3-4-N=CH—NH— | CH$_3$—N< | 4-Cl— | 411.893 | 412.5 | 1.811 |
| 28. | 3-4-O—CH$_2$—CO—NH— | CH$_3$—N< | 4-Cl— | 442.903 | 443.5 | 2.39 |
| 29. | 3-4-CH=N—NH— | CH$_3$—N< | 4-Cl— | 411.893 | 412.5 | 2.359 |
| 30. | 3-4-N=N—NH— | CH$_3$—N< | 4-Cl— | 412.881 | 413.5 | 2.295 |
| 31. | 3-4-CH$_2$—CH$_2$—CO—NH— | CH$_3$—N< | 4-Cl— | 440.931 | 441.5 | 2.382 |
| 32. | 3-4-NH—CO—CO—NH— | CH$_3$—N< | 4-Cl— | 455.902 | 456.5 | 2.161 |
| 33. | 3-4-S—CO—NH— | —CH$_2$— | 4-CH$_3$— | 409.52 | 410.5 | 3.693 |
| 34. | 3-4-S—CO—NH— | —CH$_2$— | 4-Cl— | 429.93 | 430.4 | 3.751 |
| 35. | 3-4-NH—CS—NH— | —O— | 4-CH$_3$— | 410.5 | 411.5 | 3.155 |
| 36. | 3-4-S—CO—NH— | —O— | 4-CH$_3$— | 411.49 | 412.5 | 3.462 |
| 37. | 3-4-NH—CS—NH— | CH$_3$—N< | 4-Cl— | 443.96 | 444.5 | 2.250 |
| 38. | 3-4-S—CO—NH— | CH$_3$—N< | 4-Cl— | 444.95 | 445.5 | 2.55 |
| 39. | 3-4-NH—CO—O— | —CH$_2$—CH$_2$— | 4-F— | 411.433 | 412.5 | 3.56 |
| 40. | 3-4-N=CH—NH— | —CH$_2$—CH$_2$— | 4-F— | 394.45 | 395.5 | 3.028 |
| 41. | 3-4-O—CH$_2$—CO—NH— | —CH$_2$—CH$_2$— | 4-F— | 425.46 | 426.5 | 3.629 |
| 42. | 3-4-CH=N—NH— | —CH$_2$—CH$_2$— | 4-F— | 394.45 | 395.5 | 3.609 |
| 43. | 3-4-N=N—NH— | —CH$_2$—CH$_2$— | 4-F— | 395.438 | 396.5 | 3.517 |
| 44. | 3-4-CH$_2$—CH$_2$—CO—NH— | —CH$_2$—CH$_2$— | 4-F— | 423.488 | 424.5 | 3.591 |
| 45. | 3-4-NH—CS—NH— | —CH$_2$—CH$_2$— | 4-F— | 426.52 | 427.5 | 3.448 |
| 46. | 3-4-S—CO—NH— | —CH$_2$—CH$_2$— | 4-F— | 427.51 | 428.5 | 3.721 |
| 47. | 3-4-NH—CO—O— | CH$_3$—N< | 4-CH$_3$— | 408.458 | 409.5 | 2.244 |
| 48. | 3-4-N=CH—NH— | CH$_3$—N< | 4-CH$_3$— | 391.475 | 392.5 | 1.711 |
| 49. | 3-4-O—CH$_2$—CO—NH— | CH$_3$—N< | 4-CH$_3$— | 422.485 | 423.5 | 2.264 |
| 50. | 3-4-CH=N—NH— | CH$_3$—N< | 4-CH$_3$— | 391.475 | 392.5 | 2.237 |
| 51. | 3-4-N=N—NH— | CH$_3$—N< | 4-CH$_3$— | 392.463 | 393.5 | 2.165 |
| 52. | 3-4-NH—C(CH$_3$)=N— | CH$_3$—N< | 4-CH$_3$— | 405.502 | 406.5 | 1.813 |
| 53. | 3-4-CH$_2$—CH$_2$—CO—NH— | CH$_3$—N< | 4-CH$_3$— | 420.513 | 421.6 | 2.265 |
| 54. | 3-4-NH—CS—NH— | CH$_3$—N< | 4-CH$_3$— | 423.55 | 424.5 | 2.149 |
| 55. | 3-4-S—CO—NH— | CH$_3$—N< | 4-CH$_3$— | 424.53 | 425.5 | 2.439 |
| 56. | 3-4-NH—CS—NH— | —CH$_2$— | 4-F— | 412.5 | 413.5 | 3.376 |
| 57. | 3-4-S—CO—NH— | —CH$_2$— | 4-F— | 413.5 | 414.5 | 3.562 |
| 58. | 3-4-NH—CS—NH— | —CH$_2$— | 4-Cl— | 428.95 | 429.4 | 3.477 |
| 59. | 3-4-S—CO—NH— | —O— | 4-Cl— | 431.91 | 432.4 | 3.582 |
| 60. | 3-4-CH=CH—NH— | —CH$_2$—CH$_2$— | 4-F— | 393.462 | 394.5 | 3.74 |
| 61. | 3-4-CH=CH—NH— | CH$_3$—N< | 4-Cl— | 410.905 | 411.5 | 2.502 |
| 62. | 3-4-NH—CO—O— | —CH$_2$—N(CH$_3$)— | H— | 408.458 | 409.4 | 1.882 |
| 63. | 3-4-O—CH$_2$—CO—NH— | —CH$_2$—N(CH$_3$)— | H— | 422.485 | 423.5 | 1.925 |
| 64. | 3-4-CH=CH—NH— | —CH$_2$—N(CH$_3$)— | H— | 390.487 | 391.4 | 1.945 |
| 65. | 3-4-NH—CS—NH— | —CH$_2$—N(CH$_3$)— | H— | 423.535 | 424.5 | 1.834 |
| 66. | 3-4-S—CO—NH— | —CH$_2$—N(CH$_3$)— | H— | 424.519 | 425.5 | 2.108 |
| 67. | 3-4-NH—CO—O— | CH$_3$—N< | 4-Br— | 473.327 | 474.3 | 2.404 |
| 68. | 3-4-NH—CO—NH— | CH$_3$—N< | 4-Br— | 472.343 | 473.4 | 2.218 |
| 69. | 3-4-N=CH—NH— | CH$_3$—N< | 4-Br— | 456.344 | 457.4 | 1.839 |
| 70. | 3-4-O—CH$_2$—CO—NH— | CH$_3$—N< | 4-Br— | 487.354 | 488.4 | 2.428 |

TABLE 4-continued

| No. | V + U | Y | Z | MW$_c$ | MW$_f$ | k' |
|---|---|---|---|---|---|---|
| 71. | 3-4-CH=CH—NH— | CH$_3$—N< | 4-Br— | 455.356 | 456.4 | 2.539 |
| 72. | 3-4-CH$_2$—CH$_2$—CO—NH— | CH$_3$—N< | 4-Br— | 485.382 | 486.4 | 2.429 |

Compounds of formula (I) prepared by procedure "B" described in Example 249 where X is —CH$_2$— group, both of —(CHR$^1$)$_m$— and —(CHR$^2$)$_n$— are —CH$_2$—CH$_2$— groups Y, Z, U and V are as given below:

TABLE 5

| No. | V | U | Y | Z | MW$_c$ | MW$_f$ | k' |
|---|---|---|---|---|---|---|---|
| 1. | 4-Ac—NH— | H— | —CH$_2$— | H— | 365.477 | 366.5 | 2.272 |
| 2. | 4-CH$_3$—SO$_2$—NH— | H— | —CH$_2$— | 4-F— | 419.515 | 420.5 | 2.335 |
| 3. | 4-Ac—NH— | H— | —CH$_2$— | 4-F— | 383.467 | 384.5 | 2.366 |
| 4. | 4-HO— | H— | —CH$_2$— | 4-F— | 342.413 | 343.5 | 2.100 |
| 5. | 4-Ac—NH— | H— | —CH$_2$— | 4-Cl— | 399.922 | 400.5 | 2.644 |
| 6. | 4-CH$_3$—SO$_2$—NH— | H— | —CH$_2$— | 4-Cl— | 435.97 | 436.5 | 2.649 |
| 7. | 4-HO— | H— | —CH$_2$— | 4-Cl— | 358.869 | 359.4 | 2.48 |
| 8. | 4-CH$_3$—SO$_2$—NH— | H— | —O— | 4-Cl— | 437.942 | 438.4 | 2.455 |
| 9. | 4-Ac—NH— | H— | —O— | 4-Cl— | 401.894 | 402.5 | 3.35 |
| 10. | 4-HO— | H— | —O— | 4-Cl— | 360.841 | 361.4 | 2.264 |
| 11. | 4-Ac—NH— | H— | —O— | 4-CH$_3$— | 381.476 | 382.5 | 2.329 |
| 12. | 4-HO— | H— | —O— | 4-CH$_3$— | 340.423 | 341.4 | 2.112 |
| 13 | 4-CH$_3$—SO$_2$—NH— | H— | —CH$_2$— | 4-CH$_3$— | 415.552 | 416.6 | 2.539 |
| 14 | 4-Ac—NH— | H— | —CH$_2$— | 4-CH$_3$— | 379.504 | 380.5 | 2.527 |
| 15. | 4-HO— | H— | —CH$_2$— | 4-CH$_3$— | 338.451 | 339.5 | 2.33 |
| 16. | 4-HO— | H— | CH$_3$—N< | 4-Cl— | 373.884 | 374.4 | 1.369 |
| 17. | 4-Ac—NH— | H— | CH$_3$—N< | 4-Cl— | 414.937 | 415.4 | 1.785 |
| 18. | 4-CH$_3$—SO$_2$—NH— | H— | CH$_3$—N< | 4-Cl— | 450.985 | 451.5 | 1.704 |
| 19. | 4-CH$_3$—SO$_2$—NH— | H— | —CH$_2$—CH$_2$— | 4-F— | 433.542 | 434.3 | 2.504 |
| 20. | 4-Ac—NH— | H— | —CH$_2$—CH$_2$— | 4-F— | 397.494 | 398.2 | 2.53 |
| 21. | 4-HO— | H— | —CH$_2$—CH$_2$— | 4-F— | 356.441 | 357.2 | 2.325 |
| 22. | 4-CH$_3$—SO$_2$—NH— | H— | CH$_3$—N< | 4-CH$_3$— | 430.567 | 431.3 | 1.332 |
| 23. | 4-Ac—NH— | H— | CH$_3$—N< | 4-CH$_3$— | 394.519 | 395.3 | 1.433 |
| 24. | 4-Ac—NH— | H— | CH$_3$—N< | 4-Br— | 459.388 | 460.2 | 1.864 |
| 25. | 4-HO— | H— | CH$_3$—N< | 4-Br— | 418.335 | 419.2 | 1.461 |
| 26. | 4-CH$_3$—SO$_2$—NH— | H— | CH$_3$—N< | 4-Br— | 495.436 | 496.3 | 1.793 |
| 27. | 4-HO— | H— | CH$_3$—N< | 4-CH$_3$— | 353.466 | 354.3 | 1.027 |

Compounds of formula (I) prepared by procedure "B" described in Example 249 where X is —CH$_2$— group, both of —(CHR$^1$)$_m$— and —(CHR$^2$)$_n$— are —CH$_2$—CH$_2$— groups, U and V form together a bivalente group and Y and Z are as given below:

TABLE 6

| No. | V + U | Y | Z | MW$_c$ | MW$_f$ | k' |
|---|---|---|---|---|---|---|
| 1. | 3-4-NH—CO—O— | —CH$_2$— | H— | 365.433 | 366.4 | 2.297 |
| 2. | 3-4-N=CH—NH— | —CH$_2$— | H— | 348.45 | 349.4 | 1.708 |
| 3. | 3-4-NH—N=CH— | —CH$_2$— | H— | 348.45 | 349.4 | 2.392 |
| 4. | 3-4-CH=N—NH— | —CH$_2$— | H— | 348.45 | 349.4 | 2.36 |
| 5. | 3-4-CH=CH—NH— | —CH$_2$— | H— | 347.462 | 348.4 | 2.449 |
| 6. | 3-4-N=N—NH— | —CH$_2$— | H— | 349.438 | 350.4 | 2.286 |
| 7. | 3-4-S—C(SH)=N— | —CH$_2$— | H— | 397.555 | 398.4 | 2.729 |
| 8. | 3-4-CH=C(CH$_3$)—NH— | —CH$_2$— | H— | 361.489 | 362.5 | 2.656 |
| 9. | 3-4-NH—C(CH$_3$)=N— | —CH$_2$— | H— | 362.477 | 363.5 | 1.849 |
| 10. | 3-4-CH$_2$—CH$_2$—CO—NH— | —CH$_2$— | H— | 377.488 | 378.5 | 2.376 |
| 11. | 3-4-S—CO—NH— | —CH$_2$— | H— | 381.494 | 382.5 | 2.516 |
| 12. | 3-4-NH—CO—O— | —CH$_2$— | 4-F— | 383.423 | 384.4 | 2.408 |
| 13. | 3-4-N=CH—NH— | —CH$_2$— | 4-F— | 366.44 | 367.5 | 1.808 |
| 14. | 3-4-O—CH$_2$—CO—NH— | —CH$_2$— | 4-F— | 397.45 | 398.5 | 2.445 |
| 15. | 3-4-NH—N=CH— | —CH$_2$— | 4-F— | 366.44 | 367.5 | 2.483 |
| 16. | 3-4-CH=N—NH— | —CH$_2$— | 4-F— | 366.44 | 367.5 | 2.446 |
| 17. | 3-4-CH=CH—NH— | —CH$_2$— | 4-F— | 365.452 | 366.5 | 2.558 |
| 18. | 3-4-N=N—NH— | —CH$_2$— | 4-F— | 367.428 | 368.5 | 2.381 |

TABLE 6-continued

| No. | V + U | Y | Z | MW$_c$ | MW$_f$ | k' |
|---|---|---|---|---|---|---|
| 19. | 3-4-S—C(SH)=N— | —CH$_2$— | 4-F— | 415.545 | 416.5 | 2.788 |
| 20. | 3-4-CH=C(CH$_3$)—NH— | —CH$_2$— | 4-F— | 379.479 | 380.5 | 2.743 |
| 21. | 3-4-NH—C(CH$_3$)=N— | —CH$_2$— | 4-F— | 380.467 | 381.5 | 1.942 |
| 22. | 3-4-CH$_2$—CH$_2$—CO—NH— | —CH$_2$— | 4-F— | 395.478 | 396.5 | 2.455 |
| 23. | 3-4-NH—CS—NH— | —CH$_2$— | 4-F— | 398.5 | 399.5 | 2.349 |
| 24. | 3-4-S—CO—NH— | —CH$_2$— | 4-F— | 399.484 | 400.4 | 1.59 |
| 25. | 3-4-N=CH—NH— | —CH$_2$— | 4-CH$_3$— | 362.477 | 363.5 | 2.002 |
| 26. | 3-4-O—CO—NH— | —CH$_2$— | 4-Cl— | 399.878 | 400.4 | 2.687 |
| 27. | 3-4-NH—CO—O— | —CH$_2$— | 4-Cl— | 399.878 | 400.4 | 2.669 |
| 28. | 3-4-CH=CH—NH— | —CH$_2$— | 4-Cl— | 381.907 | 382.5 | 2.827 |
| 29. | 3-4-S—C(SH)=N— | —CH$_2$— | 4-Cl— | 432.00 | 432.4 | 3.006 |
| 30. | 3-4-CH=C(CH$_3$)—NH— | —CH$_2$— | 4-Cl— | 395.934 | 396.5 | 2.972 |
| 31. | 3-4-NH—C(CH$_3$)=N— | —CH$_2$— | 4-Cl— | 396.922 | 397.5 | 2.222 |
| 32. | 3-4-CH$_2$—CH$_2$—CO—NH— | —CH$_2$— | 4-Cl— | 411.933 | 412.5 | 2.727 |
| 33. | 3-4-CH$_2$—CO—NH— | —CH$_2$— | 4-Cl— | 397.906 | 398.5 | 2.616 |
| 34. | 3-4-N=CH—NH— | —CH$_2$— | 4-Cl— | 382.895 | 383.5 | 2.154 |
| 35. | 3-4-O—CH$_2$—CO—NH— | —CH$_2$— | 4-Cl— | 413.905 | 414.5 | 2.724 |
| 36. | 3-4-NH—CS—NH— | —CH$_2$— | 4-Cl— | 414.955 | 415.4 | 2.616 |
| 37. | 3-4-S—CO—NH— | —CH$_2$— | 4-Cl— | 415.939 | 416.4 | 2.105 |
| 38. | 3-4-O—CO—NH— | —O— | 4-Cl— | 401.85 | 402.4 | 2.513 |
| 39. | 3-4-NH—CO—O— | —O— | 4-Cl— | 401.85 | 402.4 | 2.481 |
| 40. | 3-4-N=CH—NH— | —O— | 4-Cl— | 384.867 | 385.5 | 1.93 |
| 41. | 3-4-O—CH$_2$—CO—NH— | —O— | 4-Cl— | 415.877 | 416.4 | 2.54 |
| 42. | 3-4-NH—N=CH— | —O— | 4-Cl— | 384.867 | 385.4 | 2.575 |
| 43. | 3-4-CH=N—NH— | —O— | 4-Cl— | 384.867 | 385.4 | 2.544 |
| 44. | 3-4-CH=CH—NH— | —O— | 4-Cl— | 383.879 | 384.4 | 2.646 |
| 45. | 3-4-CH=C(CH$_3$)—NH— | —O— | 4-Cl— | 397.906 | 398.5 | 2.807 |
| 46. | 3-4-NH—C(CH$_3$)=N— | —O— | 4-Cl— | 398.894 | 399.4 | 2.058 |
| 47. | 3-4-CH$_2$—CH$_2$—CO—NH— | —O— | 4-Cl— | 413.905 | 414.5 | 2.56 |
| 48. | 3-4-S—CO—NH— | —O— | 4-Cl— | 417.911 | 418.4 | 2.677 |
| 49. | 3-4-O—CO—NH— | —O— | 4-CH$_3$— | 381.432 | 382.4 | 2.391 |
| 50. | 3-4-NH—CO—O— | —O— | 4-CH$_3$— | 381.432 | 382.5 | 2.374 |
| 51. | 3-4-NH—CO—NH— | —O— | 4-CH$_3$— | 380.448 | 381.5 | 2.255 |
| 52. | 3-4-CH$_2$—CO—NH— | —O— | 4-CH$_3$— | 379.46 | 380.5 | 2.296 |
| 53. | 3-4-N=CH—NH— | —O— | 4-CH$_3$— | 364.449 | 365.5 | 1.841 |
| 54. | 3-4-O—CH$_2$—CO—NH— | —O— | 4-CH$_3$— | 395.459 | 396.5 | 2.419 |
| 55. | 3-4-NH—N=CH— | —O— | 4-CH$_3$— | 364.449 | 365.5 | 2.466 |
| 56. | 3-4-CH=N—NH— | —O— | 4-CH$_3$— | 364.449 | 365.5 | 2.418 |
| 57. | 3-4-S—C(SH)=N— | —O— | 4-CH$_3$— | 413.554 | 414.4 | 2.74 |
| 58. | 3-4-CH=C(CH$_3$)—NH— | —O— | 4-CH$_3$— | 377.488 | 378.5 | 2.702 |
| 59. | 3-4-NH—C(CH$_3$)=N— | —O— | 4-CH$_3$— | 378.476 | 380.5 | 1.946 |
| 60. | 3-4-CH$_2$—CH$_2$—CO—NH— | —O— | 4-CH$_3$— | 393.487 | 394.5 | 2.438 |
| 61. | 3-4-NH—CS—NH— | —O— | 4-CH$_3$— | 396.509 | 397.5 | 2.327 |
| 62. | 3-4-O—CO—NH— | —CH$_2$— | 4-CH$_3$— | 379.46 | 380.5 | 2.574 |
| 63. | 3-4-NH—CO—O— | —CH$_2$— | 4-CH$_3$— | 379.46 | 380.5 | 2.544 |
| 64. | 3-4-NH—CO—NH— | —CH$_2$— | 4-CH$_3$— | 378.476 | 379.5 | 2.433 |
| 65. | 3-4-CH$_2$—CO—NH— | —CH$_2$— | 4-CH$_3$— | 377.488 | 378.5 | 2.486 |
| 66. | 3-4-O—CH$_2$—CO—NH— | —CH$_2$— | 4-CH$_3$— | 393.487 | 394.5 | 2.592 |
| 67. | 3-4-NH—N=CH— | —CH$_2$— | 4-CH$_3$— | 362.477 | 363.5 | 2.645 |
| 68. | 3-4-CH=N—NH— | —CH$_2$— | 4-CH$_3$— | 362.477 | 363.5 | 2.618 |
| 69. | 3-4-CH=CH—NH— | —CH$_2$— | 4-CH$_3$— | 361.489 | 362.5 | 2.735 |
| 70. | 3-4-S—C(SH)=N— | —CH$_2$— | 4-CH$_3$— | 411.582 | 412.5 | 2.919 |
| 71. | 3-4-CH=C(CH$_3$)—NH— | —CH$_2$— | 4-CH$_3$— | 375.516 | 376.5 | 2.885 |
| 72. | 3-4-NH—C(CH$_3$)=N— | —CH$_2$— | 4-CH$_3$— | 376.504 | 377.4 | 2.100 |
| 73. | 3-4-CH$_2$—CH$_2$—CO—NH— | —CH$_2$— | 4-CH$_3$— | 391.515 | 392.5 | 2.612 |
| 74. | 3-4-NH—CS—NH— | —CH$_2$— | 4-CH$_3$— | 394.537 | 395.5 | 2.500 |
| 75. | 3-4-S—CO—NH— | —CH$_2$— | 4-CH$_3$— | 395.521 | 396.5 | 2.733 |
| 76. | 3-4-N=CH—NH— | CH$_3$—N< | 4-Cl— | 397.91 | 398.5 | 1.296 |
| 77. | 3-4-O—CH$_2$—CO—NH— | CH$_3$—N< | 4-Cl— | 428.92 | 429.5 | 1.896 |
| 78. | 3-4-S—C(SH)=N— | CH$_3$—N< | 4-Cl— | 447.015 | 447.5 | 2.285 |
| 79. | 3-4-NH—C(CH$_3$)=N— | CH$_3$—N< | 4-Cl— | 411.937 | 412.4 | 1.455 |
| 80. | 3-4-CH$_2$—CH$_2$—CO—NH— | CH$_3$—N< | 4-Cl— | 426.948 | 427.4 | 1.937 |
| 81. | 3-4-CH$_2$—CO—NH— | —O— | 4-Cl— | 399.878 | 400.4 | 2.43 |
| 82. | 3-4-O—CO—NH— | CH$_3$—N< | 4-Cl— | 414.893 | 415.5 | 1.827 |
| 83. | 3-4-CH=N—NH— | CH$_3$—N< | 4-Cl— | 397.91 | 398.5 | 1.853 |
| 84. | 3-4-NH—N=CH— | CH$_3$—N< | 4-Cl— | 397.91 | 398.5 | 1.932 |
| 85. | 3-4-CH=CH—NH— | CH$_3$—N< | 4-Cl— | 396.922 | 397.5 | 1.862 |
| 86. | 3-4-CH=C(CH$_3$)—NH— | CH$_3$—N< | 4-Cl— | 410.949 | 411.4 | 2.130 |
| 87. | 3-4-S—CO—NH— | CH$_3$—N< | 4-Cl— | 430.954 | 431.4 | 2.072 |
| 88. | 3-4-O—CO—NH— | —CH$_2$—CH$_2$— | 4-F— | 397.45 | 398.3 | 2.558 |
| 89. | 3-4-NH—CO—O— | —CH$_2$—CH$_2$— | 4-F— | 397.45 | 398.3 | 2.525 |
| 90. | 3-4-CH$_2$—CO—NH— | —CH$_2$—CH$_2$— | 4-F— | 395.478 | 396.2 | 2.481 |
| 91. | 3-4-N=CH—NH— | —CH$_2$—CH$_2$— | 4-F— | 380.467 | 381.2 | 1.988 |
| 92. | 3-4-O—CH$_2$—CO—NH— | —CH$_2$—CH$_2$— | 4-F— | 411.477 | 412.2 | 2.585 |
| 93. | 3-4-NH—N=CH— | —CH$_2$—CH$_2$— | 4-F— | 380.467 | 381.2 | 2.623 |
| 94. | 3-4-CH=N—NH— | —CH$_2$—CH$_2$— | 4-F— | 380.467 | 381.2 | 2.601 |
| 95. | 3-4-CH=CH—NH— | —CH$_2$—CH$_2$— | 4-F— | 379.479 | 380.2 | 2.696 |

TABLE 6-continued

| No. | V + U | Y | Z | $MW_c$ | $MW_f$ | k' |
|---|---|---|---|---|---|---|
| 96. | 3-4-S—C(SH)=N— | —CH$_2$—CH$_2$— | 4-F— | 429.572 | 430.4 | 2.881 |
| 97. | 3-4-CH=C(CH$_3$)—NH— | —CH$_2$—CH$_2$— | 4-F— | 393.506 | 394.2 | 2.851 |
| 98. | 3-4-NH—C(CH$_3$)=N— | —CH$_2$—CH$_2$— | 4-F— | 394.494 | 395.2 | 2.085 |
| 99. | 3-4-CH$_2$—CH$_2$—CO—NH— | —CH$_2$—CH$_2$— | 4-F— | 409.505 | 410.2 | 2.602 |
| 100. | 3-4-NH—CS—NH— | —CH$_2$—CH$_2$— | 4-F— | 412.527 | 413.2 | 2.475 |
| 101. | 3-4-S—CO—NH— | —CH$_2$—CH$_2$— | 4-F— | 413.511 | 414.3 | 2.716 |
| 102. | 3-4-O—CO—NH— | CH$_3$—N< | 4-CH$_3$— | 394.475 | 395.2 | 1.467 |
| 103. | 3-4-NH—CO—O— | CH$_3$—N< | 4-CH$_3$— | 394.475 | 395.2 | 1.48 |
| 104 | 3-4-NH—CO—NH— | CH$_3$—N< | 4-CH$_3$— | 393.491 | 394.2 | 1.423 |
| 105. | 3-4-CH$_2$—CO—NH— | CH$_3$—N< | 4-CH$_3$— | 392.503 | 393.3 | 1.444 |
| 106. | 3-4-N=CH—NH— | CH$_3$—N< | 4-CH$_3$— | 377.492 | 378.2 | 0.966 |
| 107. | 3-4-O—CH$_2$—CO—NH— | CH$_3$—N< | 4-CH$_3$— | 408.502 | 409.3 | 1.544 |
| 108. | 3-4-CH=CH—NH— | CH$_3$—N< | 4-CH$_3$— | 376.504 | 377.2 | 1.453 |
| 109. | 3-4-S—C(SH)=N— | CH$_3$—N< | 4-CH$_3$— | 426.597 | 427.3 | 1.896 |
| 110. | 3-4-CH$_2$—CH$_2$—CO—NH— | CH$_3$—N< | 4-CH$_3$— | 406.53 | 407.3 | 1.574 |
| 111. | 3-4-NH—CS—NH— | CH$_3$—N< | 4-CH$_3$— | 409.552 | 410.3 | 1.455 |
| 112. | 3-4-S—CO—NH— | CH$_3$—N< | 4-CH$_3$— | 410.536 | 410.3 | 1.682 |
| 113. | 3-4-CH=C(CH$_3$)—NH— | CH$_3$—N< | 4-Br— | 455.4 | 456.2 | 2.211 |
| 114. | 3-4-NH—C(CH$_3$)=N— | CH$_3$—N< | 4-Br— | 456.388 | 457.2 | 1.522 |
| 115. | 3-4-CH$_2$—CH$_2$—CO—NH— | CH$_3$—N< | 4-Br— | 471.399 | 472.8 | 2.001 |
| 116. | 3-4-S—CO—NH— | CH$_3$—N< | 4-Br— | 475.405 | 476.2 | 2.159 |
| 117. | 3-4-CH=C(CH$_3$)—NH— | CH$_3$—N< | 4-CH$_3$— | 390.531 | 391.3 | 1.708 |
| 118. | 3-4-CH=N—NH— | CH$_3$—N< | 4-CH$_3$— | 377.492 | 378.3 | 1.495 |
| 119. | 3-4-NH—N=CH— | CH$_3$—N< | 4-CH$_3$— | 377.492 | 378.3 | 1.572 |
| 120. | 3-4-O—CO—NH— | CH$_3$—N< | 4-Br— | 459.344 | 460.2 | 1.913 |
| 121. | 3-4-CH$_2$—CO—NH— | CH$_3$—N< | 4-Br— | 457.372 | 458.2 | 1.839 |
| 122. | 3-4-N=CH—NH— | CH$_3$—N< | 4-Br— | 442.361 | 443.2 | 1.39 |
| 123. | 3-4-O—CH$_2$—CO—NH— | CH$_3$—N< | 4-Br— | 473.371 | 474.2 | 1.986 |
| 124. | 3-4-NH—N=CH— | CH$_3$—N< | 4-Br— | 442.361 | 443.2 | 2.023 |
| 125. | 3-4-CH=N—NH— | CH$_3$—N< | 4-Br— | 442.361 | 443.2 | 1.949 |
| 126. | 3-4-CH=CH—NH— | CH$_3$—N< | 4-Br— | 441.373 | 442.2 | 1.953 |
| 127. | 3-4-S—C(SH)=N— | CH$_3$—N< | 4-Br— | 491.466 | 492.2 | 2.371 |
| 128. | 3-4-NH—CS—NH— | CH$_3$—N< | 4-Br— | 474.421 | 475.2 | 1.897 |
| 129. | 3-4-NH—C(CH$_3$)=N— | CH$_3$—N< | 4-CH$_3$— | 391.519 | 392.3 | 1.151 |
| 130. | 3-4-NH—CO—O— | CH$_3$—N< | 4-Br— | 459.344 | 460.2 | 1.908 |

EXAMPLE 251

Preparation of Pharmaceutical Compositions a) Tablets:

0.01-50% of active ingredient of formula I, 15-50% of lactose, 15-50% of potato starch, 5-15% of polyvinyl pyrrolidone, 1-5% of talc, 0.01-3% of magnesium stearate, 1-3% of colloid silicon dioxide and 2-7% of ultraamylopectin are mixed, then are granulated by wet granulation and pressed to tablets.

b) Dragées, Filmcoated Tablets

The tablets made according to the method described above are coated by a layer consisting of entero- or gastrosolvent film, or of sugar and talc. The dragées are polished by a mixture of beeswax and carnuba wax.

c) Capsules 0.01-50% of active ingredient of formula I, 1-5% of sodium lauryl sulfate, 15-50% of starch, 15-50% of lactose, 1-3% of colloid silicon dioxide and 0.01-3% of magnesium stearate are thoroughly mixed, the mixture is passed through a sieve and filled in hard gelatin capsules.

d) Suspensions

Ingredients: 0.01-15% of active ingredient of formula I, 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrilic acid), 0.1-5% of 96% ethanol, 0.1-1% of flavoring agent, 20-70% of sorbitol (70% aqueous solution) and 30-50% of distilled water.

To solution of nipagin and citric acid in 20 ml of distilled water, carbopol is added in small portions under vigorous stirring, and the solution is left to stand for 10-12 h. Then the sodium hydroxide in 1 ml of distilled water, the aqueous solution of sorbitol and finally the ethanolic raspberry flavor are added with stirring. To this carrier the active ingredient is added in small portions and suspended with an immersing homogenizator. Finally the suspension is filled up to the desired final volume with distilled water and the suspension syrup is passed through a colloid milling equipment.

e) Suppositories

For each suppository 0.01-15% of active ingredient of formula I and 1-20% of lactose are thoroughly mixed, then 50-95% of adeps pro suppositary (for example Witepsol 4) is melted, cooled to 35° C. and the mixture of active ingredient and lactose is mixed in it with homogenizator. The obtained mixture is mould in cooled forms.

f) Lyophilized Powder Ampoule Compositions

A 5% solution of mannitol or lactose is made with bidistilled water for injection use, and the solution is filtered so as to have sterile solution. A 0.01-5% solution of the active ingredient of formula I is also made with bidistilled water for injection use, and this solution is filtered so as to have sterile solution. These two solutions are mixed under aseptic conditions, filled in 1 ml portions into ampoules, the content of the ampoules is lyophilized, and the ampoules are sealed under nitrogen. The contents of the ampoules are dissolved in sterile water or 0.9% (physiological) sterile aqueous sodium chloride solution before administration.

It should be understood that the term "comprises/comprising" when used in this specification, is taken to specify the presence of stated features, integers, steps or components; but does not preclude the presence or addition of one or more other features, integers, steps, components or groups thereof.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives failing within the spirit and scope of the invention as defined by the appended claims.

What is claimed is:

1. A compound comprising a structure of formula (I):

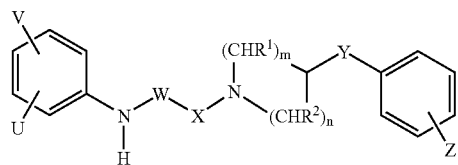

wherein:
V and U:
  together form a group that contains one or more heteroatoms, and that taken together with one or more:
    (a) hydrogen atoms;
    (b) carbon atoms;
    (c) —CH= groups;
    (d) —CH$_2$— groups; or
    (e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4-oxazine, oxazole, oxazolidine, oxo-oxazolidine, thioxo-oxazolidine or 3-oxo-1,4-oxazine;
  W: —CO—, —CH$_2$— or —CH$_2$—(C$_1$-C4 alkyl)-;
  X: —CO—;
  Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
  Z: is hydrogen, halogen, nitro, amino, C$_1$-C$_4$ alkyl, C$_1$-C$_4$ alkoxy, cyano, trifluoromethyl, hydroxyl or carboxyl;
  R$^1$ and R$^2$: are hydrogen, or together form a C$_1$-C$_3$ bridge; and
  n and m: independently are 0-3, wherein n and m cannot each be 0, and wherein m+n=4;
or an optical antipode, racemate or pharmaceutically-acceptable salt thereof.

2. The compound of claim 1 wherein —(CHR$^1$)$_m$ and —(CHR$^2$)$_n$ are each —CH$_2$—CH$_2$—.

3. The compound of claim 2 wherein W is —CH$_2$—.

4. The compound of claim 2 wherein W is —CO—.

5. The compound of claim 1 wherein the compound is:
2-[4-(4-fluoro-benzyl)-piperidin-1-yl]-2-oxo-N-(2-oxo-2,3-dihydro-1H-indol-5-yl)-acetamide;
2-[4-(4-fluoro-benzyl)-piperidin-1-yl]-2-oxo-N-(2-oxo-2,3-dihydro-benzoxazol-6-yl)-acetamide;
2-[4-(4-fluoro-benzyl)-piperidin-1-yl]-2-oxo-N-(2-oxo-2,3-dihydro-1H-benzimidazol-5-yl) acetamide;
2-(4-benzyl-piperidin-1-yl)-2-oxo-N-(2-oxo-2,3-dihydro-1H-indol-5-yl)-acetamide;
2-(4-benzyl-piperidin-1-yl)-2-oxo-N-(2-oxo-2,3-dihydro-1H-benzimidazol-5-yl)-acetamide;
2-(4-benzyl-piperidin-1-yl)-2-oxo-N-(2-oxo-2,3-dihydro-benzoxazol-6-yl)-acetamide;
5-{2-[4-(4-fluoro-benzyl)-piperidin-1-yl]-2-oxo-ethylamino}-1,3-dihydro-benzoimidazol-2-one;
6-{2-[4-(4-fluoro-benzyl)-piperidin-1-yl]-2-oxo-ethylamino}-3H-benzoxazol-2-one;
2-[4-(4-methylbenzyl)-piperidin-1-yl]-2-oxo-N-(3-oxo-3,4-dihydro-2H benzo[1,4]oxazin-7-yl) acetamide;
2-[4-[4-methyl-benzyl)-piperidin-1-yl]-2-oxo-N-(2-oxo-2,3-dihydro-1H-indol-5-yl)-acetamide;
2-[4-(4-chloro-phenoxy)-piperidin-1-yl]-2-oxo-N-(2-oxo-2,3-dihydro-1H-benzimidazol-5-yl) acetamide;
2-[4-(4-chloro-phenoxy)-piperidin-1-yl]-2-oxo-N-(2-oxo-2,3-dihydro-benzoxazol-6-yl)acetamide;
2-[4-(4-chloro-benzyl)-piperidin-1-yl]-2-oxo-N-(2-oxo-2,3-dihydro-benzoxazol-6-yl)-acetamide;
2-[4-(4-chloro-benzyl)-piperidin-1-yl]-2-oxo-N-(2-oxo-2,3-dihydro-1H-benzimidazol-5-yl) acetamide;
2-oxo-N-(2-oxo-2,3-dihydro-benzoxazol-6-yl)-2-(4-p-tolyloxy-piperidin-1-yl)-acetamide;
2-oxo-N-(2-oxo-2,3-dihydro-1H-benzimidazol-6-yl)-2-(4-p-tolyloxy-piperidin-I-yl)-acetamide;
2-[4-(4-chloro-benzyl)-piperidin-1-yl]-2-oxo-N-(2-oxo-2,3-dihydro-1H-indol-5-yl)-acetamide;
6-[2-(4-benzyl-piperidin-1-yl)-2-oxo-ethylamino]-3H-benzoxazol-2-one;
2-(4-benzyl-piperidin-1-yl)-N-(2-mercapto-3H-benzimidazol-5-yl)-2-oxo-acetamide;
2-(4-benzyl-piperidin-1-yl)-2-oxo-N-(2-oxo-2,3-dihydro-benzothiazol-6-yl)-acetamide;
2-[4-(4-fluoro-benzyl)-piperidin-1-yl]-N-(2-mercapto-3H-benzimidazol-5-yl)-2-oxo-acetamide;
2-[4-(4-fluoro-benzyl)-piperidin-1-yl]-2-oxo-N-(2-oxo-2,3-dihydro-benzothiazol-6-yl) acetamide;
2-oxo-N-(2-oxo-2,3-dihydro-benzothiazol-6-yl)-2-(4-p-tolyloxy-piperidin-1-yl)-acetamide;
N-(2-mercapto-3H-benzimidazol-5-yl)-2-(4-p-tolyloxy-piperidin-1-yl)-2-oxo-acetamide;
2-[4-(4-methyl-benzyl)-piperidin-1-yl ]-2-oxo-N-(2-oxo-2,3-dihydro-benzoxazol-6-yl] acetamide;
2-[4-[4-methoxy-benzyl)-piperidin-1-yi]-2-oxo-N-(2-oxo-2,3-dihydro-benzoxazol-6-yl) acetamide;
2-[4-[3-methoxy-benzyl)-piperidin-1-yl]-2-oxo-N-(2-oxo-2,3-dihydro-benzoxazol-6-yl) acetamide;
2-[4-[3-methyl-benzyl)-piperidin-1-yl]-2-oxo-N-(2-oxo-2,3-dihydro-benzoxazol-6-yl) acetamide;
2-[4-(4-cyano-benzyl)-piperidin-1-yl]-2-oxo-N-(2-oxo-2,3-dihydro-benzoxazol-6-yl)acetamide;
2-[4-[3-fluoro-benzyl)-piperidin-1-yl]-2-oxo-N-(2-oxo-2,3-dihydro-benzoxazol-6-yl)acetamide;
2-[4-(2,4-difluoro-benzyl)-piperidin-1-yl]-2-oxo-N-(2-oxo-2,3-dihydro-benzoxazol-6-yl) acetamide;
6-(2-[4-(4-methyl-benzyl)-piperidin-1-yl]-2-oxo-ethylamino}-3H-benzoxazol-2-one;
2-[4-(3,4-difluoro-benzyl)-piperidin-1-yl]-2-oxo-N-(2-oxo-2,3-dihydro-benzoxazol-6-yl) acetamide;
2-[4-(4-methyl-benzyl)-piperidin-1-yl)-2-oxo-N-(2-oxo-1,2,3,4-tetrahydro-quinolin-6-yl acetamide;
2-[4-(4-methyl-benzyl)-piperidin-1-yl]-2-oxo-N-(2-oxo-2,3-dihydro-benzothiazol-6-yl) acetamide;
2-[4-(4-chloro-phenoxy)-piperidin-1-yl]-2-oxo-N-(2-oxo-2,3-dihydro-benzothiazol-6-yl) acetamide; or
2-oxo-N-(2-oxo-2,3-dihydro-benzoxazol-6-yl)-2-(4-p-tolyloxy-piperidin-1-yl)-acetamide;

or an optical antipode, racemate or pharmaceutically-acceptable salt thereof.

6. The compound of claim 1 wherein the compound is a functional antagonist of NMDA receptors.

7. The compound of claim 6 wherein the compound is a functional NR2B subtype specific NMDA receptor antagonist.

8. The compound of claim 6 wherein the compound exhibits an $IC_{50}$ value of less than 54 μM in a NMDA antagonism or binding test.

9. The compound of claim 8 wherein the compound exhibits an $IC_{50}$ value of less than 5 μM in a NMDA antagonism or binding test.

10. The compound of claim 1, which is synthesized by a method comprising reacting a carboxylic acid of formula (II):

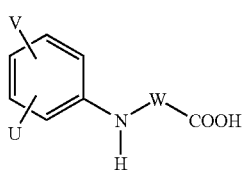
(II)

wherein U, V and W are as defined in claim 1, or a reactive derivative thereof, with an amine of formula (III):

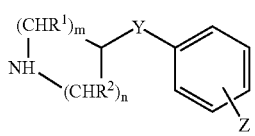
(III)

wherein $R^1$, $R^2$, Y, Z, n and m are as defined in claim 1.

11. The compound of claim 1, wherein W is —CO—, synthesized by a method comprising reacting a carboxylic acid of formula (IV):

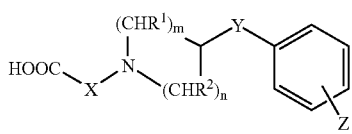
(IV)

wherein X, $R^1$, $R^2$, Y, Z, n and m are as defined in claim 1, or a reactive derivative thereof, with
an amine of formula (V):

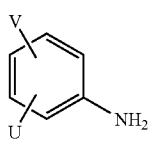
(V)

wherein U and V are as defined in claim 1.

12. The compound of claim 1, wherein W is —CH₂— or —CH₂—(C₁-C₄ alkyl)-, synthesized by a method comprising reacting a halogen derivative of formula (VII):

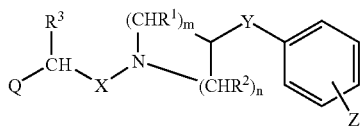
(VII)

wherein Q is halogen, $R^3$ is hydrogen atom or a $C_1$-$C_4$ alkyl and X, $R^1$, $R^2$, Y, Z, n and m are as defined in claim 1 with an amine of formula (V):

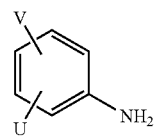
(V)

wherein U and V are as defined in claim 1.

13. The compound of claim 1 synthesized by a method comprising reacting a secondary amine of formula (III):

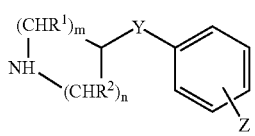
(III)

where $R^1$, $R^2$, m, n, Y and Z are as defined in claim 1 with ethyl oxalylchloride in the presence of a solid-supported base in dichloromethane to produce an ester compound of formula (VIII):

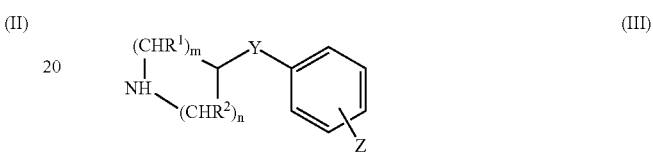
(VIII)

wherein $R^1$, $R^2$, m, n, Y and Z are as defined as in claim 1;

saponifying the ester compound of formula (VIII) with a strongly basic ion exchange resin in ethanol to produce an oxalamid acid of formula (IX):

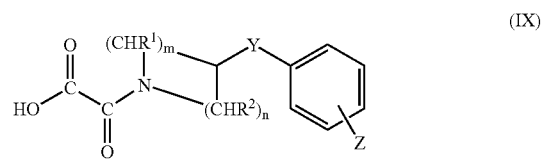
(IX)

where $R^1$, $R^2$, m, n, Y and Z are as defined in claim 1; and reacting the oxalamid acid of formula (IX) with an amide of formula (V):

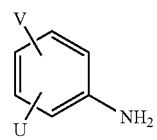
(V)

wherein U and V are as defined in claim 1 in a mixture of dichloromethane and dimethylformamide in the presence of 1-[3-(dimethylamino)-propyl]-3-ethylcarbodiimide to produce the compound of claim 1.

14. A pharmaceutical composition comprising a biologically effective dose of a compound of formula (I):

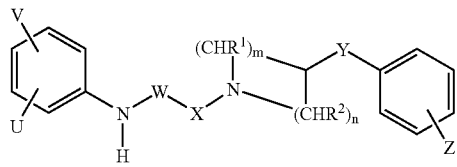

wherein:
V and U:
    together form a group that contains one or more heteroatoms, and that taken together with one or more:
    (a) hydrogen atoms;
    (b) carbon atoms;
    (c) —CH═ groups;
    (d) —CH$_2$— groups; or
    (e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4-oxazine, oxazole, oxazolidine, oxo-oxazolidine, thioxo-oxazolidine or 3-oxo- 1,4-oxazine;
    W: is —CO—, —CH$_2$— or —CH$_2$—(C$_1$-C4 alkyl)-;
    X: is —CO—;
    Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
    Z: is hydrogen, halogen, nitro, amino, C$_1$-C$_4$ alkyl, C$_1$-C$_4$ alkoxy, cyano, trifluoromethyl, hydroxyl or carboxyl;
    R$^1$ and R$^2$: are hydrogen, or together form a C$_1$-C$_3$ bridge; and
    n and m: independently are 0-3, wherein n and m cannot each be 0, and wherein m+n=4;
or an optical antipode, racemate or pharmaceutically-acceptable salt thereof, and one or more pharmaceutical carriers.

15. The pharmaceutical composition of claim 14 wherein the compound is a functional antagonist of NMDA receptors.

16. The pharmaceutical composition of claim 15 wherein the compound is a functional NR2B subtype specific NMDA receptor antagonist.

17. The pharmaceutical composition of claim 14 wherein the pharmaceutical composition contains 0.01 to 100 mg of the compound in a single dosage unit.

18. The pharmaceutical composition of claim 14 wherein the pharmaceutical composition is in the form of a tablet.

19. A method for alleviating pain in a mammal comprising administering to the mammal a compound of formula (I):

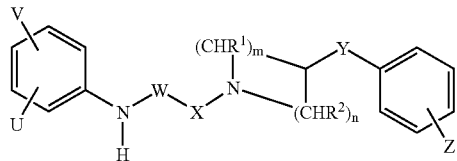

wherein:
V and U:
    together form a group that contains one or more heteroatoms, and that taken together with one or more:
    (a) hydrogen atoms;
    (b) carbon atoms;
    (c) —CH═ groups;
    (d) —CH$_2$— groups; or
    (e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4-oxazine, oxazole, oxazolidine, oxo-oxazolidine, thioxo-oxazolidine or 3-oxo- 1,4-oxazine;
    W: is —CO—, —CH$_2$— or —CH$_2$—(C$_1$-C$_4$ alkyl)-;
    X: is —CO—;
    Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
    Z: is hydrogen, halogen, nitro, amino, C$_1$-C$_4$ alkyl, C$_1$-C$_4$ alkoxy, cyano, trifluoromethyl, hydroxyl or carboxyl;
    R$^1$ and R$^2$: are hydrogen, or together form a C$_1$-C$_3$ bridge; and
    n and m: independently are 0-3, wherein n and m cannot each be 0, and wherein m+n=4;
or an optical antipode, racemate or pharmaceutically-acceptable salt thereof,
wherein the compound of formula (I) is administered in an amount effective for alleviating at least one symptom of the disease or disorder, and
wherein the pain is caused by a disease or disorder selected from the group consisting of a traumatic injury of a brain or spinal cord, human immunodeficleney virus related neuronal injury, amyotrophic lateral sclerosis, tolerance or dependence to opioid pain treatment, withdrawal syndromes from alcohol, opioids or cocaine, ischemic CNS disorders, chronic neurodegenerative disorders, Alzheimer's disease, Parkinson's disease, Huntington's disease, epilepsy, anxiety, depression, migraine, psychosis, muscular spasm, dementia, hypoglycemia, degenerative disorders of the retina, glaucoma, asthma, tinnitus or hearing loss.

20. A process for synthesizing a compound of formula (I):

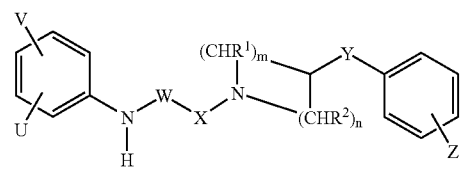

wherein:
V and U:
    together form a group that contains one or more heteroatoms, and that taken together with one or more:
    (a) hydrogen atoms;
    (b) carbon atoms;
    (c) —CH═ groups;
    (d) —CH$_2$— groups; or
    (e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4- oxazine, oxazole, oxazolidine, oxo-oxazolidine, thioxo-oxazolidine or 3-oxo- 1,4-oxazine;

W: is —CO—, —CH$_2$— or —CH$_2$—(C$_1$-C$_4$ alkyl)-;
X: is —CO—;
Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
Z: is hydrogen, halogen, nitro, amino, C$_1$-C$_4$ alkyl, C$_1$-C$_4$ alkoxy, cyano, trifluoromethyl, hydroxyl or carboxyl;
R$^1$ and R$^2$: are hydrogen, or together form a C$_1$-C$_3$ bridge; and
n and m: independently are 0-3, wherein n and m cannot each be 0, and wherein m+n=4;

or an optical antipode, racemate or pharmaceutically-acceptable salt thereof, comprising:
reacting a carboxylic acid of formula (II):

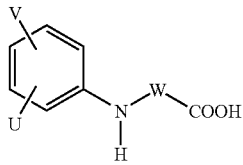

(II)

wherein U, V and W are as defined above, or a reactive derivative thereof, with an amine of formula (III):

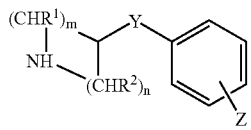

(III)

wherein R$^1$, R$^2$, Y, Z, n and m are as defined above.

21. The process of claim 20 wherein the reactive derivative of the carboxylic acid of formula (II) is formed using O-benzotriazol-1-yl-N,N,N',N' tetramethyluronium hexafluorophosphate.

22. A process for synthesizing a compound of formula (1):

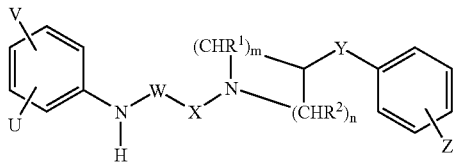

(I)

wherein:
V and U:
together form a group that contains one or more heteroatoms, and that taken together with one or more:
(a) hydrogen atoms;
(b) carbon atoms;
(c) —CH= groups;
(d) —CH$_2$— groups; or
(e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4- oxazine, oxazole, oxazolidine, oxo-oxazolidine, thioxo-oxazolidine or 3-oxo- 1,4-oxazine;

W: is —CO—, —CH$_2$— or —CH$_2$—(C$_1$-C$_4$ alkyl)-;
X: is —CO—;
Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
Z: is hydrogen, halogen, nitro, amino, C$_1$-C$_4$ alkyl, C$_1$-C$_4$ alkoxy, cyano, trifluoromethyl, hydroxyl or carboxyl;
R$^1$ and R$^2$: are hydrogen, or together form a C$_1$-C$_3$ bridge; and
n and m: independently are 0-3, wherein n and m cannot each be 0, and wherein m+n=4;

or an optical antipode, racemate or pharmaceutically-acceptable salt thereof, comprising:
reacting a carboxylic acid of formula (IV):

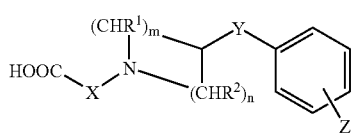

(IV)

wherein X, R$^1$, R$^2$, Y, Z, n and m are as defined above, or a reactive derivative thereof, with an amine of formula (V):

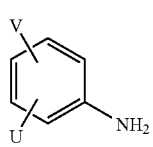

(V)

wherein U and V are as defined above.

23. The process of claim 22 wherein the reactive derivative of the carboxylic acid of formula (IV) is formed using O-benzotriazol-1-yl-N,N,N,N tetramethyluronium hexafluorophosphate.

24. A process for synthesizing a compound of formula (I):

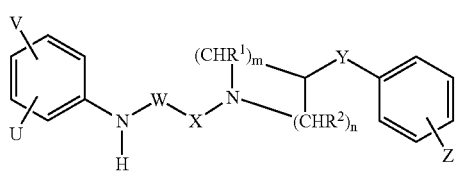

(I)

wherein:
V and U:
together form a group that contains one or more heteroatoms, and that taken together with one or more:
(a) hydrogen atoms;
(b) carbon atoms;
(c) —CH= groups;
(d) —CH$_2$— groups; or
(e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4-oxazine, oxazole, oxazolidine, oxo-oxazolidine, thioxo-oxazolidine or 3-oxo- 1,4-oxazine;

W: is —CO—, —CH$_2$— or —CH$_2$—(C$_1$-C$_4$ alkyl)-;
X: is —CO—;
Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
Z: is hydrogen, halogen, nitro, amino, C$_1$-C$_4$ alkyl, C$_1$-C$_4$ alkoxy, cyano, trifluoromethyl, hydroxyl or carboxyl;
R$^1$ and R$^2$: are hydrogen, or together form a C$_1$-C$_3$ bridge; and
n and m: independently are 0-3, wherein n and m cannot each be 0, and wherein m+n=4;
or an optical antipode, racemate or pharmaceutically-acceptable salt thereof, comprising:
reacting a halogen derivative of formula (VII):

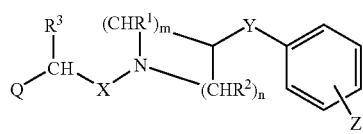
(VII)

wherein Q is halogen, R$^3$ is hydrogen or a C$_1$-C$_4$ alkyl and X, R$^1$, R$^2$, Y, Z, n and m are as defined above with an amine of formula (V):

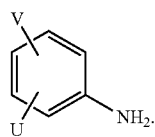
(V)

wherein U and V are as defined above.

25. A process for synthesizing a compound of formula (1):

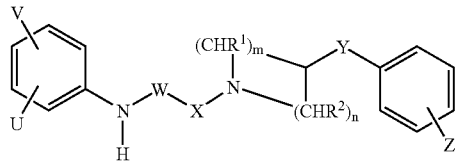
(I)

wherein:
V and U:
together form a group that contains one or more heteroatoms, and that taken together with one or more:
(a) hydrogen atoms;
(b) carbon atoms;
(c) —CH= groups;
(d) —CH$_2$— groups; or
(e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4-oxazine, oxazole, oxazolidine, oxo-oxazolidine, thioxo-oxazolidine or 3-oxo- 1,4-oxazine;
W: is —CO—, —CH$_2$— or —CH$_2$—(C$_1$-C$_4$ alkyl)-;
X: is —CO—;
Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;
Z: is hydrogen, halogen, nitro, amino, C$_1$-C$_4$ alkyl, C$_1$-C$_4$ alkoxy, cyano, trifluoromethyl, hydroxyl or carboxyl;
R$^1$ and R$^2$: are hydrogen, or together form a C$_1$-C$_3$ bridge; and
n and m: independently are 0-3, wherein n and m cannot each be 0, and wherein m+n=4;
or an optical antipode, racemate or pharmaceutically-acceptable salt thereof, comprising:
reacting a secondary amine of formula (III):

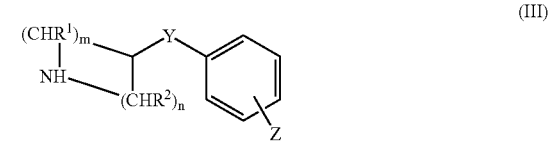
(III)

where R$^1$, R$^2$, m, n, Y and Z are as defined above with ethyl oxalylchloride in the presence of a solid-supported base in dichloromethane to produce an ester compound of formula (VIII):

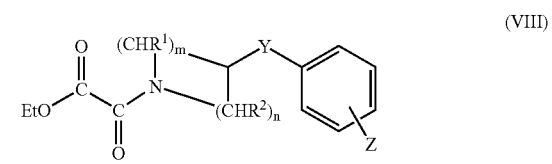
(VIII)

wherein R$^1$, R$^2$, m, n, Y and Z are as defined above,
saponifying the ester compound of formula (VIII) with a strongly basic ion exchange resin in ethanol to produce an oxalamid acid of formula (IX):

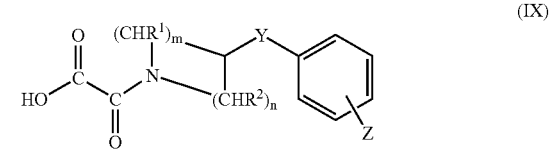
(IX)

where R$^1$, R$^2$, m, n, Y and Z are as defined above, and
reacting the oxalamid acid of formula (IX) with an amide of formula (V):

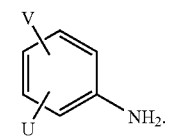
(V)

wherein U and V are as defined above in a mixture of dichloromethane and dimethylformamide in the presence of 1-[3-(dimethylamino)-propyl]-3-ethylcarbodiimide to produce the compound of claim 1.

26. A process for manufacturing pharmaceutical compositions comprising mixing a compound of formula (1):

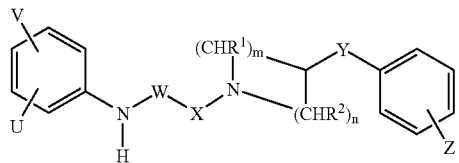

wherein:

V and U:
  together form a group that contains one or more heteroatoms, and that taken together with one or more:
  (a) hydrogen atoms;
  (b) carbon atoms;
  (c) —CH= groups;
  (d) —CH$_2$— groups; or
  (e) additional heteroatoms of the same or different type;
or any combination thereof, form a 4-7 membered homocyclic or heterocyclic ring, wherein the heterocyclic ring is selected from the group consisting of morpholine, pyrrole, pyrrolidine, oxo-pyrrolidine, thioxo-pyrrolidine, pyrazole, pyrazolidine, imidazole, oxo-imidazole, thioxo-imidazole, imidazolidine, oxo-imidazolidine, thioxo-imidazolidine, 1,4-oxazine, oxazole, oxazolidine, oxo-oxazolidine, thioxo-oxazolidine or 3-oxo- 1,4-oxazine;

W: is —CO—, —CH$_2$— or —CH$_2$—(C$_1$-C$_4$ alkyl)-;

X: is —CO—;

Y: is —O—, C$_1$-C$_4$ alkylene, C$_1$-C$_4$ alkynylene, cycloalkylene, aminocarbonyl, —NH—, —N(C$_1$-C$_4$ alkyl)-, —C$_1$-C$_4$ alkylene-N(C$_1$-C$_4$ alkyl)-, —CH$_2$O—, —CH(OH)— or —OCH$_2$—;

Z: is hydrogen, halogen, nitro, amino, C$_1$-C$_4$ alkyl, C$_1$-C$_4$ alkoxy, cyano, trifluoromethyl, hydroxyl or carboxyl;

R$^1$ and R$^2$: are hydrogen, or together form a C$_1$-C$_3$ bridge; and n and m: independently are 0-3, wherein n and m cannot each be 0, and wherein m+n=4;

or an optical antipode, racemate or pharmaceutically-acceptable salt thereof, with a pharmaceutical carrier.

27. The process of claim 26 wherein the compound is a functional NR2B subtype specific NMDA receptor antagonist.

* * * * *

UNITED STATES PATENT AND TRADEMARK OFFICE
CERTIFICATE OF CORRECTION

| | | |
|---|---|---|
| PATENT NO. | : 7,435,744 B2 | Page 1 of 1 |
| APPLICATION NO. | : 10/761940 | |
| DATED | : October 14, 2008 | |
| INVENTOR(S) | : O'Brady et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this
Twenty-sixth Day of June, 2012

David J. Kappos
*Director of the United States Patent and Trademark Office*